United States Patent [19]
Jakobi et al.

[11] Patent Number: 5,925,644
[45] Date of Patent: Jul. 20, 1999

[54] SUBSTITUTED NITROGEN HETEROCYCLES, PROCESSES FOR THEIR PREPARATION AND THEIR USE AS PESTICIDES

[75] Inventors: Harald Jakobi, Frankfurt; Oswald Ort, Glashütten; Wolfgang Schaper, Diedorf; Ralf Braun, Dernbach; Gerhard Krautstrunk; Martin Märkl, both of Frankfurt; Herbert Stark, Kelkheim; Ulrich Sanft, Hofheim; Maria-Theresia Thönessen, Heidesheim; Manfred Kern, Lörzweiler; Werner Bonin, Kelkheim, all of Germany

[73] Assignee: Hoechst Schering AgrEvo GmbH, Berlin, Germany

[21] Appl. No.: 08/969,922

[22] Filed: Nov. 13, 1997

[30] Foreign Application Priority Data

Nov. 15, 1996 [DE] Germany .......................... 196 47 317

[51] Int. Cl.⁶ .................... C07D 239/42; C07D 239/47; A01N 43/54
[52] U.S. Cl. ..................... 514/269; 514/256; 514/258; 544/283; 544/298; 544/322
[58] Field of Search .................... 514/256, 258, 514/269; 544/253, 298, 322, 283

[56] References Cited

U.S. PATENT DOCUMENTS

| | | | |
|---|---|---|---|
| 4,107,313 | 8/1978 | Bailey | 544/253 |
| 5,055,469 | 10/1991 | Mitsumori et al. | 514/252 |

FOREIGN PATENT DOCUMENTS

| | | |
|---|---|---|
| 0057440 | 8/1982 | European Pat. Off. |
| 0196524 | 10/1986 | European Pat. Off. |
| 0264217 | 4/1988 | European Pat. Off. |
| 0323757 | 7/1989 | European Pat. Off. |
| 0326329 | 8/1989 | European Pat. Off. |
| 0432894 | 6/1991 | European Pat. Off. |
| 0274217 | 4/1998 | European Pat. Off. |
| 27 08 331 | 9/1977 | Germany. |
| 40 05 178 | 8/1991 | Germany. |
| WO 93/04580 | 3/1993 | WIPO. |
| WO 93/19050 | 9/1993 | WIPO. |
| WO 94/21613 | 9/1994 | WIPO. |
| WO 95/07890 | 3/1995 | WIPO. |

OTHER PUBLICATIONS

Journal of Organic Chemistry, vol. 29, 1964, pp. 3407–3410, XP002058825 entitled "A Synthesis of 1,2,3,4,6,7,12,12b–Octahydro–2–Oxoindolo[2,3–a]quinolizine", by K.T. Potts, I.D. Nasri.

J. Pernak et al.; Arch. Pharm (Weinheim) vol. 328, pp. 531–533, XP002062956, 1995.

J. Pernak et al. vol. 39, No. 11, 1984, pp. 782–783, XP00206957.

J. Pernak et al. vol. 42, No. 10, 1984, pp. 703–704, XP002062958.

Chemical Abstracts, vol. 121, No. 9, Aug. 29, 1994, Abstract No. 108471K.

*Primary Examiner*—Zinna Northington Davis
*Attorney, Agent, or Firm*—Frommer Lawrence & Haug LLP

[57] ABSTRACT

Compounds of the formula I

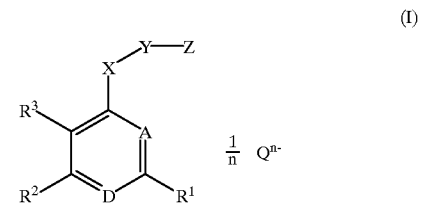

in which A is CH and D is $N^+R$, A is nitrogen and D is $N^+R$ or A is $N^+R$ and D is nitrogen, R is $—CR^4R^5—E—R^6$, $Q^{n-}$ is an inorganic or organic anion, n is 1, 2, 3 or 4 and $R^1–R^6$, E, X, Y and Z are each as defined in the description, processes for their preparation and their use as pesticides.

20 Claims, No Drawings

SUBSTITUTED NITROGEN HETEROCYCLES, PROCESSES FOR THEIR PREPARATION AND THEIR USE AS PESTICIDES

The invention relates to novel substituted pyridines and pyrimidines and condensed systems derived therefrom, processes for their preparation and their use as pesticides and fungicides.

It is already known that certain 4-amino- and 4-alkoxy-heterocycles have fungicidal, acaricidal and insecticidal activity (cf. for example EP-A-57 440, EP-A-196 524, EP-A-264 217, EP-A-326 329, EP-A-323 757, EP-A-432 894, DE-A-4 116 089, WO 93/04 580). However, the biological activity of these compounds, in particular at low application rates and concentrations, is not satisfactory in all use examples.

Novel, positively charged nitrogen heterocycles of the formula I have been found

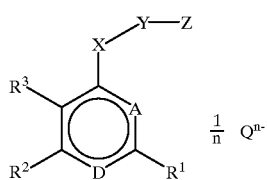

(I)

in which the radicals and groups are as defined below, which, while showing good tolerance by plants and favorable toxicity in respect of warm-blooded animals, are highly suitable for controlling animal pests, such as insects, arachnids, nematodes, helminths and molluscs, for controlling endoparasites and ectoparasites in the veterinary field, and for controlling harmful fungi.

The invention therefore relates to compounds of the formula I in which
(1) A is CH and D is $N^+R$ or
A is nitrogen and D is $N^+R$ or
A is $N^+R$ and D is nitrogen;
R is

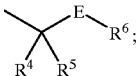

(2) $Q^{n-}$ is any inorganic or organic anion, n being 1, 2, 3 or 4;
(3) $R^1$ is hydrogen, halogen, $(C_1-C_4)$-alkyl, $(C_1-C_4)$-haloalkyl or $(C_3-C_5)$-cycloalkyl;
(4) $R^2$ and $R^3$ are identical or different and are each hydrogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_1-C_8)$-trialkylsilylalkynyl, preferably dimethyl-$(C_1-C_8)$-alkylsilylalkynyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_1-C_4)$-alkoxy-$(C_1-C_4)$-haloalkyl, $(C_1-C_4)$-haloalkoxy-$(C_1-C_4)$-haloalkyl, halogen, hydroxyl, $(C_1-C_4)$-hydroxyalkyl, $(C_1-C_4)$-alkanoyl, $(C_1-C_4)$-alkanoyl-$(C_1-C_4)$-alkyl, $(C_1-C_4)$-haloalkanoyl, $(C_3-C_5)$-cycloalkyl, $(C_3-C_5)$-halocycloalkyl, cyano, $(C_1-C_4)$-cyanoalkyl, nitro, $(C_1-C_4)$-nitroalkyl, thiocyano, $(C_1-C_4)$-thiocyanoalkyl, $(C_1-C_4)$-alkoxycarbonyl, $(C_1-C_4)$-alkoxycarbonyl-$(C_1-C_4)$-alkyl, $(C_1-C_4)$-haloalkoxycarbonyl, $(C_1-C_4)$-alkylthio, $(C_1-C_4)$-alkylthio-$(C_1-C_4)$-alkyl, $(C_1-C_4)$-haloalkylthio, $(C_1-C_4)$-alkylsulfinyl, $(C_1-C_4)$-haloalkylsulfinyl, $(C_1-C_4)$-alkylsulfonyl or $(C_1-C_4)$-haloalkylsulfonyl; or
$R^2$ and $R^3$, together with the carbon atoms to which they are attached, form an unsaturated 5- or 6-membered isocyclic ring which may, if it is a 5-membered ring, contain an oxygen or sulfur atom instead of $CH_2$, or which may, if it is a 6-membered ring, contain one or two nitrogen atoms instead of one or two CH units, and which may be substituted by 1, 2 or 3 identical or different radicals, these radicals being $(C_1-C_4)$-alkyl, $(C_1-C_4)$-haloalkyl, preferably trifluoromethyl, halogen, $(C_1-C_4)$-alkoxy or $(C_1-C_4)$-haloalkoxy; or
$R^2$ and $R^3$, together with the carbon atoms to which they are attached, form a saturated 5-, 6- or 7-membered isocyclic ring which may contain oxygen and/or sulfur instead of one or two $CH_2$ groups and which may be substituted by 1, 2 or 3 $(C_1-C_4)$-alkyl groups;
(5) X is O or NH
and the group Y-Z may have the following meanings:
a) Y is $CHR^7$ and $R^7$ is hydrogen, $(C_1-C_4)$-alkyl or $(C_3-C_6)$-cycloalkyl and
Z is a branched or straight-chain, saturated or unsaturated $(C_1-C_{20})$-hydrocarbon radical in which one or more, preferably up to three, nonadjacent carbon units may be replaced by a carbonyl group or by hetero atom units such as oxygen or $S(O)_x$, where x=0, 1 or 2, and where these hydrocarbon radicals with or without the variations mentioned may be substituted by one or more, preferably up to three (in the case of fluorine up to the maximum number), identical or different radicals selected from the group consisting of halogen, hydroxyl, $(C_3-C_6)$-cycloalkyl, $(C_3-C_6)$-cycloalkenyl, deca-, tetra- or dihydronaphthyl, substituted or unsubstituted benzyloxy, substituted or unsubstituted phenylthio, substituted or unsubstituted benzylthio, imidazol-1-yl, triazol-1-yl, pyrazol-1-yl, $(C_1-C_4)$-alkoxycarbonyl or by a group M—G—$R^8$ in which M may be oxygen or NH, G may be carbonyl, thiocarbonyl or sulfonyl and $R^8$ may be $(C_1-C_8)$-alkyl, $(C_3-C_6)$-cycloalkyl, $(C_1-C_8)$-haloalkyl, $(C_1-C_8)$-alkoxy, a substituted or unsubstituted phenyl group, a substituted or unsubstituted phenoxy group, a substituted or unsubstituted anilino group, imidazol-1-yl, triazol-1-yl, pyrazol-1-yl or mono- or di-$(C_1-C_4)$-alkylamino, or, if not included in the above definition,
b) Y is a $(C_1-C_6)$-alkylene unit, branched or straight-chain, which may be substituted by up to 3 halogen atoms, preferably fluorine or chlorine, or by a hydroxyl, $(C_1-C_4)$-alkoxy, $(C_3-C_6)$-cycloalkyl or cyano group and
Z is an unsubstituted or substituted aryl, aryloxy, heterocyclyl or pyridinyloxy group with or without substitution, where the aryloxy or pyridinyloxy group is separated from X by at least 2 carbon atoms, or
c) in the case that X is NH,
Y is a carbonyl or thiocarbonyl group and
Z is a substituted or unsubstituted aryl-$(C_1-C_4)$-alkyl radical, a $(C_1-C_4)$-alkyl radical which is in each case substituted by a substituted or unsubstituted heterocyclic or benzo-fused carbocyclic or heterocyclic ring system or a $(C_3-C_8)$-cycloalkyl or cycloalkenyl radical with or without substitution.

In the above formula, in the radicals and substituents described under the group Y Z under a):

the term "($C_1$–$C_4$)-alkyl" denotes a straight-chain or branched hydrocarbon radical having 1 to 4 carbon atoms such as, for example, the methyl, ethyl, propyl, isopropyl, 1-butyl, 2-butyl, 2-methylpropyl or tert-butyl radical;

the term "($C_3$–$C_6$)-cycloalkyl" denotes the cyclopropyl, cyclobutyl, cyclopentyl or cyclohexyl group;

a "branched or straight-chain, saturated or unsaturated ($C_1$–$C_{20}$)-hydrocarbon radical in which one or more, preferably up to three, nonadjacent saturated carbon units may be replaced by a carbonyl group or by hetero atom units such as oxygen or S(O)$_x$, where x=0, 1 or 2" denotes, for example, the methyl, ethyl, propyl, butyl, pentyl, hexyl, heptyl, octyl, nonyl, decyl or undecyl radical or branched radicals such as the sec-butyl, tert-butyl, isobutyl, isopentyl, 7-methyloctyl or the 10-methylundecyl radical or unsaturated radicals such as, for example, the allyl, 3,7-dimethyl-6-octen-1-yl radical or the propargyl radical or radicals containing a carbonyl group such as, for example, the 6-oxopentyl or the 8-oxononyl radical or radicals containing one or more oxygen such as, for example, the hexyloxymethyl, methoxyhexyl, butoxypropyl, 2-(ethoxyethoxy)ethyl or 3-(methoxyethoxy)propyl radical or radicals containing sulfur, the sulfoxide or sulfonyl group such as, for example, the 4-(propylthio) butyl, 7-(methylthio)heptyl, 7-(methylsulfoxy)heptyl or 7-(methylsulfonyl)heptyl radical, the term "($C_3$–$C_6$)-cycloalkenyl" denotes, for example, the cyclopenten-4-yl-, cyclohexen-3-yl or the cyclohexen-4-yl group;

a "substituted benzyloxy group" denotes, for example, a 4-chloro, 4-fluoro, 4-methyl, 4-trifluoromethyl or 2,4-dimethylbenzyloxy group;

furthermore, the group M—G—$R^8$ may denote, for example, N,N-dimethylcarbamoyloxy, N,N-dimethylthiocarbamoyloxy, imidazol-1-ylcarbonyloxy, benzoyloxy, pivaloyloxy, 4-methylphenylcarbamoyloxy, methylsulfonyloxy or 4-methylphenylsulfonyloxy;

furthermore, in the substituents and radicals described under the group Y Z under b):

a "($C_1$–$C_6$)-alkylene unit, branched or straight-chain, which may be substituted by up to 3 halogen atoms, preferably fluorine or chlorine, or by a hydroxyl, ($C_1$–$C_4$)-alkoxy, ($C_3$–$C_6$)-cycloalkyl or cyano group" denotes, for example, methylene, ethylene, CH(CH$_3$), propylene, CH(C$_2$H$_5$), butylene, CH(CH$_3$)(CH$_2$)$_2$, —(CH$_2$)$_2$—CH(CH$_3$), CH$_2$CH(CH$_3$)CH$_2$,

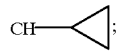

CH(CH$_2$OH)CH$_2$, CH(CH$_2$OH)CH$_2$CH$_2$, CH(CH$_2$CN)CH$_2$, or CH(CH$_2$CN)CH$_2$CH$_2$;

the term "aryl group" denotes a naphthyl or, preferably, a phenyl group;

the term "substituted aryl group" denotes a naphthyl or, preferably, phenyl group in which up to three hydrogen atoms, in the case of fluorine as substituent even all hydrogen atoms, are replaced by identical or different substituents, possible substituents being:

halogen,
($C_3$–$C_8$)-cycloalkyl,
($C_3$–$C_8$)-cycloalkenyl, a group U-W where U is a direct bond, oxygen, S(O)$_x$ where x=0, 1 or 2, ($C_1$–$C_4$)-alkylene or ($C_1$–$C_4$)-alkyleneoxy and where W is substituted or unsubstituted aryl or heteroaryl, preferably pyridinyl, pyrimidinyl, thienyl or furyl;

nitro, cyano, hydroxyl, ($C_1$–$C_8$)-alkanoyloxy, a group

where $R^9$ is ($C_1$–$C_8$)-alkyl, ($C_1$–$C_8$)-alkoxy, cycloalkyl, phenyl or substituted phenyl, a group NR$^{10}$R$^{11}$ where $R^{10}$ and $R^{11}$ independently of one another are each hydrogen, ($C_1$–$C_4$)-alkyl, or ($C_1$–$C_4$)-aryl;

a group L-S(O)$_y$R$^{12}$ where L is a direct bond or oxygen, $R^{12}$ is ($C_1$–$C_8$)-alkyl, aryl, substituted aryl, benzyl or substituted benzyl and y may be 1 or 2;

SiR$^{13}$R$^{14}$R$^{15}$ or OSiR$^{13}$R$^{14}$R$^{15}$ where $R^{13}$, $R^{14}$ and $R^{15}$ independently of one another are each ($C_1$–$C_8$)-alkyl, ($C_3$–$C_8$)-cycloalkyl or substituted or unsubstituted phenyl;

a saturated or unsaturated $C_1$–$C_{12}$-hydrocarbon radical which may be branched or straight-chain and where one or two saturated carbon units may be replaced by oxygen, sulfur or the groups SO, SO$_2$, NR$^{10'}$ or SiR$^{13'}$R14' and where $R^{10'}$, $R^{13'}$ and $R^{14'}$ are as defined above for $R^{10}$, $R^{13}$ and $R^{14}$, which may be substituted by a hydroxyl group, ($C_3$–$C_8$)-cycloalkyl, ($C_3$–$C_8$)-cycloalkenyl, ($C_1$–$C_4$)-acyl, ($C_1$–$C_4$)-alkoxycarbonyl, phenyl, substituted phenyl, phenoxy, substituted phenoxy, phenylthio, substituted phenylthio or cyano;

($C_1$–$C_8$)-alkoxy, which may be substituted by phenyl, substituted phenyl, phenoxy, substituted phenoxy, ($C_3$–$C_8$)-cycloalkyl or ($C_3$–$C_8$)-cycloalkenyl;

($C_3$–$C_8$)-cycloalkoxy;

($C_1$–$C_8$)-alkylthio, which may be substituted by phenyl, substituted phenyl, phenoxy, substituted phenoxy, ($C_3$–$C_8$)-cycloalkyl;

($C_1$–$C_8$)-alkenyloxy;

($C_1$–$C_8$)-alkynyloxy or a group

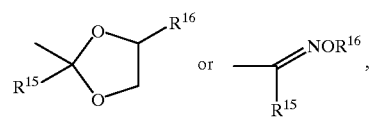

where $R^{15}$ is hydrogen, ($C_1$–$C_4$)-alkyl or ($C_3$–$C_6$)-cycloalkyl and $R^{16}$ is ($C_1$–$C_{10}$)-alkyl, ($C_2$–$C_{12}$)-alkoxyalkyl, ($C_3$–$C_8$)-alkenyloxy-($C_1$–$C_4$)-alkyl, ($C_3$–$C_8$)-alkynyloxy-($C_1$–$C_4$)-alkyl, ($C_2$–$C_{12}$)-alkylthioalkyl, aryl, aryloxy-($C_1$–$C_4$)-alkyl, aryl-($C_1$–$C_4$)-alkoxy-($C_1$–$C_4$)-alkyl, heteroaryloxy-($C_1$–$C_4$)-alkyl, ($C_1$–$C_4$)-alkoxy-($C_1$–$C_4$)-alkoxy-($C_1$–$C_4$)-alkyl or aryl-($C_1$–$C_4$)-alkyl;

furthermore, two substituents of the aryl group which are ortho to each other may be linked cyclically to form a saturated or partially saturated carbocyclic or heterocyclic ring system such as, for example, the tetrahydronaphthyl, tetrahydroquinoline, dihydrobenzopyran, dihydrobenzofuran, benzodioxan, benzodioxole system, or else to form systems of the formulae $Z_a$ or $Z_b$

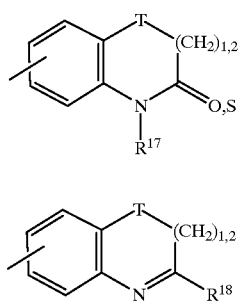

where
T is oxygen, sulfur, methylene or ethylene and
$R^{17}$ is hydrogen, methyl, ethyl or cyanomethyl and
$R^{18}$ is $(C_1-C_6)$-alkyl or $(C_1-C_6)$-alkylthio;
the term "aryloxy" denotes a phenoxy or naphthoxy group;
the term "substituted aryloxy group" denotes a naphthoxy or, preferably, phenoxy group in which up to three, in the case of fluorine even all, hydrogen atoms may be replaced by identical or different substituents, possible substituents being:
halogen,
cyano,
nitro,
$(C_1-C_8)$-alkyl,
$(C_1-C_8)$-alkenyl,
$(C_1-C_8)$-alkynyl,
$(C_1-C_8)$-alkoxy,
$(C_1-C_8)$-alkylthio,
$(C_1-C_4)$-alkoxy-$(C_1-C_4)$-alkyl,
$(C_1-C_4)$-alkoxy-$(C_1-C_4)$-alkoxy-$(C_1-C_4)$-alkyl,
a group of the formula M'-Ph in which M' is oxygen, methylene or a direct bond and Ph is a substituted or unsubstituted phenyl group;
the term "unsubstituted heterocyclyl group" denotes a 5- or 6-membered monocyclic or a 8-, 9- or 10-membered fused ring system which is aromatic or fully or partially hydrogenated, which contains 1 to 4 identical or different hetero atoms selected from the groups 0–4 nitrogen, 0–2 oxygen or 0–2 sulfur and which may be, for example: the furan, thiophene, thiazole, isothiazole, oxazole, isoxazole, pyrrole, pyrazole, imidazole, triazole, thiadiazole, oxadiazole, pyridine, pyrimidine, triazine, quinoline, quinazoline, benzothiazole, benzoxazole, benzimidazole, tetrahydrofuran, 1,3-dioxolane, tetrahydropyran, piperidine, piperazine, morpholine, 4,5-dihydro-5-isoxazole, benzofuran, benzothiophene, benzopyran, benzodioxane, dihydrobenzofuran, benzodioxole, 1,2,3,4-tetrahydroquinoline or the 4,5,6,7-tetrahydrofuran or -thiophene system;
the term "substituted heterocyclyl group" denotes, for example, one of the abovementioned heterocyclic groups in which up to three (in the case of fluorine as substituent even all) hydrogen atoms may be replaced by identical or different substituents, possible substituents being:
$(C_1-C_4)$-alkyl,
$(C_1-C_4)$-alkoxy,
$(C_1-C_4)$-alkylthio,
$(C_1-C_4)$-alkoxyalkyl,
halogen, cyano, nitro, substituted or unsubstituted phenyl, or substituted or unsubstituted phenoxy;
the term "unsubstituted or substituted pyridyloxy" denotes a 2-, 3- or 4-pyridyloxy group in which up to two hydrogen atoms may be replaced by halogen, $(C_1-C_4)$-alkyl, $(C_1-C_4)$-haloalkyl, $(C_2-C_4)$-alkenyl or $(C_1-C_4)$-alkoxy;
and where furthermore, in the alkyl, cycloalkyl, alkylene, alkenyl, cycloalkenyl, alkynyl, saturated or unsaturated hydrocarbon radicals or in radicals derived therefrom such as, for example, alkoxy, alkylthio, alkylsulfinyl, alkylsulfonyl, alkoxycarbonyl or the $CH_2$-group of the benzodioxole group listed as radicals, substituents or components of ring systems under group Y Z under b), unless defined otherwise, the hydrogen atoms may be replaced partly, in the case of fluorine even wholly, by halogen, preferably chlorine or fluorine, and furthermore one $CH_2$ group may be replaced by O, S, SO or $SO_2$;
and furthermore, in the substituents and radicals described under the group Y Z under c):
the term "unsubstituted aryl-$(C_1-C_4)$-alkyl radical" denotes, for example, the benzyl, naphthylmethyl, 2-phenylethyl, 1-phenylethyl or 3-phenylpropyl group;
the term "substituted aryl-$(C_1-C_4)$-alkyl radical" denotes, for example, one of the abovementioned aryl-$(C_1-C_4)$-alkyl radicals, preferably the benzyl radical, in which up to three, in the case of fluorine even all, hydrogen atoms of the phenyl ring may be replaced by substituents, possible substituents being
halogen,
$(C_3-C_8)$-cycloalkyl,
$(C_3-C_8)$-cycloalkenyl,
a group U-W where U is a direct bond, oxygen, $S(O)_x$, where x=0, 1 or 2, $(C_1-C_4)$-alkylene or $(C_1-C_4)$-alkyleneoxy and where W is substituted or unsubstituted phenyl or substituted or unsubstituted heteroaryl, preferably pyridinyl, pyrimidinyl, thienyl or furyl,
nitro, cyano, hydroxyl, acetoxy, a group

where $R^9$ is $(C_1-C_8)$-alkyl, $(C_1-C_8)$-alkoxy, cycloalkyl, phenyl or substituted phenyl,
a group $NR^{10}R^{11}$ where $R^{10}$ and $R^{11}$ independently of one another are each hydrogen, $(C_1-C_4)$-alkyl or $(C_1-C_4)$-aryl,
a group $L-S(O)_yR^{12}$ where L is a direct bond or oxygen, $R^{12}$ is $(C_1-C_8)$-alkyl, aryl, substituted aryl, benzyl or substituted benzyl and y may be 1 or 2;
$SiR^{13}R^{14}R^{15}$ or $OSiR^{13}R^{14}R^{15}$ where $R^{13}$, $R^{14}$ and $R^{15}$ independently of one another are each $(C_1-C_8)$-alkyl, $(C_3-C_8)$-cycloalkyl or substituted or unsubstituted phenyl;
a saturated or unsaturated $C_1-C_{12}$-hydrocarbon radical which may be branched or straight-chain and in which one or two saturated carbon units may be replaced by oxygen, sulfur or the groups SO, $SO_2$, $NR^{10}$ or $SiR^{13'}R^{14'}$ and where $R^{10'}R$, $R^{13'}$ and $R^{14'}$ have the meanings given above for $R^{10}$, $R^{13}$ and $R^{14}$, and which may be substituted by a hydroxyl group, $(C_3-C_8)$-cycloalkyl, $(C_3-C_8)$-cycloalkenyl, $(C_1-C_4)$-acyl, $(C_1-C_4)$-alkoxycarbonyl, phenyl, substituted phenyl, phenoxy, substituted phenoxy, phenylthio, substituted phenylthio or cyano;

($C_1$–$C_8$)-alkoxy which may be substituted by phenyl, substituted phenyl, phenoxy, substituted phenoxy, ($C_3$–$C_8$)-cycloalkyl, ($C_3$–$C_8$)-cycloalkoxy or ($C_3$–$C_8$)-cycloalkenyl;

($C_1$–$C_8$)-alkylthio which may be substituted by phenyl, substituted phenyl, phenoxy, substituted phenoxy, ($C_3$–$C_8$)-cycloalkyl;

($C_3$–$C_8$)-cycloalkoxy;

($C_1$–$C_8$)-alkenyloxy or ($C_1$–$C_8$)-alkynyloxy;

the term "substituted or unsubstituted heterocyclic or benzo-fused carbocyclic or heterocyclic ring system" denotes, for example, a furyl, thienyl, thiazolo, oxazolyl, benzodioxolyl, indanyl, tetrahydronaphthyl, benzothienyl, benzofuryl, benzoxazolyl, quinolinyl, isoquinolinyl, benzodioxanyl, benzotetrahydropyranyl, 1,2,3,4-tetrahydroquinolinyl or 2,3-dihydrobenzofuranyl or -thienyl radical in which one or two hydrogen atoms in the aromatic moiety of the ring system may be replaced, independently of one another, by halogen, ($C_1$–$C_6$)-alkyl, ($C_1$–$C_6$)-alkoxy, ($C_1$–$C_4$)-alkoxy-($C_1$–$C_4$)-alkyl, ($C_1$–$C_6$)-alkylthio, ($C_1$–$C_6$)-alkylsulfinyl, ($C_1$–$C_6$)-alkyls phenyl, benzyl, phenoxy, phenylthio, nitro, cyano, ($C_1$–$C_4$)-alkanoyl or ($C_1$–$C_4$)-alkoxycarbonyl;

the term "substituted or unsubstituted ($C_3$–$C_8$)-cycloalkyl or cycloalkenyl radical" denotes, for example, a cyclopropyl, cyclobutyl, cyclopentyl, cyclohexyl, cycloheptyl, cyclooctyl, cyclopenten-4-yl, cyclohexen-4-yl or cyclohexen-3-yl radical in which one or two hydrogen atoms may be replaced by ($C_1$–$C_4$)-alkoxy, ($C_1$–$C_4$)-alkyl, halogen or ($C_1$–$C_4$)-alkanoyl;

and where furthermore in the alkyl, cycloalkyl, alkylene, alkenyl, cycloalkenyl, alkynyl, saturated or unsaturated hydrocarbon radicals or radicals derived therefrom such as, for example, alkoxy, alkylthio, alkylsulfinyl, alkylsulfonyl or alkoxycarbonyl listed as radicals, substituents or components of ring systems under group Y Z under c), unless defined otherwise, the hydrogen atoms may be replaced partly, in the case of fluorine even wholly, by halogen, preferably chlorine or fluorine, and where furthermore one $CH_2$ group may be replaced by O, S, SO or $SO_2$, and where furthermore the substituted phenyl, heterocyclyl, heteroaryl, phenoxy, phenylthio, benzyl, benzyloxy, benzylthio or anilino groups listed as substituents under group Y Z denote radicals where in the phenyl groups of these radicals up to three, in the case of fluorine even all, hydrogen atoms may be replaced by halogen, ($C_1$–$C_4$)-alkyl, ($C_1$–$C_4$)-haloalkyl, ($C_1$–$C_4$)-alkoxy, ($C_1$–$C_4$)-haloalkoxy, ($C_1$–$C_4$)-alkoxy-($C_1$–$C_4$)-alkyl, ($C_1$–$C_4$)-alkylthio, ($C_1$–$C_4$)-haloalkylthio, ($C_1$–$C_4$)-alkylsulfonyl, ($C_1$–$C_4$)-haloalkylsulfonyl, ($C_1$–$C_4$)-alkylsulfinyl, ($C_1$–$C_4$)-haloalkylsulfinyl, trimethylsilyl, ($C_1$–$C_4$)-alkoxycarbonyl, nitro, cyano, mono- or di-($C_1$–$C_4$)-alkylamino, and furthermore a) $R^4$ and $R^5$ are identical or different and are each hydrogen, a branched or straight-chain, saturated or unsaturated ($C_1$–$C_{20}$)-hydrocarbon radical, halogen, aryl, substituted aryl or ($C_3$–$C_6$)-cycloalkyl;

E is oxygen, S(O)q where q=0, 1 or 2, or $NR^{19}$, where $R^{19}$ is hydrogen, ($C_1$–$C_4$)-alkyl, ($C_2$–$C_4$)-alkenyl or ($C_1$–$C_4$)-acyl, $R^6$ is a saturated or unsaturated, branched or straight-chain ($C_1$–$C_{20}$)-hydrocarbon radical, ($C_3$–$C_6$)-cycloalkyl, aryl, substituted aryl or

where V is oxygen or sulfur, and $R^{20}$ is a branched or straight-chain, saturated or unsaturated ($C_1$–$C_{20}$)-hydrocarbon radical, aryl, substituted aryl, heterocyclyl, substituted heterocyclyl, ($C_3$–$C_6$)-cycloalkyl, ($C_3$–$C_6$)-cycloalkenyl and where in the ($C_1$–$C_{20}$)-hydrocarbon radicals mentioned under $R^6$ one or more, preferably up to three, nonadjacent $CH_2$ groups may be replaced by a carbonyl group or by hetero atom radicals such as O, S(O)y, where y=0, 1 or 2, $NR^{10"}$ or $SiR^{13"}R^{14"}$, where $R^{10"}$, $R^{13"}$ and $R^{14"}$ have the meaning of $R^{10}$, $R^{13}$ and $R^{14}$, and where additionally 3 to 6 carbon atoms of these hydrocarbon radicals may form a cycle and where these hydrocarbon radicals with or without the abovementioned variations may be substituted by one or more, preferably up to three (in the case of fluorine up to the maximum number), identical or different radicals selected from the group consisting of hydroxyl, ($C_1$–$C_4$)-alkyl, halogen, ($C_1$–$C_4$)-haloalkyl, ($C_3$–$C_6$)-cycloalkyl, ($C_1$–$C_4$)-acyl, phenoxy, substituted phenoxy, phenyl, substituted phenyl, phenylthio, substituted phenylthio and $NR^{21}R^{22}$, where $R^{21}$ and $R^{22}$ independently of each other are each hydrogen, ($C_1$–$C_4$)-alkyl, ($C_2$–$C_4$)-alkenyl, ($C_1$–$C_4$)-acyl, aryl, substituted aryl, heteroaryl or benzoyl; or if, E is $NR^{19}$ and $R^6$ is

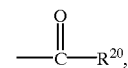

$R^{19}$ and $R^{20}$ together may also be ($C_3$–$C_6$)-alkylene where a $CH_2$ group adjacent to the nitrogen may be replaced by CO and/or where a $CH_2CH_2$ group may be replaced by a group CH=CH or o-pheylene, preferably ($C_3$–$C_6$)-alkylene, —CO—$CH_2$—$CH_2$—, —CO—CH=CH— or

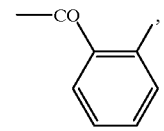

furthermore b) $R^4$ is hydrogen, halogen or ($C_1$–$C_4$)-alkyl, $R^5$ is hydrogen, halogen, a branched or straight-chain, saturated or unsaturated ($C_1$–$C_{20}$)-hydrocarbon radical, ($C_3$–$C_6$)-cycloalkyl, aryl or substituted aryl, E is

where V' is oxygen, sulfur or $NR^{23}$ and $R^{23}$ is aryl, substituted aryl, heteroaryl, substituted heteroaryl, hydroxyl, $(C_1-C_4)$-alkoxy, aryloxy, substituted aryloxy, heteroaryloxy, substituted heteroaryloxy or mono- or disubstituted amino and $R^6$ is a branched or straight-chain, saturated or unsaturated $(C_1-C_{20})$-hydrocarbon, respectively substituted or unsubstituted aryl or heteroaryl or $(C_3-C_8)$-cycloalkyl; and the abovementioned aryl and heteroaryl radicals may be substituted by one or more, preferably up to three (in the case of fluorine up to the maximum number), identical or different radicals $QR^q$, where Q is a direct bond, $NR^{24}$, O, $S(O)_s$, where s=0, 1 or 2, $OSO_2$, $SO_2O$, $NR^{25}SO_2$, $SO_2NR^{26}$, $SiR^{27}R^{28}$ or

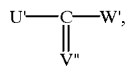

where
$R^{27}$ and $R^{28}$ are $(C_1-C_4)$-alkyl or phenyl, preferably methyl;
U' is a direct bond, $NR^{29}$ or O;
V'' is oxygen or sulfur, preferably oxygen;
W' is a direct bond, $NR^{30}$ or oxygen, where $R^{24}$, $R^{25}$, $R^{26}$, $R^{29}$ and $R^{30}$ are identical or different and are each hydrogen, $(C_1-C_4)$-alkyl, $(C_1-C_4)$-alkoxy, $(C_1-C_4)$-alkanoyl or $(C_3-C_6)$-cycloalkyl;
$R^q$ are substituents which are independent of one another and are each halogen, hydroxyl, cyano, nitro, a branched or straight-chain, saturated or unsaturated $(C_1-C_{20})$-hydrocarbon radical, $(C_3-C_8)$-cycloalkyl or $(C_4-C_8)$-cycloalkenyl, where in the 3 last radicals one or more, preferably up to three, nonadjacent saturated carbon units may be replaced by a carbonyl group or by hetero atom units such as oxygen, $S(O)_x$, where x=0, 1 or 2, $NR^{31}$ or $SiR^{32}R^{33}$ and where these last 3 radicals with or without the variations mentioned may be substituted by one or more, preferably up to three (in the case of fluorine up to the maximum number), identical or different radicals $T^1R^{34}$, or
$R^q$ is aryl or heterocyclyl, where these two radicals may be unsubstituted or substituted by up to three (in the case of fluorine even up to the maximum number) identical or different radicals $T^2R^{35}$, or two adjacent radicals $QR^q$ together with the carbon atoms that they are attached to may form a fused cycle having 4 to 6 ring atoms which is carbocyclic or contains hetero ring atoms selected from the group consisting of O, S and N and which is unsubstituted or substituted by one or more radicals selected from the group consisting of halogen, $(C_1-C_4)$-alkyl and oxo, or
$R^{24}$, $R^{26}$ and $R^{28}$ independently of one another may form with the $R^q$ located at Q a 4- to 8-membered ring system in which one or two $CH_2$ groups, preferably one $CH_2$ group, may be replaced by hetero atom units such as oxygen, $S(O)_t$, where t=0,1 or 2, or $NR^{36}$,
where
$R^{31}$ is hydrogen, $(C_1-C_4)$-alkyl, $(C_1-C_4)$-alkoxy or $(C_1-C_4)$-alkanoyl;
$R^{32}$ and $R^{33}$ independently of one another are each $(C_1-C_4)$-alkyl, preferably methyl;
$T^1$ and $T^2$ are in each case independent of the other and are each a direct bond, oxygen, $S(O)_k$, $SO_2O$, $OSO_2$, CO, OCO, COO, $NR^{37}$, $SO_2NR^{37}$, $NR^{37}SO_2$, $ONR^{37}$, $NR^{37}O$, $NR^{37}CO$, $CONR^{37}$ or $SiR^{38}R^{39}$ and k=0, 1 or 2, where
$R^{37}$ independently of the others is hydrogen, $(C_1-C_4)$-alkyl, $(C_1-C_4)$-alkanoyl or $(C_3-C_5)$-cycloalkyl;
$R^{38}$ and $R^{39}$ independently of one another are each $(C_1-C_4)$-alkyl;
$R^{34}$ and $R^{35}$ independently of one another are each hydrogen, cyano, nitro, halogen, $(C_1-C_8)$-alkyl, $(C_1-C_8)$-haloalkyl, $(C_2-C_8)$-alkenyl, $(C_2-C_8)$-haloalkenyl, $(C_2-C_8)$-alkynyl, $(C_2-C_8)$-haloalkynyl, $(C_1-C_8)$-alkoxy-$(C_1-C_4)$-alkyl, $(C_1-C_8)$-haloalkoxy-$(C_1-C_4)$-alkyl, $(C_1-C_8)$-alkylthio-$(C_1-C_4)$-alkyl, $(C_1-C_8)$-haloalkylthio-$(C_1-C_4)$-alkyl, $(C_3-C_8)$-cycloalkyl, $(C_4-C_8)$-cycloalkenyl, $(C_3-C_8)$-cycloalkyl-$(C_1-C_4)$-alkyl, $(C_4-C_8)$-cycloalkenyl-$(C_1-C_4)$-alkyl, aryl, heterocyclyl, aryl-$(C_1-C_4)$-alkyl or heterocyclyl-$(C_1-C_4)$-alkyl, where in these last 8 radicals the cycloaliphatic, aromatic or heterocyclic ring systems may be unsubstituted or substituted by up to three (in the case of fluorine even up to the maximum number) identical or different substituents $R^{40}$, or
$R^{34}$ and $R^{35}$, located at the same carbon atom, together are an oxo group,
where
$R^{40}$ is $(C_1-C_4)$-alkyl, $(C_1-C_4)$-haloalkyl, $(C_1-C_4)$-alkoxy, $(C_1-C_4)$-haloalkoxy, cyano, nitro or halogen;
$R^{36}$ is hydrogen, $(C_1-C_8)$-alkyl, $(C_1-C_4)$-haloalkyl, $(C_1-C_4)$-alkoxy, $(C_1-C_4)$-alkylthio, $(C_3-C_5)$-cycloalkyl, $(C_2-C_4)$-alkenyl, $(C_2-C_4)$-alkynyl, $(C_1-C_4)$-alkanoyl, $(C_2-C_4)$-haloalkanoyl, $(C_2-C_4)$-alkoxyalkyl, phenyl-$(C_1-C_4)$-alkyl or phenyl and the phenyl groups are unsubstituted or substituted by up to three (in the case of fluorine even up to the maximum number) identical or different substituents $R^{41}$, where
$R^{41}$ is $(C_1-C_4)$-alkyl, $(C_1-C_4)$-haloalkyl, $(C_1-C_4)$-alkoxy, $(C_1-C_4)$-alkylthio, halogen or cyano;
and $(C_1-C_{20})$-hydrocarbon radicals mentioned under a) and b) under $R^4$, $R^5$ and $R^6$, unless defined otherwise, one or more, preferably up to three, nonadjacent $CH_2$ groups may be replaced by a carbonyl group or by hetero atom radicals such as $S(O)y$, where y=0, 1 or 2, $NR^{10'''}$ or $SiR^{13'''}R^{14'''}$, where $R^{10'''}$, $R^{13'''}$ and $R^{14'''}$ have the meaning of $R^{10}$, $R^{13}$ and $R^{14}$, and where additionally 3 to 6 carbon atoms of these hydrocarbon radicals may form a cycle, and where these hydrocarbon radicals with or without the abovementioned variations may be substituted by one or more, preferably up to three (in the case of fluorine up to the maximum number) identical or different radicals selected from the group consisting of halogen, ($C_3$–$C_8$)-cycloalkyl, phenoxy, substituted phenoxy, phenyl, substituted phenyl, and where furthermore the radicals of the meanings "aryl", "substituted aryl", "aryloxy", "substituted aryloxy", "heterocyclyl", "substituted heterocyclyl", "phenyl", "substituted phenyl", "phenoxy", "substituted phenoxy", "phenylthio", "substituted phenylthio", "branched or straight-chain, saturated or unsaturated ($C_1$–$C_{20}$)-hydrocarbon" listed for $R^4$, $R^5$, $R^6$ and E under a) and b), unless defined otherwise, have the meanings given above under Y Z and where furthermore in the alkyl, cycloalkyl, alkylene, alkenyl, cycloalkenyl, alkynyl, saturated or unsaturated hydrocarbon radicals or radicals derived therefrom such as, for example, alkoxy, alkylthio, alkylsulfinyl, alkylsulfonyl or alkoxycarbonyl listed for the radicals $R^4$, $R^5$, $R^6$ and E as radicals, substituents or components of ring systems, unless defined otherwise, the hydrogen atoms may be replaced partly, in the case of fluorine even wholly, by halogen, preferably chlorine or fluorine.

From among the radicals R, preference is given to those for which in the radicals mentioned under a)

$R^4$ is hydrogen, halogen or methyl;

$R^5$ is hydrogen, halogen, ($C_1$–$C_8$)-alkyl, ($C_2$–$C_8$)-alkenyl, ($C_2$–$C_8$)-alkynyl, phenyl, substituted phenyl or ($C_3$–$C_6$)-cycloalkyl;

E is oxygen, $NR^{19}$, S(O)q, where q=0, 1 or 2, $R^{19}$ being hydrogen, methyl or acetyl;

$R^6$ is ($C_1$–$C_4$)-alkyl, ($C_2$–$C_4$)-alkenyl, ($C_1$–$C_4$)-haloalkyl, ($C_3$–$C_6$)-cycloalkyl, phenyl or

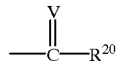

where V is oxygen or sulfur and $R^{20}$ is ($C_1$–$C_8$)-alkyl, ($C_2$–$C_8$)-alkenyl, ($C_2$–$C_8$)-alkynyl, aryl, substituted aryl, heterocyclyl, substituted heterocyclyl, ($C_1$–$C_8$)-haloalkyl, ($C_2$–$C_8$)-haloalkenyl, ($C_2$–$C_8$)-haloalkynyl, ($C_3$–$C_6$)-cycloalkyl, ($C_3$–$C_6$)-halocycloalkyl, ($C_5$–$C_6$)-cycloalkenyl, ($C_5$–$C_6$)-halocycloalkenyl and the hydrocarbon radicals mentioned may be substituted by one or more, preferably up to three, identical or different radicals selected from the group consisting of alkyl, haloalkyl, cycloalkyl, phenoxy, substituted phenoxy, phenyl, substituted phenyl and $NR^{21}R^{22}$, and $R^{21}$ and $R^{22}$ independently of one another are each hydrogen, ($C_1$–$C_8$)-alkyl, ($C_2$–$C_8$)-alkenyl, ($C_1$–$C_8$)-acyl, aryl, heteroaryl or benzoyl; or if E is $NR^{19}$ and $R^6$ is

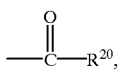

$R^{19}$ and $R^{20}$ together may also be ($C_3$–$C_6$)-alkylene, where a $CH_2$ group adjacent to the nitrogen may be replaced by CO and/or a $CH_2$—$CH_2$ group may be replaced by a group CH=CH or o-phenylene, preferably ($C_3$–$C_6$)-alkylene, —CO—$CH_2$—$CH_2$—, —CO—CH=CH— or

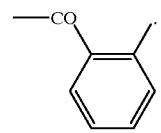

Of these, most preferred are those compounds of the formula I in which $R^4$ is hydrogen;

$R^5$ is hydrogen or ($C_1$–$C_8$)-alkyl;

E is oxygen and NH; and $R^6$ is

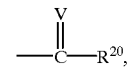

where V is oxygen, and furthermore, from among the radicals R, preference is given to those for which in the radicals mentioned under b)

$R^4$ is hydrogen;

$R^5$ is hydrogen, halogen, ($C_1$–$C_8$)-alkyl, ($C_1$–$C_8$)-haloalkyl, ($C_2$–$C_8$)-alkenyl, ($C_2$–$C_8$)-alkynyl;

E is

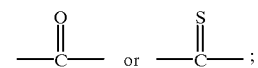

$R^6$ is aryl or heteroaryl, where the aryl and heteroaryl radicals may be substituted by one or more, preferably up to three (in the case of halogen up to the maximum number), identical or different radicals $QR^q$, where Q is a direct bond, O, $OSO_2$ or

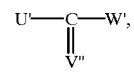

where

U' is a direct bond, or is O;

V" is oxygen;

W' is a direct bond, $NR^{30}$ or oxygen; and $R^{30}$ is hydrogen, ($C_1$–$C_4$)-alkyl, ($C_1$–$C_4$)-alkoxy, ($C_1$–$C_4$)-alkanoyl or ($C_3$–$C_5$)-cycloalkyl;

$R^q$ are substituents which are independent of one another and which are each ($C_1$–$C_{20}$)-alkyl or ($C_2$–$C_{20}$)-alkenyl and which may be substituted by one or more, preferably up to three (in the case of fluorine up to the maximum number) identical or different radicals $T^1R^{34}$, or $R^q$ is halogen, hydroxyl, nitro or cyano or $R^q$ is aryl or heterocyclyl, where these two radicals may be unsubstituted or substituted by up to three (in the case of fluorine even up to the maximum number) identical or different radicals $T^2R^{35}$;

$T^1$ and $T^2$ are independent of one another and are each a direct bond, —O—, —S(O)$_k$—, —$SO_2O$—, —$OSO_2$—, —CO—, —OCO—, —COO—, —$NR^{37}$—, —$SO_2NR^{37}$—, —$NR^{37}SO_2$—, —$ONR^{37}$—, —$NR^{37}O$—, —$NR^{37}CO$—, —$CONR^{37}$—, and k=0, 1 or 2, and where $R^{37}$ independently of the others is hydrogen, $(C_1-C_4)$-alkyl, $(C_1-C_4)$-alkanoyl or $(C_3-C_5)$-cycloalkyl;

$R^{34}$ and $R^{35}$ independently of one another are each hydrogen, halogen, preferably fluorine, $(C_1-C_8)$-alkyl, $(C_3-C_8)$-cycloalkyl, aryl or heterocyclyl, where in the last 3 radicals the cycloaliphatic, aromatic or heterocyclic ring systems may be unsubstituted or substituted by up to three (in the case of fluorine even up to the maximum number) identical or different substituents $R^{40}$, where $R^{40}$ independently of the others is $(C_1-C_4)$-alkyl, $(C_1-C_4)$-haloalkyl, $(C_1-C_4)$-alkoxy, $(C_1-C_4)$-haloalkoxy, cyano, nitro, halogen.

Of these, most preference is given to those compounds of the formula I in which $R^4$ is hydrogen $R^5$ is hydrogen or methyl E is

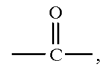

$R^6$ is aryl or heteroaryl, where the aryl and heteroaryl radicals may be substituted by one or more, preferably up to three (in the case of halogen up to the maximum number) identical or different radicals $QR^q$, where Q is a direct bond, O or

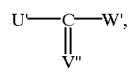

where

U' is a direct bond, or O;

V" is oxygen;

W' is a direct bond, $NR^{30}$ or oxygen; and $R^{30}$ is hydrogen, $(C_1-C_4)$-alkyl, $(C_1-C_4)$-alkoxy, $(C_1-C_4)$-alkanoyl or $(C_3-C_5)$-cycloalkyl;

$R^q$ are substituents which are independent of one another and which are each $(C_1-C_{12})$-alkyl or $(C_2-C_{12})$-alkenyl and which may be substituted by one or more, preferably up to three (in the case of fluorine up to the maximum number) identical or different radicals $R^{34}$, or $R^q$ is halogen, nitro or cyano, or $R^q$ is aryl or heterocyclyl, where these two radicals may be unsubstituted or substituted by up to three (in the case of fluorine up even to the maximum number) identical or different radicals $T^2R^{35}$;

$T^2$ are in each case independent of one another and are each a direct bond, —O—, —S(O)$_k$—, —SO$_2$O—, —OSO$_2$—, —CO—, —OCO—, —COO—, —NR$^{37}$—, —SO$_2$NR$^{37}$—, —NR$^{37}$SO$_2$—, —ONR$^{37}$—, —NR$^{37}$O—, —NR$^{37}$CO—, —CONR$^{37}$—, and k=0, 1 or 2, and where $R^{37}$ independently of the others is hydrogen, $(C_1-C_4)$-alkyl, $(C_1-C_4)$-alkanoyl or $(C_3-C_5)$-cycloalkyl;

$R^{34}$ and $R^{35}$ independently of one another are each hydrogen, halogen, preferably fluorine, $(C_1-C_8)$-alkyl, $(C_3-C_8)$-cycloalkyl, aryl or heterocyclyl, where the last 3 radicals the cycloaliphatic, aromatic or heterocyclic ring systems may be unsubstituted or substituted by up to three (in the case of fluorine even up to the maximum number) identical or different substituents $R^{40}$, where $R^{40}$ independently of the others may be $(C_1-C_4)$-alkyl, $(C_1-C_4)$-haloalkyl, $(C_1-C_4)$-alkoxy, $(C_1-C_4)$-haloalkoxy, cyano, nitro, halogen.

Preferred anions are those for which $Q^{n-}$ is Hal$^-$, NO$_3^-$, BF$_4^-$, BPh$_4^-$ or PF$_6^-$.

Preferred radicals Y Z are those:

from among the radicals described under a) for which $R^7$ is hydrogen, $(C_1-C_4)$-alkyl or cyclopropyl, in particular those for which $R^7$ is hydrogen, methyl, ethyl or cyclopropyl and Z is a branched or, preferably, straight-chain $(C_5-C_{12})$-alkyl radical;

from among the radicals described under b) for which ba) Y is a group CH(CH$_3$), CH(C$_2$H$_5$) or

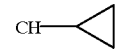

and

Z is a phenyl group substituted in position 4 or bb) Y is a $(C_2-C_4)$-alkylene group and Z is a phenoxy group which is mono- to trisubstituted by alkyl radicals or radicals derived therefrom which is separated from X by at least 2 carbon atoms, or bc) Y is a $(C_2-C_4)$-alkylene group and Z is a phenyl group substituted in position 4 and Z is separated from X by at least 2 carbon atoms;

from among the radicals described under c) for which

Y is a carbonyl group and

Z is a benzyl radical which is substituted in position 4 of the phenyl nucleus and A is CH.

From the radicals described under ba), more preference is given to those radicals for which Y is CHCH$_3$ and CH(C$_2$H$_5$) and Z is a phenyl group which is substituted in position 4 in each case by substituted or unsubstituted phenyl, phenoxy, pyridyloxy, pyrimidinyloxy or by $(C_1-C_4)$-alkoxy, $(C_1-C_4)$-haloalkoxy or $(C_1-C_4)$-haloalkyl.

From the radicals described under bb), more preference is given to those radicals for which Y is $(C_2-C_4)$-alkylene and Z is a phenoxy group which carries hydrogen or methyl in position 2 and 3, which carries a $(C_1-C_4)$-alkyl, $(C_1-C_4)$-alkoxy or $(C_1-C_4)$-alkoxy-$(C_1-C_4)$-alkyl radical in position 4, and which is separated from X by at least 2 carbon atoms.

From the radicals described under bc), more preference is given to those radicals for which Y is a $(C_2-C_3)$-alkylene group and Z is a phenyl group which is substituted in position 4 by $(C_1-C_8)$-alkyl, $(C_1-C_8)$-haloalkyl, $(C_1-C_8)$-alkoxy, $(C_1-C_8)$-haloalkoxy or a substituted or unsubstituted phenyl or phenoxy group, and which is separated from X by at least 2 carbon atoms.

From the radicals described under c), more preference is given to those radicals for which Y is a carbonyl group and Z is a benzyl radical which is substituted in position 4 of the phenyl nucleus by $(C_1-C_8)$-alkyl, $(C_1-C_8)$- haloalkyl, $(C_1-C_8)$-alkoxy, $(C_1-C_8)$-haloalkoxy or a substituted or unsubstituted phenyl or phenoxy group and A is CH.

With regard to the radicals and groups $R^1$, $R^2$, $R^3$, A and D, preference is given to those compounds of the formula I in which $R^1$ is hydrogen, methyl, chlorine or fluorine;

$R^2$ and $R^3$ are each hydrogen, $(C_1-C_4)$-alkyl, $(C_2-C_4)$-alkenyl, $(C_2-C_4)$-alkynyl, trimethylsilylethynyl, methoxycarbonyl, $(C_1-C_4)$-haloalkyl, halogen, $(C_1-C_4)$-alkoxy, methoxymethyl or cyano; or $R^2$ and $R^3$, together with the carbon atoms to which they are attached, form an optionally substituted unsaturated 5- or 6-membered ring which may, if it is a 5-membered ring, contain a sulfur atom instead of a $CH_2$ unit; or $R^2$ and $R^3$, together with the carbon atoms to which they are attached, form a saturated 5- or 6-membered ring which may contain a sulfur or an oxygen atom instead of a $CH_2$ unit;

X is NH;

in particular those compounds where $R^1$ is hydrogen;

$R^2$ and $R^3$ are each hydrogen, methyl, ethyl, propyl, $(C_2-C_3)$-alkenyl, $(C_2-C_3)$-chloro or -fluoroalkenyl, $(C_2-C_3)$-alkynyl, trimethylsilylethynyl, $(C_1-C_3)$-chloro- or -fluoroalkyl, methoxy, methoxymethyl, halogen or cyano;

$R^2$ and $R^3$, together with the ring system to which they are attached, form the quinazoline or quinoline system which may be substituted in the carbocyclic moiety by fluorine; or $R^2$ and $R^3$, together with the carbon atoms to which they are attached, form a saturated 6-membered ring which may contain an oxygen or sulfur atom instead of a $CH_2$ group.

Particular preference is given to those compounds of the formula I where $R^1$ is hydrogen;

$R^2$ is methyl, ethyl, propyl, isopropyl, $(C_1-C_2)$-fluoroalkyl or methoxymethyl;

$R^3$ is fluorine, chlorine, bromine, cyano, vinyl, ethynyl or methoxy; or $R^2$ and $R^3$, together with the ring system to which they are attached, form the quinazoline system which may be substituted by a fluorine atom;

A and D, in the case where Y Z have the meanings given under a) and b), describe the pyrimidine system and, in the case where Y Z has the meanings given under c), describe the pyridine system;

X is NH;

and specifically those compounds of the formula I in which $R^1$ is hydrogen;

$R^2$ is ethyl or methoxymethyl;

$R^3$ is chlorine, bromine or methoxy, preferably those for which $R^2$ is ethyl and $R^3$ is bromine or chlorine or $R^2$ is methoxymethyl and $R^3$ is methoxy;

X is NH.

Some of the compounds of the formula I have one or more asymmetric carbon atoms or stereoisomers on double bonds. Enantiomers or diastereomers may therefore occur. The invention embraces both the pure isomers and mixtures thereof. The mixtures of diastereomers can be separated into the components by customary methods, for example by selective crystallization from appropriate solvents or by chromatography. Racemates can be resolved into the enantiomers by customary methods, for example by forming a salt with an optically active acid, separating the diastereomeric salts and liberating the pure enantiomers by means of a base.

The invention additionally relates to a process for the preparation of compounds of the formula I, which comprises reacting a compound of the formula (II)

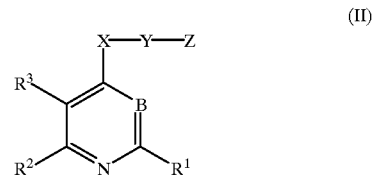

where B is CH or N and $R^1$, $R^2$, $R^3$, X, Y and Z are each as defined under formula I, with an electrophil of the formula (III),

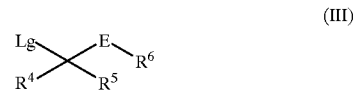

where $R^4$, $R^5$, $R^6$ and E are each as defined under formula I and Lg is a leaving group, for example halogen, alkylthio, alkanesulfonyloxy or arylsulfonyloxy, alkylsulfonyl or arylsulfonyl, preferably halogen, if appropriate with the addition of salts such as, for example, $AgBF_4$, $AgNO_3$ or NaI, and, if appropriate, replacing the anion of compounds obtained in this manner with other anions similarly to known methods [for example Liebigs Ann. Chem. 1978, 1937; Methoden der Org. Chemie/Houben-Weyl (D. Klamann, Ed.), 4th edition, Vol. E16a, Part 2, p. 1008 ff, Thieme, Stuttgart 1990].

The above-described substitution reaction is known in principle [for example Methoden der Org. Chemie/Houben-Weyl (D. Klamann, Ed.), 4th edition, Vol. E16a, Part 2, p 997 ff, Thieme, Stuttgart 1990, Liebigs Ann. Chem. 621 (1959) 106; Arch. Pharm. (Weinheim) 328 (1995) 531].

The structures (II) and (III) can be varied within wide limits.

The abovementioned reaction is carried out in a temperature range from 20 to 150° C., if appropriate in an inert organic solvent such as acetonitrile, acetone, 2-butanone, N,N-dimethylformamide, N,N-dimethylacetamide, dimethyl sulfoxide, N-methylpyrrolidin-2-one, dioxane, tetrahydrofuran, 4-methyl-2-pentanone, methanol, ethanol, butanol, ethylene glycol, ethylene glycol dimethyl ether, toluene, chlorobenzene or xylene. Mixtures of the solvents mentioned can also be used.

Most of the compounds of the formula (II) required as starting materials are known from the literature [for example EP-A-57 440, EP-A-196 524, EP-A-264 217, EP-A-326 329, EP-A-323 757, EP-A-432 894, DE-A-116 089, WO 93/04 580], or they can be prepared similarly to known methods.

Compounds of the formula (III) are commercially available or can be obtained by processes known in principle [for example Verne, De Kimpe, "The Chemistry of Functional Groups, Supplement D", (Patai, Rappaport, Eds.), Part 1, p. 813 ff, Wiley, New York, 1983; Acta Chem. Scand. 20 (1966)1273; Chem. Ber. 92 (1959) 1599; J. Am. Chem. Soc.

95 (1973) 7813; Zh. Obshch. Khim, 28 (1958)1930; J. Am. Chem. Soc. 43 (1921) 660].

While being tolerated well by plants and having favorable toxicity toward warm-blooded animals, the active substances are suitable for controlling animal pests, especially insects, arachnids, helminths and molluscs, and very preferably for controlling insects and arachnids, which are encountered in agriculture, in animal breeding, in forestry, in the protection of stored products and materials, and in the hygiene sector. They are active against normally sensitive and resistant species and against all or certain stages of development. The abovementioned pests include:

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp., Eotetranychus spp., Oligonychus spp. and Eutetranychus spp.

From the order of the Isopoda, for example, *Oniscus asellus, Armadillidium vulgare* and *Porcellio scaber*.

From the order of the Diplopoda, for example, *Blaniulus guttulatus*.

From the order of the Chilopoda, for example, *Geophilus carpophagus* and Scutigera spp.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis, Periplaneta americana, Leucophaea madeirae, Blattella germanica, Acheta domesticus*, Gryllotalpa spp., *Locusta migratoria migratorioides, Melanoplus differentialis* and *Schistocerca gregaria*.

From the order of the Isoptera, for example, Reticulitermes spp.

From the order of the Anoplura, for example, *Phylloera vastatrix*, Pemphigus spp., *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis, Thrips tabaci* and Frankliniella spp.

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum*, Aphis spp., *Brevicoryne brassicae, Cryptomyzus ribis, Doralis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelus bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Laphygma exigua, Mamestra brassicae, Panolis flammea, Prodenia litura,* Spodoptera spp., *Trichoplusia ni, Carpocapsa pomonella*, Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima, Tortrix viridana*, Cuaphalocrocis spp. and Manduca spp.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylloides chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethese aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis, Costelytra zealandica* and Lissorhoptus spp.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopsis* and Ceratophyllus spp.

From the order of the Arachnida, for example, *Scorpio maurus* and *Latrodectus mactans*.

From the class of the helminths, for example, Haemonchus, Trichostrongulus, Ostertagia, Cooperia, Chabertia, Strongyloides, Oesophagostomum, Hyostrongulus, Ancylostoma, Ascaris and Heterakis and also Fasciola.

From the class of the Gastropoda, for example, Deroceras spp., Arion spp., Lymnaea spp., Galba spp., Succinea spp., Biomphalaria spp., Bulinus spp. and Oncomelania spp.

From the class of the Bivalva, for example, Dreissena spp.

The plant-parasitic nematodes which can be controlled in accordance with the invention include, for example, the root-parasitic soil nematodes such as, for example, those of the genera Meloidogyne (root gall nematodes, such as *Meloidogyne incognita, Meloidogyne hapla* and *Meloidogyne javanica*), Heterodera and Globodera (cyst-forming nematodes, such as *Globodera rostochiensis, Globodera pallida, Heterodera trifolii*) and of the genera Radopholus, such as *Radopholus similis*, Pratylenchus, such as *Pratylenchus neglectus, Pratylenchus penetrans* and *Pratylenchus curvitatus*, Tylenchulus, such as *Tylenchulus semipenetrans*, Tylenchorhynchus, such as *Tylenchorhynchus dubius* and *Tylenchorhynchus claytoni*, Rotylenchus, such as *Rotylenchus robustus*, Helicotylenchus, such as *Helicotylenchus multicinctus*, Belonoaimus, such as *Belonoaimus longicaudatus*, Longidorus, such as *Longidorus elongatus*, Trichodorus, such as *Trichodorus primitivus*, and Xiphinema, such as *Xiphinema index*.

The compounds according to the invention can also be used to control the nematode genera Ditylenchus (stem parasites, such as *Ditylenchus dipsaci* and Ditylenchus destructor), Aphelenchoides (leaf nematodes, such as *Aphelenchoides ritzemabosi*) and Anguina (leaf-gall nematodes, such as *Anguina tritici*).

The invention also relates to compositions, especially insecticidal and acaricidal compositions, which comprise the compounds of the formula I in addition to suitable formulation auxiliaries.

The compositions according to the invention comprise the active substances of the formula I in general in a proportion of from 1 to 95% by weight.

They can be formulated in various ways depending on the biological and/or chemicophysical parameters which prevail. Possible formulations which are suitable are therefore: wettable powders (WP), emulsifiable concentrates (EC), aqueous solutions (SL), emulsions, sprayable solutions, oil- or water-based dispersions (SC), suspoemulsions (SE), dusts (DP), seed-dressing products, granules in the form of microgranules, spray granules, coated granules and adsorption granules, water-dispersible granules (WG), ULV formulations, microcapsules, waxes or baits.

These individual types of formulation are known in principle and are described, for example, in: Winnacker-Küchler, "Chemische Technologie", Volume 7, C. Hauser Verlag Munich, 4th ed. 1986; van Falkenberg, "Pesticides Formulations", Marcel Dekker N.Y., 2nd ed. 1972–73; K. Martens, "Spray Drying Handbook", 3rd ed. 1979, G. Goodwin Ltd. London.

The formulation auxiliaries required, such as inert materials, surfactants, solvents and other additives, are likewise known and are described, for example, in: Watkins, "Handbook of Insecticide Dust Diluents and Carriers", 2nd ed., Darland Books, Caldwell N.J.; H. v. Olphen, "Introduction to Clay Colloid Chemistry", 2nd ed., J. Wiley & Sons, N.Y.; Marsden, "Solvents Guide", 2nd ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte", Wiss.Verlagsgesell., Stuttgart 1967; Winnacker-Küchler, "Chemische Technologie", Volume 7, C. Hauser Verlag Munich, 4th ed. 1986.

Based on these formulations, it is also possible to produce combinations with other pesticidally active substances, fertilizers and/or growth regulators, for example in the form of a readymix or a tank mix. Wettable powders are preparations, uniformly dispersible in water, which contain, beside the active substance and in addition to a diluent or inert material, wetting agents, for example polyoxethylated alkylphenols, polyoxethylated fatty alcohols, alkyl- or alkylphenolsulfonates, and dispersing agents, for example sodium ligninsulfonate or sodium 2,2'-dinaphthylmethane-6,6'-disulfonate.

Emulsifiable concentrates are prepared by dissolving the active substance in an organic solvent, for example butanol, cyclohexanone, dimethylformamide, xylene or higher-boiling aromatics or hydrocarbons, with addition of one or more emulsifiers. As emulsifiers, the following can be used, for example: calcium salts of alkylaryl-sulfonates, such as Ca dodecylbenzenesulfonate, or nonionic emulsifiers such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or poly-oxethylene sorbitol esters.

Dusting agents are obtained by grinding the active substance with finely divided solid substances, for example talc, natural clays such as kaolin, bentonite, pyrophillite or diatomaceous earth. Granules can be prepared either by atomizing the active substance onto adsorptive, granulated inert material or by applying active substance concentrates onto the surface of carrier materials such as sand or kaolinites, or of granulated inert material, by means of adhesives, for example poly-vinyl alcohol or sodium polyacrylate, or alternatively mineral oils. Suitable active substances can also be granulated in the fashion conventional for the preparation of fertilizer granules, if desired as a mixture with fertilizers.

In wettable powders, the concentration of active substance is, for example, from approximately 10 to 90% by weight, the remainder to 100% by weight being composed of customary formulation components. In the case of emulsifiable concentrates, the concentration of active substance may be from approximately 5 to 80% by weight. Formulations in dust form comprise in most cases from 5 to 20% by weight of active substance, sprayable solutions from about 2 to 20% by weight. In the case of granules, the content of active substance depends partly on whether the active compound is in liquid or solid form and on which granulation auxiliaries, fillers, etc. are being used.

In addition, the abovementioned formulations of active substance comprise, if appropriate, the adhesives, wetting agents, dispersants, emulsifiers, penetrants, solvents, fillers or carriers which are customary in each case.

The concentrates, which are in the commercially customary form, are if appropriate diluted in the customary manner for their use, for example using water in the case of wettable powders, emulsifiable concentrates, dispersions and some microgranules. Dust and granule preparations, and also sprayable solutions, are normally not diluted any further with other inert substances before being used.

The application rate required varies with the external conditions, such as temperature and humidity among others. It can fluctuate within wide limits, for example between 0.0005 and 10.0 kg/ha or more of active substance, but is preferably between 0.001 and 5 kg/ha.

The active substances according to the invention may be present in their commercially customary formulations, and in the application forms prepared from these formulations, as mixtures with other active substances, such as insecticides, attractants, sterilants, acaricides, nematicides, fungicides, growth regulators or herbicides.

The pesticides include, for example, phosphates, carbamates, carboxylates, formamidines, tin compounds and substances produced by microorganisms, inter alia.

Preferred mixture components are 1. from the group of the phosphorus compounds acephate, azamethiphos, azinphos-ethyl, azinphos-methyl, bromophos, bromophos-ethyl, chlorfenvinphos, chlormephos, chlorpyrifos, chlorpyrifos-methyl, demeton, demeton-S-methyl, demeton-S-methylsulphone, dialifos, diazinon, dichlorvos, dicrotophos, O,O-1,2,2,2-tetrachloroethyl phosphorothioate (SD 208 304), dimethoate, disulfoton, EPN, ethion, ethoprophos, etrimfos, famphur, fenamiphos, fenitriothion, fensulfothion, fenthion, fonofos, formothion, heptenophos, isozophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosmet, phosphamidon, phoxim, pirimiphos, pirimiphos-ethyl, pirimiphos-methyl, profenofos, propaphos, proetamphos, prothiofos, pyraclofos, pyridapenthion, quinalphos, sulprofos, temephos, terbufos, tetraclorvinphos, thiometon, triazophos, trichlorfon, vamidothion;

2. from the group of the carbamates
   aldicarb, 2-sec-butylphenyl methylcarbamate (BPMC), carbaryl, carbofuran, carbosulfan, cloethocarb, benfuracarb, ethiofencarb, furathiocarb, isoprocarb, methomyl, 5-methyl-m-cumenylbutyryl (methyl) carbamate, oxamyl, pirimicarb, propoxur, thiodicarb, thiofanox, ethyl 4,6,9-triaza-4-benzyl-6,10-dimethyl-8-oxa-7-oxo-5,11-dithia-9-dodecenoate (OK 135), 1-methylthio(ethylideneamino)-N-methyl-N-(morpholinothio)carbamate (UC 51717);
3. from the group of the carboxylates
   allethrin, alphametrin, 5-benzyl-3-furylmethyl (E)-(1R) cis-2,2-dimethyl-3-(2-oxothiolan-3-ylidenemethyl)cyclopropanecarboxylate, bioallethrin, bioallethrin ((S)-cyclopentyl isomer), bioresmethrin, biphenate, (RS)-1-cyano-1-(6-phenoxy-2-pyridyl)methyl (1RS)-trans-3-(4-tert-butylphenyl)-2,2-dimethylcyclopropane-carboxylate (NCI 85193), cycloprothrin, cyhalothrin, cythithrin, cypermethrin, cyphenothrin, deltamethrin, empenthrin, esfenvalerate, fenfluthrin, fenpropathrin, fenvalerate, flucythrinate, flumethrin, fluvalinate (D-isomers), permethrin, phenothrin ((R)-isomers), d-prallethrin, pyrethrins (natural products), resmethrin, tefluthrin, tetramethrin, tralomethrin;
4. from the group of the amidines
   amitraz, chlordimeform;
5. from the group of the tin compounds
   cyhexatin, fenbutatin oxide;
6. others
   abamectin, *Bacillus thuringiensis*, bensultap, binapacryl, bromopropylate, buprofezin, camphechlor, cartap, chlorobenzilate, chlorfluazuron, 2-(4-chlorophenyl)-4,5-diphenylthiophene (UBI-T 930), clorfentezine, 2-naphthylmethyl cyclopropanecarboxylate (Ro 12-0470), cyromazin, ethyl N-(3,5-dichloro-4-(1,1,2,3,3,3-hexafluoro-1-propyloxy)phenyl)carbamoyl)-2-chlorobenzocarboximidate, DDT, dicofol, N-(N-(3,5-dichloro4-(1,1,2,2-tetrafluoroethoxy) phenylamino)carbonyl)-2,6-difluorobenzamide (XRD 473), diflubenzuron, N-(2,3-dihydro-3-methyl-1,3-thiazol-2-ylidene)2,4-xylidine, dinobuton, dinocap, endosulfan, ethofenprox, (4-ethoxyphenyl)(dimethyl)(3-(3-phenoxyphenyl) propyl)silane, (4-ethoxy-phenyl)(3-(4-fluoro-3-phenoxyphenyl)propyl)dimethylsilane, fenoxycarb, 2-fluoro-5-(4-(4-ethoxyphenyl)-4-methyl-1-pentyl) diphenyl ether (MTI 800), granulosis and nuclear polyhedrosis viruses, fenthiocarb, flubenzimine, flucycloxuron, flufenoxuron, gamma-HCH, hexythiazox, hydramethyinon (AC 217300), ivermectin, 2-nitromethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam, trifumuron and imidacloprid.

The active substance content of the use forms prepared from the commercially customary formulations can be from 0.00000001 to 95% by weight of active substance, preferably between 0.00001 and 1% by weight.

Application is effected in a conventional fashion, matched to the use forms.

The active substances according to the invention are also suitable for controlling ecto- and endoparasites in the veterinary sector or in the sector of animal husbandry.

The active substances according to the invention are in this case administered in a known fashion, such as by oral administration in the form of, for example, tablets, capsules, potions or granules, by dermal administration in the form of, for example, dipping, spraying, pouring-on and spotting-on and powdering, and also by parenteral administration in the form of, for example, injection.

The novel compounds, according to the invention, of the formula I can accordingly also be employed particularly advantageously in livestock husbandry (for example cattle, sheep, pigs and poultry such as chickens, geese etc.). In a preferred embodiment of the invention, the novel compounds, if appropriate in suitable formulations (cf. above) and if appropriate with the drinking water or feed, are administered orally to the animals. Since excretion in the droppings occurs in an effective fashion, the development of insects in the animal droppings can be prevented very simply in this fashion. The dosages and formulations suitable in each case are particularly dependent on the type and stage of development of the productive animals and also on the degree of infestation, and can easily be determined and fixed by conventional methods. In the case of cattle, the novel compounds can be employed, for example, in dosages of 0.01 to 1 mg/kg of body weight.

The compounds of the formula I according to the invention also have an outstanding fungicidal action. Fungal pathogens which have already penetrated the plant tissue can be successfully subjected to curative control. This is particularly important and advantageous in the case of those fungal diseases which can no longer be controlled effectively with the otherwise customary fungicides when infection has taken place already. The spectrum of action of the claimed compounds embraces various economically important phytopathogenic fungi, for example *Plasmopara viticola, Phytophthora infestans, Erysiphe graminis, Pyricularia oryzae, Pyrenophora teres, Leptosphaeria nodorum, Pellicularia sasakii* and *Puccinia recondite*.

In addition, the compounds according to the invention are also suitable for use in technical fields, for example as wood preservatives, as preservatives in paints, in cooling lubricants for metalworking, or as preservatives in drilling and cutting oils.

The active substances according to the invention in their commercially customary formulations can be employed either alone or in combination with other fungicides known from the literature.

Examples of fungicides which are known from the literature and which can be combined, in accordance with the invention, with the compounds of the formula I are the following products:

aldimorph, andoprim, anilazine, BAS 480F, BAS 450F, BAS 490F, benalaxyl, benodanil, benomyl, binapacryl, bitertanol, bromuconazole, buthiobate, captafol, captan, carbendazim, carboxin, CGA 173506, cyprodinil, cyprofuram, dichlofluanid, dichlomezin, diclobutrazol, diethofencarb, difenconazol (CGA 169374), difluconazole, dimethirimol, dimethomorph, diniconazole, dinocap, dithianon, dodemorph, dodine, edifenfos, ethirimol, etridiazole, epoxiconazole, fenbuconazole, fenarimol, fenfuram, fenpiclonil, fenpropidin, fenpropimorph, fentin acetate, fentin hydroxide, ferimzone (TF164), fluazinam, fluobenzimine, fludioxinil, fluquinconazole, fluorimide, flusilazole, flutolanil, flutriafol, folpet, fosetylaluminium, fuberidazole, fulsulfamide (MT-F 651), furalaxyl, furconazole, furmecyclox, guazatine, hexaconazole, ICI A5504, imazalil, imibenconazole, iprobenfos, iprodione, isoprothiolane, KNF 317, copper compounds, such as Cu oxychloride, oxine-Cu, Cu oxide, mancozeb, maneb, mepanipyrim (KIF 3535), metconazole, mepronil, metalaxyl, methasulfocarb, methfuroxam, MON 24000, myclobutanil, nabam, nitrothalidopropyl, nuarimol, ofurace, oxadixyl, oxycarboxin, penconazole, pencycuron, PP 969, probenazole, propineb, prochloraz, procymidon, propamocarb, propiconazole, prothiocarb, pyracarbolid, pyrazophos, pyrifenox, pyrimethanil, pyroquilon, rabenzazole, RH7592, sulfur, tebuconazole, TF 167, thiabendazole, thicyofen, thiofanatemethyl, thiram, tolclofos-methyl, tolylfluanid, triadimefon, triadimenol, triazoxid, tricyclazole, tridemorph, triflumizol, triforine, trifionazol, validamycin, vinchlozolin, XRD 563, zineb, sodium dodecylsulfonate, sodium dodecyl sulfate, sodium C13/C15 alcohol ether sulfonate, sodium cetostearyl phosphate ester, sodium dioctylsulfosuccinate, sodium isopropylnaphthalenesulfonate, sodium methylenebisnaphthalenesulfonate, cetyltrimethylammonium chloride, salts of long-chain primary, secondary or tertiary amines, alkylpropyleneamines, laurylpyrimidinium bromide, ethoxylated quaternized fatty amines, alkyldimethylbenzylammonium chloride and 1-hydroxyethyl-2-alkylimidazoline.

The abovementioned components for combinations are known active substances of which many are described in Ch. R. Worthing, S. B. Walker, The Pesticide Manual, 7th edition (1983), British Crop Protection Council. The active substance content of the use forms prepared from commercially customary formulations can vary within wide limits, and the concentration of active substance in the use forms can be from 0.0001 up to 95% by weight of active substance, preferably between 0.0001 and 1% by weight. The formulations are applied in a customary manner adapted to suit the use forms.

The examples which follow illustrate the invention without limiting it thereto.

A. FORMULATION EXAMPLES a) A dusting agent is obtained by mixing 10 parts by weight of active substance and 90 parts by weight of talc as inert material and comminuting in a hammer mill.

b) A wettable powder which is easily dispersible in water is obtained by mixing 25 parts by weight of active substance, 65 parts by weight of kaolin-containing quartz as inert material, 10 parts by weight of potassium ligninsulfonate and 1 part by weight of sodium oleoylmethyltaurinate as wetting and dispersing agent, and grinding in a pinned disk mill.

c) A dispersion concentrate which is easily dispersible in water is prepared by mixing 40 parts by weight of active substance with 7 parts by weight of a sulfosuccinic monoester, 2 parts by weight of a sodium ligninsulfonate and 51 parts by weight of water and grinding in a ball mill to a fineness of below 5 microns.

d) An emulsifiable concentrate can be prepared from 15 parts by weight of active substance, 75 parts by weight of cyclohexane as solvent and 10 parts by weight of ethoxylated nonylphenol (10 EO) as emulsifier.

e) Granules can be prepared from 2 to 15 parts by weight of active substance and an inert granule carrier material such as attapulgite, granulated pumice and/or quartz sand. It is advantageous to use a suspension of the wettable powder of Example b) with a solids content of 30% which is sprayed onto the surface of attapulgite granules which are then dried and intimately mixed. The proportion by weight of the wettable powder in this case is about 5% and that of the inert carrier material is about 95% of the finished granules.

B. PREPARATION EXAMPLES

Example I

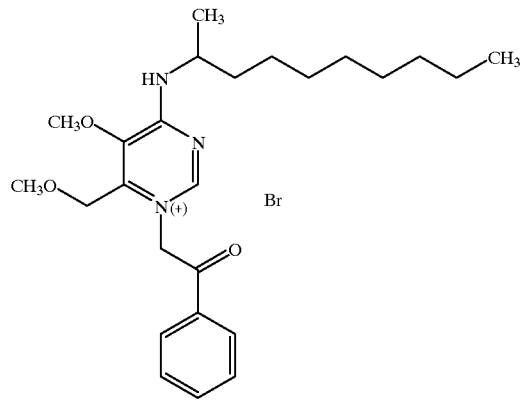

4-(2-Decylamino)-5-methoxy-6-methoxymethyl-1-phenacylpyrimidinium bromide

A mixture of 1.5 g (4.84 mmol) of 2-decylamino-5-methoxy-6-methoxymethylpyrimidine (DE-A4 116 089) and 0.96 g (4.84 mmol) of phenacyl bromide in 50 ml of ethanol was heated under reflux for 8 hours. After cooling, the solvent was removed under reduced pressure and the oily residue was stirred with petroleum ether. The resulting crystal slurry was filtered off with suction and the product was stirred in hot petroleum ether for another 5 minutes. Filtration with suction gave 1.15 g (61% of theory) of a yellow solid. mp. 118° C.

Example II

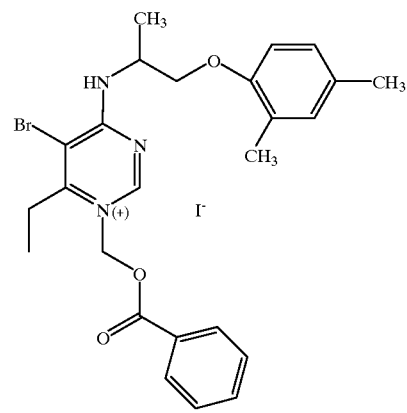

1-Benzoyloxymethyl-5-bromo-6-ethyl-4-[2-(2,4-dimethylphenoxy)-propylamino]pyrimidinium iodide 0.3 g (8.2 mmol) of 5-bromo-6-ethyl-4-[2-(2,4-dimethylphenoxy)-propylamino]pyrimidine (according to EP-A-57 440), 0.17 g (9.8 mmol) of chloromethyl benzoate and 0.12 g (8.2 mmol) of sodium iodide in 25 ml of acetone were heated under reflux for 8 hours. After cooling, the precipitated sodium chloride was filtered off and the filtrate was concentrated. The residue was taken up in dichloromethane and washed by stirring with water. The organic phase was dried and concentrated. The residue was digested with ethyl acetate. Filtration with suction gave 0.97 g (53.3% of theory) of light-yellow crystals. mp.: 159–161° C.

Similarly to the preparation examples mentioned, the following examples can be prepared (definitions of "Het$^n$" are given after Table 1):

TABLE 1

$$[Het^n - \underset{\underset{R^5}{|}}{CH} - E - R^6]^+ \quad Q^-$$

| Ex. No. | Het$^n$ | R$^5$ | E | R$^6$ | Q | Phys. properties |
|---|---|---|---|---|---|---|
| 1 | Het$^1$ | H | O | C(O)tBu | I | |
| 2 | Het$^1$ | H | O | C(O)Ph | I | |
| 3 | Het$^1$ | H | O | CH$_3$ | Cl | |
| 4 | Het$^1$ | H | CO | Ph | Br | |
| 5 | Het$^1$ | H | CO | 4-C$_6$H$_4$OCF$_3$ | Cl | |
| 6 | Het$^1$ | H | CO | 4-C$_6$H$_4$OC(O)Ph | Br | mp.: 235–237° C. |
| 7 | Het$^2$ | H | O | C(O)tBu | I | |
| 8 | Het$^2$ | H | O | C(O)Ph | I | |
| 9 | Het$^2$ | H | CO | Ph | Br | |
| 10 | Het$^2$ | H | CO | 4-C$_6$H$_4$NO$_2$ | Br | |
| 11 | Het$^2$ | H | CO | 4-(C$_6$H$_4$)OC(O)Ph | Br | |
| 12 | Het$^3$ | H | O | C(O)iPr | I | |
| 13 | Het$^3$ | H | O | C(O)tBu | I | |
| 14 | Het$^3$ | H | O | C(O)Ph | I | |
| 15 | Het$^3$ | H | O | C(O)-4-C$_6$H$_4$Cl | I | |
| 16 | Het$^3$ | CH$_3$ | O | C(O)Ph | I | |
| 17 | Het$^3$ | H | CO | Ph | Br | |
| 18 | Het$^3$ | H | CO | 4-C$_6$H$_4$OCF$_3$ | Br | |
| 19 | Het$^3$ | H | CO | 4-C$_6$H$_4$OC(O)Ph | Br | mp.: 189–190° C. |
| 20 | Het$^3$ | H | CO | 4-C$_6$H$_4$OC(O)tBu | Br | |
| 21 | Het$^3$ | H | CO | 2-C$_6$H$_4$NO$_2$ | Br | |
| 22 | Het$^4$ | H | O | C(O)tBu | I | |
| 23 | Het$^4$ | H | O | C(O)Ph | I | |
| 24 | Het$^4$ | H | CO | Ph | Br | mp.: 118° C. |
| 25 | Het$^4$ | H | CO | 4-C$_6$H$_4$Cl | Br | mp.: 143–144° C. |
| 26 | Het$^4$ | H | CO | 4-C$_6$H$_4$OC(O)Ph | Br | |
| 27 | Het$^5$ | H | O | C(O)tBu | I | |
| 28 | Het$^5$ | H | O | C(O)Ph | I | |
| 29 | Het$^5$ | H | CO | Ph | Br | |
| 30 | Het$^5$ | H | CO | 4-C$_6$H$_4$OC(C)Ph | Br | |
| 31 | Het$^6$ | H | O | C(O)tBu | I | |
| 32 | Het$^6$ | H | O | C(O)Ph | I | |
| 33 | Het$^6$ | H | CO | Ph | Br | |
| 34 | Het$^6$ | H | CO | 4-C$_6$H$_4$OC(O)Ph | Br | |
| 35 | Het$^7$ | H | O | C(O)tBu | I | |
| 36 | Het$^7$ | H | O | C(O)Ph | I | |
| 37 | Het$^7$ | H | CO | Ph | Br | |
| 38 | Het$^7$ | H | CO | 4-C$_6$H$_4$OC(O)Ph | Br | |
| 39 | Het$^8$ | H | O | C(O)tBu | I | |
| 40 | Het$^8$ | H | O | C(O)Ph | I | |
| 41 | Het$^8$ | H | CO | Ph | Br | |
| 42 | Het$^8$ | H | CO | 4C$_6$H$_4$OC(O)Ph | Br | |
| 43 | Het$^9$ | H | O | C(O)tBu | I | |
| 44 | Het$^9$ | H | O | C(O)Ph | I | |
| 45 | Het$^9$ | H | CO | Ph | Br | |
| 46 | Het$^9$ | H | CO | 4-C$_6$H$_4$OC(O)Ph | Br | |
| 47 | Het$^{10}$ | H | O | C(O)tBu | I | |
| 48 | Het$^{10}$ | H | O | C(O)Ph | I | |
| 49 | Het$^{10}$ | H | CO | Ph | Br | |
| 50 | Het$^{10}$ | H | CO | 4-C$_6$H$_4$OC(O)Ph | Br | |
| 51 | Het$^{11}$ | H | O | C(O)tBu | I | |
| 52 | Het$^{11}$ | H | O | C(O)Ph | I | |
| 53 | Het$^{11}$ | H | CO | Ph | Br | |
| 54 | Het$^{11}$ | H | CO | 4-C$_6$H$_4$OC(O)Ph | Br | |
| 55 | Het$^{12}$ | H | O | C(O)tBu | I | |
| 56 | Het$^{12}$ | H | O | C(O)Ph | I | |
| 57 | Het$^{12}$ | H | CO | Ph | Br | |
| 58 | Het$^{12}$ | H | CO | 4-C$_6$H$_4$OC(O)Ph | Br | |
| 59 | Het$^{13}$ | H | O | C(O)tBu | I | |
| 60 | Het$^{13}$ | H | O | C(O)Ph | I | |
| 61 | Het$^{13}$ | H | CO | Ph | Br | |
| 62 | Het$^{13}$ | H | CO | 4-C$_6$H$_4$OC(O)Ph | Br | |
| 63 | Het$^{14}$ | H | O | C(O)tBu | I | |
| 64 | Het$^{14}$ | H | O | C(O)Ph | I | |
| 65 | Het$^{14}$ | H | CO | Ph | Br | |
| 66 | Het$^{14}$ | H | CO | 4-C$_6$H$_4$OC(O)Ph | Br | |
| 67 | Het$^{15}$ | H | O | C(O)tBu | I | |
| 68 | Het$^{15}$ | H | O | C(O)Ph | I | |
| 69 | Het$^{15}$ | H | CO | Ph | Br | |
| 70 | Het$^{15}$ | H | CO | 4-C$_6$H$_4$OC(O)Ph | Br | |
| 71 | Het$^{16}$ | H | O | C(O)tBu | I | |
| 72 | Het$^{16}$ | H | O | C(O)Ph | I | |
| 73 | Het$^{16}$ | H | CO | Ph | Br | |
| 74 | Het$^{16}$ | H | CO | 4-C$_6$H$_4$OC(O)Ph | Br | |
| 75 | Het$^{17}$ | H | O | C(O)tBu | I | |
| 76 | Het$^{17}$ | H | O | C(O)Ph | I | |
| 77 | Het$^{17}$ | H | CO | 4-C$_6$H$_4$OC(O)CH$_3$ | Br | |
| 78 | Het$^{17}$ | H | CO | Ph | Br | |
| 79 | Het$^{17}$ | H | CO | 4-C$_6$H$_4$OC(O)Ph | Br | |
| 80 | Het$^{18}$ | H | O | C(O)tBu | I | |
| 81 | Het$^{18}$ | H | O | C(O)Ph | I | |
| 82 | Het$^{18}$ | H | CO | Ph | Br | |
| 83 | Het$^{18}$ | H | CO | 4-C$_6$H$_4$OC(O)Ph | Br | mp.: 165–168° C. |
| 84 | Het$^{19}$ | H | O | C(O)tBu | I | |
| 85 | Het$^{19}$ | H | O | C(O)Ph | I | |
| 86 | Het$^{19}$ | H | CO | Ph | Br | |
| 87 | Het$^{19}$ | H | CO | 4-C$_6$H$_4$OC(O)Ph | Br | |
| 88 | Het$^{20}$ | H | O | C(O)tBu | I | |
| 89 | Het$^{20}$ | H | O | C(O)Ph | I | |
| 90 | Het$^{20}$ | H | CO | Ph | Br | |
| 91 | Het$^{20}$ | H | CO | 4-C$_6$H$_4$OC(O)Ph | Br | |
| 92 | Het$^{21}$ | H | O | C(O)tBu | I | |
| 93 | Het$^{21}$ | H | O | C(O)Ph | I | |
| 94 | Het$^{21}$ | H | CO | Ph | Br | |
| 95 | Het$^{21}$ | H | CO | 4-C$_6$H$_4$OC(O)Ph | Br | |
| 96 | Het$^{22}$ | H | O | C(O)tBu | I | |
| 97 | Het$^{22}$ | H | O | C(O)Ph | I | |
| 98 | Het$^{22}$ | H | CO | Ph | Br | |
| 99 | Het$^{22}$ | H | CO | 4-C$_6$H$_4$OC(O)Ph | Br | |
| 100 | Het$^{23}$ | H | O | C(O)tBu | I | |
| 101 | Het$^{23}$ | H | O | C(O)Ph | I | |
| 102 | Het$^{23}$ | H | CO | Ph | Br | |
| 103 | Het$^{23}$ | H | CO | 4-C$_6$H$_4$OC(O)Ph | Br | |
| 104 | Het$^{24}$ | H | O | C(O)tBu | I | |
| 105 | Het$^{24}$ | H | O | C(O)Ph | I | |
| 106 | Het$^{24}$ | H | CO | Ph | Br | |
| 107 | Het$^{24}$ | H | CO | 4-C$_6$H$_4$OC(O)Ph | Br | |
| 108 | Het$^{25}$ | H | O | C(O)tBu | I | |
| 109 | Het$^{25}$ | H | O | C(O)Ph | I | |
| 110 | Het$^{25}$ | H | CO | Ph | Br | |
| 111 | Het$^{25}$ | H | CO | 4-C$_6$H$_4$OC(O)Ph | Br | |
| 112 | Het$^{26}$ | H | O | C(O)tBu | I | |
| 113 | Het$^{26}$ | H | O | C(O)Ph | I | |
| 114 | Het$^{26}$ | H | CO | Ph | Br | |
| 115 | Het$^{26}$ | H | CO | 4-C$_6$H$_4$OC(O)Ph | Br | |
| 116 | Het$^{27}$ | H | O | C(O)tBu | I | |
| 117 | Het$^{27}$ | H | O | C(O)Ph | I | |
| 118 | Het$^{27}$ | H | CO | Ph | Br | |
| 119 | Het$^{27}$ | H | CO | 4-C$_6$H$_4$OC(O)Ph | Br | |
| 120 | Het$^{28}$ | H | O | C(O)tBu | I | |
| 121 | Het$^{28}$ | H | O | C(O)Ph | I | |
| 122 | Het$^{28}$ | H | CO | Ph | Br | |
| 123 | Het$^{28}$ | H | CO | 4-C$_6$H$_4$OC(O)Ph | Br | |
| 124 | Het$^{29}$ | H | O | C(O)iC$_3$H$_7$ | I | |
| 125 | Het$^{29}$ | H | O | C(O)tBu | I | |
| 126 | Het$^{29}$ | H | O | C(O)Ph | I | |
| 127 | Het$^{29}$ | H | CO | Ph | Br | |
| 128 | Het$^{29}$ | H | CO | 4-C$_6$H$_4$OCF$_3$ | Br | |
| 129 | Het$^{29}$ | H | CO | 4-C$_6$H$_4$OC(O)Ph | Br | |
| 130 | Het$^{29}$ | H | CO | 4-C$_6$H$_4$OC(O)tBu | Br | |
| 131 | Het$^{30}$ | H | O | C(O)iC$_3$H$_7$ | I | |
| 132 | Het$^{30}$ | H | O | C(O)tBu | I | |
| 133 | Het$^{30}$ | H | O | C(O)Ph | I | |

TABLE 1-continued $$[\text{Het}^n\text{---CH(R}^5)\text{---E---R}^6]^+ \; Q^-$$

| Ex. No. | Het$^n$ | R$^5$ | E | R$^6$ | Q | Phys. properties |
|---|---|---|---|---|---|---|
| 134 | Het$^{30}$ | H | CO | Ph | Br | |
| 135 | Het$^{30}$ | H | CO | 4-C$_6$H$_4$OCF$_3$ | Br | |
| 136 | Het$^{30}$ | H | CO | 4-C$_6$H$_4$OC(O)Ph | Br | |
| 137 | Het$^{30}$ | H | CO | 4-(C$_6$H$_4$OC(O)tBu | Br | |
| 138 | Het$^{31}$ | H | O | C(O)tBu | I | |
| 139 | Het$^{31}$ | H | O | C(O)Ph | I | |
| 140 | Het$^{31}$ | H | CO | Ph | Br | |
| 141 | Het$^{31}$ | H | CO | 4-C$_6$H$_4$OC(O)Ph | Br | |
| 142 | Het$^{32}$ | H | O | C(O)tBu | I | |
| 143 | Het$^{32}$ | H | O | C(O)Ph | I | |
| 144 | Het$^{32}$ | H | CO | Ph | Br | |
| 145 | Het$^{32}$ | H | CO | 4-C$_6$H$_4$OC(O)Ph | Br | |
| 146 | Het$^{33}$ | H | O | C(O)tBu | I | |
| 147 | Het$^{33}$ | H | O | C(O)Ph | I | |
| 148 | Het$^{33}$ | H | CO | Ph | Br | |
| 149 | Het$^{33}$ | H | CO | 4-C$_6$H$_4$OC(O)Ph | Br | |
| 150 | Het$^{34}$ | H | O | C(O)tBu | I | |
| 151 | Het$^{34}$ | H | O | C(O)Ph | I | |
| 152 | Het$^{34}$ | H | CO | Ph | Br | |
| 153 | Het$^{34}$ | H | CO | 4-C$_6$H$_4$OC(O)Ph | Br | |
| 154 | Het$^{35}$ | H | O | C(O)tBu | I | |
| 155 | Het$^{35}$ | H | O | C(O)Ph | I | |
| 156 | Het$^{35}$ | H | CO | Ph | Br | |
| 157 | Het$^{35}$ | H | CO | 4-C$_6$H$_4$OC(O)Ph | Br | |
| 158 | Het$^{36}$ | H | O | C(O)tBu | I | |
| 159 | Het$^{36}$ | H | O | C(O)Ph | I | |
| 160 | Het$^{36}$ | H | CO | Ph | Br | |
| 161 | Het$^{36}$ | H | CO | 4-C$_6$H$_4$OC(O)Ph | Br | |
| 162 | Het$^{37}$ | H | O | C(O)tBu | I | |
| 163 | Het$^{37}$ | H | O | C(O)Ph | I | |
| 164 | Het$^{37}$ | H | CO | Ph | Br | |
| 165 | Het$^{37}$ | H | CO | 4-C$_6$H$_4$OC(O)Ph | Br | |
| 166 | Het$^{38}$ | H | O | C(O)tBu | I | |
| 167 | Het$^{38}$ | H | O | C(O)Ph | I | |
| 168 | Het$^{38}$ | H | CO | Ph | Br | |
| 169 | Het$^{38}$ | H | CO | 4-C$_6$H$_4$OC(O)Ph | Br | |
| 170 | Het$^{39}$ | H | O | C(O)tBu | I | |
| 171 | Het$^{39}$ | H | O | C(O)Ph | I | |
| 172 | Het$^{39}$ | H | CO | Ph | Br | |
| 173 | Het$^{39}$ | H | CO | 4-C$_6$H$_4$OC(O)Ph | Br | |
| 174 | Het$^{40}$ | H | O | C(O)tBu | I | |
| 175 | Het$^{40}$ | H | O | C(O)Ph | I | |
| 176 | Het$^{40}$ | H | CO | Ph | Br | |
| 177 | Het$^{40}$ | H | CO | 4-C$_6$H$_4$OC(O)Ph | Br | |
| 178 | Het$^{41}$ | H | O | C(O)tBu | I | |
| 179 | Het$^{41}$ | H | O | C(O)Ph | I | mp.: 159–161° C. |
| 180 | Het$^{41}$ | H | CO | Ph | Br | |
| 181 | Het$^{41}$ | H | CO | 4-C$_6$H$_4$OC(O)Ph | Br | |
| 182 | Het$^{42}$ | H | O | C(O)tBu | I | |
| 183 | Het$^{42}$ | H | O | C(O)Ph | I | |
| 184 | Het$^{42}$ | H | CO | Ph | Br | |
| 185 | Het$^{42}$ | H | CO | 4-C$_6$H$_4$OC(O)Ph | Br | mp.: 139–175° C. |
| 186 | Het$^{43}$ | H | O | C(O)tBu | I | |
| 187 | Het$^{43}$ | H | O | C(O)Ph | I | mp.: 192° C. |
| 188 | Het$^{43}$ | H | CO | Ph | Br | |
| 189 | Het$^{43}$ | H | CO | 4-C$_6$H$_4$OC(O)Ph | Br | |
| 190 | Het$^{44}$ | H | O | C(O)tBu | I | |
| 191 | Het$^{44}$ | H | O | C(O)Ph | I | |
| 192 | Het$^{44}$ | H | CO | Ph | Br | |
| 193 | Het$^{44}$ | H | CO | 4-C$_6$H$_4$OC(O)Ph | Br | |
| 194 | Het$^{45}$ | H | O | C(O)tBu | I | |
| 195 | Het$^{45}$ | H | O | C(O)Ph | I | |
| 196 | Het$^{45}$ | H | CO | Ph | Br | |
| 197 | Het$^{45}$ | H | CO | 4-C$_6$H$_4$OC(O)Ph | Br | mp.: 183–184° C. |
| 198 | Het$^{46}$ | H | O | C(O)tBu | I | |
| 199 | Het$^{46}$ | H | O | C(O)Ph | I | |
| 200 | Het$^{46}$ | H | CO | Ph | Br | |
| 201 | Het$^{46}$ | H | CO | 4-C$_6$H$_4$OC(O)Ph | Br | |
| 202 | Het$^{47}$ | H | O | C(O)tBu | I | |
| 203 | Het$^{47}$ | H | O | C(O)Ph | I | |
| 204 | Het$^{47}$ | H | CO | Ph | Br | |
| 205 | Het$^{47}$ | H | CO | 4-C$_6$H$_4$OC(O)Ph | Br | |
| 206 | Het$^{48}$ | H | O | C(O)tBu | I | |
| 207 | Het$^{48}$ | H | O | C(O)Ph | I | |
| 208 | Het$^{48}$ | H | CO | Ph | Br | |
| 209 | Het$^{48}$ | H | CO | 4-C$_6$H$_4$OC(O)Ph | Br | |
| 210 | Het$^{49}$ | H | O | C(O)tBu | I | |
| 211 | Het$^{49}$ | H | O | C(O)Ph | I | mp.: 89–90° C. |
| 212 | Het$^{49}$ | H | CO | Ph | Br | |
| 213 | Het$^{49}$ | H | CO | 4-C$_6$H$_4$OC(O)Ph | Br | |
| 214 | Het$^{50}$ | H | O | C(O)tBu | I | |
| 215 | Het$^{50}$ | H | O | C(O)Ph | I | |
| 216 | Het$^{50}$ | H | CO | Ph | Br | |
| 217 | Het$^{50}$ | H | CO | 4-C$_6$H$_4$OC(O)Ph | Br | |
| 218 | Het$^{51}$ | H | O | C(O)tBu | I | |
| 219 | Het$^{51}$ | H | O | C(O)Ph | I | mp.: 122° C. |
| 220 | Het$^{51}$ | H | CO | Ph | Br | |
| 221 | Het$^{51}$ | H | CO | 4-C$_6$H$_4$OC(O)Ph | Br | |
| 222 | Het$^{52}$ | H | O | C(O)tBu | I | |
| 223 | Het$^{52}$ | H | O | C(O)Ph | I | |
| 224 | Het$^{52}$ | H | CO | Ph | Br | |
| 225 | Het$^{52}$ | H | CO | 4-C$_6$H$_4$OC(O)Ph | Br | |
| 226 | Het$^{53}$ | H | O | C(O)iC$_3$H$_7$ | I | |
| 227 | Het$^{53}$ | H | O | C(O)tBu | I | |
| 228 | Het$^{53}$ | H | O | C(O)Ph | I | |
| 229 | Het$^{53}$ | H | CO | Ph | Br | |
| 230 | Het$^{53}$ | H | CO | 4-C$_6$H$_4$OCF$_3$ | Br | |
| 231 | Het$^{53}$ | H | CO | 4-C$_6$H$_4$OC(O)Ph | Br | |
| 232 | Het$^{53}$ | H | CO | 4-C$_6$H$_4$OC(O)tBu | Br | |
| 233 | Het$^{54}$ | H | O | C(O)tBu | I | |
| 234 | Het$^{54}$ | H | O | C(O)Ph | I | |
| 235 | Het$^{54}$ | H | CO | Ph | Br | |
| 236 | Het$^{54}$ | H | CO | 4-C$_6$H$_4$OC(O)Ph | Br | |
| 237 | Het$^{55}$ | H | O | C(O)tBu | I | |
| 238 | Het$^{55}$ | H | O | C(O)Ph | I | |
| 239 | Het$^{55}$ | H | CO | Ph | Br | |
| 240 | Het$^{55}$ | H | CO | 4-C$_6$H$_4$OC(O)Ph | Br | mp.: 188–190° C. |
| 241 | Het$^{56}$ | H | O | C(O)tBu | I | |
| 242 | Het$^{56}$ | H | O | C(O)Ph | I | mp.: 164° C. |
| 243 | Het$^{56}$ | H | CO | Ph | Br | |
| 244 | Het$^{56}$ | H | CO | 4-C$_6$H$_4$OC(O)Ph | Br | |
| 245 | Het$^{57}$ | H | O | C(O)tBu | I | |
| 246 | Het$^{57}$ | H | O | C(O)Ph | I | |
| 247 | Het$^{57}$ | H | CO | Ph | Br | |
| 248 | Het$^{57}$ | H | CO | 4-C$_6$H$_4$OC(O)Ph | Br | |
| 249 | Het$^{58}$ | H | O | C(O)tBu | I | |
| 250 | Het$^{58}$ | H | O | C(O)Ph | I | |
| 251 | Het$^{58}$ | H | CO | Ph | Br | |
| 252 | Het$^{58}$ | H | CO | 4-C$_6$H$_4$OC(O)Ph | Br | |
| 253 | Het$^{59}$ | H | O | C(O)tBu | I | |
| 254 | Het$^{59}$ | H | O | C(O)Ph | I | |
| 255 | Het$^{59}$ | H | CO | Ph | Br | |
| 256 | Het$^{59}$ | H | CO | 4-C$_6$H$_4$OC(O)Ph | Br | |
| 257 | Het$^{60}$ | H | O | C(O)tBu | I | |
| 258 | Het$^{60}$ | H | O | C(O)Ph | I | |
| 259 | Het$^{60}$ | H | CO | Ph | Br | |
| 260 | Het$^{60}$ | H | CO | 4-C$_6$H$_4$OC(O)Ph | Br | |
| 261 | Het$^{61}$ | H | O | C(O)tBu | I | |
| 262 | Het$^{61}$ | H | O | C(O)Ph | I | |
| 263 | Het$^{61}$ | H | CO | Ph | Br | |
| 264 | Het$^{61}$ | H | CO | 4-C$_6$H$_4$OC(O)Ph | Br | |
| 265 | Het$^{62}$ | H | O | C(O)iPr | I | |
| 266 | Het$^{62}$ | H | O | C(O)tBu | I | |
| 267 | Het$^{62}$ | H | O | C(O)Ph | I | |
| 268 | Het$^{62}$ | H | CO | Ph | Br | |
| 269 | Het$^{62}$ | H | CC | 4-C$_6$H$_4$OCF$_3$ | Br | |
| 270 | Het$^{62}$ | H | CO | 4-C$_6$H$_4$OC(O)Ph | Br | |
| 271 | Het$^{62}$ | H | CO | 4-C$_6$H$_4$OC(O)tBu | Br | |
| 272 | Het$^{63}$ | H | O | C(O)iBr | I | |
| 273 | Het$^{63}$ | H | O | C(O)tBu | I | |
| 274 | Het$^{63}$ | H | O | C(O)Ph | I | |
| 275 | Het$^{63}$ | H | CO | Ph | Br | |

TABLE 1-continued $$[\text{Het}^n-\underset{\underset{R^5}{|}}{CH}-E-R^6]^+ \quad Q^-$$

| Ex. No. | Het$^n$ | R$^5$ | E | R$^6$ | Q | Phys. properties |
|---|---|---|---|---|---|---|
| 276 | Het$^{63}$ | H | CO | 4-C$_6$H$_4$OCF$_3$ | Br | |
| 277 | Het$^{63}$ | H | CO | 4-C$_6$H$_4$OC(O)Ph | Br | |
| 278 | Het$^{63}$ | H | CO | 4-C$_6$H$_4$OC(O)tBu | Br | |
| 279 | Het$^{64}$ | H | O | C(O)tBu | I | |
| 280 | Het$^{64}$ | H | O | C(O)Ph | I | |
| 281 | Het$^{64}$ | H | CO | Ph | Br | |
| 282 | Het$^{64}$ | H | CO | 4-C$_6$H$_4$OC(O)Ph | Br | |
| 283 | Het$^{65}$ | H | O | C(O)tBu | I | |
| 284 | Het$^{65}$ | H | O | C(O)Ph | I | |
| 285 | Het$^{65}$ | H | CO | Ph | Br | |
| 286 | Het$^{65}$ | H | CO | 4-C$_6$H$_4$OC(O)Ph | Br | |
| 287 | Het$^{66}$ | H | O | C(O)tBu | I | |
| 288 | Het$^{66}$ | H | O | C(O)Ph | I | |
| 289 | Het$^{66}$ | H | CO | Ph | Br | |
| 290 | Het$^{66}$ | H | CO | 4-C$_6$H$_4$OC(O)Ph | Br | |
| 291 | Het$^{67}$ | H | O | C(O)tBu | I | |
| 292 | Het$^{67}$ | H | O | C(O)Ph | I | |
| 293 | Het$^{67}$ | H | CO | Ph | Br | |
| 294 | Het$^{67}$ | H | CC | 4-C$_6$H$_4$OC(O)Ph | Br | |
| 295 | Het$^{68}$ | H | O | C(O)tBu | I | |
| 296 | Het$^{68}$ | H | O | C(O)Ph | I | |
| 297 | Het$^{68}$ | H | CO | Ph | Br | |
| 298 | Het$^{68}$ | H | CO | 4-C$_6$H$_4$OC(O)Ph | Br | |
| 299 | Het$^{69}$ | H | O | C(O)tBu | I | |
| 300 | Het$^{69}$ | H | O | C(O)Ph | I | |
| 301 | Het$^{69}$ | H | CO | Ph | Br | |
| 302 | Het$^{69}$ | H | CO | 4-C$_6$H$_4$OC(O)Ph | Br | |
| 303 | Het$^{70}$ | H | O | C(O)tBu | I | |
| 304 | Het$^{70}$ | H | O | C(O)Ph | I | |
| 305 | Het$^{70}$ | H | CO | Ph | Br | |
| 306 | Het$^{70}$ | H | CO | 4-C$_6$H$_4$OC(O)Ph | Br | |
| 307 | Het$^{71}$ | H | O | C(O)tBu | I | |
| 308 | Het$^{71}$ | H | O | C(O)Ph | I | |
| 309 | Het$^{71}$ | H | CO | Ph | Br | |
| 310 | Het$^{71}$ | H | CO | 4-C$_6$H$_4$OC(O)Ph | Br | |
| 311 | Het$^{72}$ | H | O | C(O)iPr | I | |
| 312 | Het$^{72}$ | H | O | C(O)tBu | I | |
| 313 | Het$^{72}$ | H | O | C(O)Ph | I | |
| 314 | Het$^{72}$ | H | CO | Ph | Br | |
| 315 | Het$^{72}$ | H | CO | 4-C$_6$H$_4$OCF$_3$ | Br | |
| 316 | Het$^{72}$ | H | CO | 4-C$_6$H$_4$OC(O)Ph | Br | |
| 317 | Het$^{72}$ | H | CO | 4-C$_6$H$_4$OC(O)tBu | Br | |
| 318 | Het$^{73}$ | H | O | C(O)iPr | I | |
| 319 | Het$^{73}$ | H | O | C(O)tBu | I | |
| 320 | Het$^{73}$ | H | O | C(O)Ph | I | |
| 321 | Het$^{73}$ | H | CO | Ph | Br | |
| 322 | Het$^{73}$ | H | CO | 4-C$_6$H$_4$OCF$_3$ | Br | |
| 323 | Het$^{73}$ | H | CO | 4-C$_6$H$_4$OC(O)Ph | Br | |
| 324 | Het$^{73}$ | H | CO | 4-C$_6$H$_4$OC(O)tBu | Br | |
| 325 | Het$^{74}$ | H | O | C(O)tBu | I | |
| 326 | Het$^{74}$ | H | O | C(O)Ph | I | |
| 327 | Het$^{74}$ | H | CO | Ph | Br | |
| 328 | Het$^{74}$ | H | CO | 4-C$_6$H$_4$OC(O)Ph | Br | |
| 329 | Het$^{75}$ | H | O | C(O)tBu | I | |
| 330 | Het$^{75}$ | H | O | C(O)Ph | I | |
| 331 | Het$^{75}$ | H | CO | Ph | Br | |
| 332 | Het$^{75}$ | H | CO | 4-C$_6$H$_4$OC(O)Ph | Br | |
| 333 | Het$^{76}$ | H | O | C(O)tBu | I | |
| 334 | Het$^{76}$ | H | O | C(O)Ph | I | |
| 335 | Het$^{76}$ | H | CO | Ph | Br | |
| 336 | Het$^{76}$ | H | CO | 4-C$_6$H$_4$OC(O)Ph | Br | |
| 337 | Het$^{77}$ | H | O | C(O)tBu | I | |
| 338 | Het$^{77}$ | H | O | C(O)Ph | I | |
| 339 | Het$^{77}$ | H | CO | Ph | Br | |
| 340 | Het$^{77}$ | H | CO | 4-C$_6$H$_4$OC(O)Ph | Br | |
| 341 | Het$^{78}$ | H | O | C(O)tBu | I | |
| 342 | Het$^{78}$ | H | O | C(O)Ph | I | |
| 343 | Het$^{78}$ | H | CO | Ph | Br | |
| 344 | Het$^{78}$ | H | CO | 4-C$_6$H$_4$OC(O)Ph | Br | |
| 345 | Het$^{79}$ | H | O | C(O)tBu | I | |
| 346 | Het$^{79}$ | H | O | C(O)Ph | I | |
| 347 | Het$^{79}$ | H | CO | Ph | Br | |
| 348 | Het$^{79}$ | H | CO | 4-C$_6$H$_4$OC(O)Ph | Br | |
| 349 | Het$^{80}$ | H | O | C(O)tBu | I | |
| 350 | Het$^{80}$ | H | O | C(O)Ph | I | |
| 351 | Het$^{80}$ | H | CO | Ph | Br | |
| 352 | Het$^{80}$ | H | CO | 4-C$_6$H$_4$OC(O)Ph | Br | |
| 353 | Het$^{81}$ | H | O | C(O)tBu | I | |
| 354 | Het$^{81}$ | H | O | C(O)Ph | I | |
| 355 | Het$^{81}$ | H | CO | Ph | Br | |
| 356 | Het$^{81}$ | H | CO | 4-C$_6$H$_4$OC(O)Ph | Br | |
| 357 | Het$^{82}$ | H | O | C(O)tBu | I | |
| 358 | Het$^{82}$ | H | O | C(O)Ph | I | |
| 359 | Het$^{82}$ | H | CO | Ph | Br | |
| 360 | Het$^{82}$ | H | CO | 4-C$_6$H$_4$OC(O)Ph | Br | |
| 361 | Het$^{83}$ | H | O | C(O)tBu | I | |
| 362 | Het$^{83}$ | H | O | C(O)Ph | I | |
| 363 | Het$^{83}$ | H | CO | Ph | Br | |
| 364 | Het$^{83}$ | H | CO | 4-C$_6$H$_4$OC(O)Ph | Br | |
| 365 | Het$^{84}$ | H | O | C(O)tBu | I | |
| 366 | Het$^{84}$ | H | O | C(O)Ph | I | |
| 367 | Het$^{84}$ | H | CO | Ph | Br | |
| 368 | Het$^{84}$ | H | CO | 4-C$_6$H$_4$OC(O)Ph | Br | |
| 369 | Het$^{85}$ | H | O | C(O)tBu | I | |
| 370 | Het$^{85}$ | H | O | C(O)Ph | I | |
| 371 | Het$^{85}$ | H | CO | Ph | Br | |
| 372 | Het$^{85}$ | H | CO | 4-C$_6$H$_4$OC(O)Ph | Br | |
| 373 | Het$^{86}$ | H | O | C(O)tBu | I | |
| 374 | Het$^{86}$ | H | O | C(O)Ph | I | |
| 375 | Het$^{86}$ | H | CO | Ph | Br | |
| 376 | Het$^{86}$ | H | CO | 4-C$_6$H$_4$OC(O)Ph | Br | |
| 377 | Het$^{87}$ | H | O | C(O)tBu | I | |
| 378 | Het$^{87}$ | H | O | C(O)Ph | I | |
| 379 | Het$^{87}$ | H | CO | Ph | Br | |
| 380 | Het$^{87}$ | H | CO | 4-C$_6$H$_4$OC(O)Ph | Br | |
| 381 | Het$^{88}$ | H | O | C(O)tBu | I | |
| 382 | Het$^{88}$ | H | O | C(O)Ph | I | |
| 383 | Het$^{88}$ | H | CO | Ph | Br | |
| 384 | Het$^{88}$ | H | CO | 4-C$_6$H$_4$OC(O)Ph | Br | mp.: 141–168° C. |
| 385 | Het$^{89}$ | H | O | C(O)tBu | I | |
| 386 | Het$^{89}$ | H | O | C(O)Ph | I | |
| 387 | Het$^{89}$ | H | CO | Ph | Br | |
| 388 | Het$^{89}$ | H | CO | 4-C$_6$H$_4$OC(O)Ph | Br | |
| 389 | Het$^{90}$ | H | O | C(O)tBu | I | |
| 390 | Het$^{90}$ | H | O | C(O)Ph | I | |
| 391 | Het$^{90}$ | H | CO | Ph | Br | |
| 392 | Het$^{90}$ | H | CO | 4-C$_6$H$_4$OC(O)Ph | Br | |
| 393 | Het$^{91}$ | H | O | C(O)tBu | I | |
| 394 | Het$^{91}$ | H | O | C(O)Ph | I | |
| 395 | Het$^{91}$ | H | CO | Ph | Br | |
| 396 | Het$^{91}$ | H | CO | 4-C$_6$H$_4$OC(O)Ph | Br | |
| 397 | Het$^{92}$ | H | O | C(O)tBu | I | |
| 398 | Het$^{92}$ | H | O | C(O)Ph | I | |
| 399 | Het$^{92}$ | H | CO | Ph | Br | |
| 400 | Het$^{92}$ | H | CO | 4-C$_6$H$_4$OC(O)Ph | Br | |
| 401 | Het$^{93}$ | H | O | C(O)tBu | I | |
| 402 | Het$^{93}$ | H | O | C(O)Ph | I | |
| 403 | Het$^{93}$ | H | CO | Ph | Br | |
| 404 | Het$^{93}$ | H | CO | 4-C$_6$H$_4$OC(C)Ph | Br | |
| 405 | Het$^{94}$ | H | O | C(O)tBu | I | |
| 406 | Het$^{94}$ | H | O | C(O)Ph | I | |
| 407 | Het$^{95}$ | H | CO | Ph | Br | |
| 408 | Het$^{95}$ | H | CO | 4-C$_6$H$_4$OC(O)Ph | Br | |
| 409 | Het$^{95}$ | H | O | C(O)tBu | I | |
| 410 | Het$^{95}$ | H | O | C(O)Ph | I | |
| 411 | Het$^{95}$ | H | CO | Ph | Br | |
| 412 | Het$^{95}$ | H | CO | 4-C$_6$H$_4$OC(O)Ph | Br | |
| 413 | Het$^{96}$ | H | O | C(O)tBu | I | |
| 414 | Het$^{96}$ | H | O | C(O)Ph | I | |
| 415 | Het$^{96}$ | H | CO | Ph | Br | |
| 416 | Het$^{96}$ | H | CO | 4-C$_6$H$_4$OC(O)Ph | Br | |
| 417 | Het$^{97}$ | H | O | C(O)tBu | I | |

TABLE 1-continued $$[\text{Het}^n\text{—CH}(\text{R}^5)\text{—E—R}^6]^+ \; Q^-$$

| Ex. No. | Het$^n$ | R$^5$ | E | R$^6$ | Q | Phys. properties |
|---|---|---|---|---|---|---|
| 418 | Het$^{97}$ | H | O | C(O)Ph | I | |
| 419 | Het$^{97}$ | H | CO | Ph | Br | |
| 420 | Het$^{97}$ | H | CO | 4-C$_6$H$_4$OC(O)Ph | Br | |
| 421 | Het$^{98}$ | H | O | C(O)tBu | I | |
| 422 | Het$^{98}$ | H | O | C(O)Ph | I | |
| 423 | Het$^{98}$ | H | CO | Ph | Br | |
| 424 | Het$^{98}$ | H | CO | 4-C$_6$H$_4$OC(O)Ph | Br | |
| 425 | Het$^{99}$ | H | O | C(O)tBu | I | |
| 426 | Het$^{99}$ | H | O | C(O)Ph | I | |
| 427 | Het$^{99}$ | H | CO | Ph | Br | |
| 428 | Het$^{99}$ | H | CO | 4-C$_6$H$_4$OC(O)Ph | Br | |
| 429 | Het$^{100}$ | H | O | C(O)tBu | I | |
| 430 | Het$^{100}$ | H | O | C(O)Ph | I | |
| 431 | Het$^{100}$ | H | CO | Ph | Br | |
| 432 | Het$^{100}$ | H | CO | 4-C$_6$H$_4$OC(O)Ph | Br | |
| 433 | Het$^{101}$ | H | O | C(O)tBu | I | |
| 434 | Het$^{101}$ | H | O | C(O)Ph | I | |
| 435 | Het$^{101}$ | H | CO | Ph | Br | |
| 436 | Het$^{101}$ | H | CO | 4-C$_6$H$_4$OC(O)Ph | Br | |
| 437 | Het$^{102}$ | H | O | C(O)tBu | I | |
| 438 | Het$^{102}$ | H | O | C(O)Ph | I | |
| 439 | Het$^{102}$ | H | CO | Ph | Br | |
| 440 | Het$^{102}$ | H | CO | 4-C$_6$H$_4$OC(O)Ph | Br | |
| 441 | Het$^{103}$ | H | O | C(O)tBu | I | |
| 442 | Het$^{103}$ | H | O | C(O)Ph | I | |
| 443 | Het$^{103}$ | H | CO | Ph | Br | |
| 444 | Het$^{103}$ | H | CO | 4-C$_6$H$_4$OC(O)Ph | Br | |
| 445 | Het$^{104}$ | H | O | C(O)tBu | I | |
| 446 | Het$^{104}$ | H | O | C(O)Ph | I | |
| 447 | Het$^{104}$ | H | CO | Ph | Br | |
| 448 | Het$^{104}$ | H | CO | 4-C$_6$H$_4$OC(O)Ph | Br | |
| 449 | Het$^{105}$ | H | O | C(O)tBu | I | |
| 450 | Het$^{105}$ | H | O | C(O)Ph | I | |
| 451 | Het$^{105}$ | H | CO | Ph | Br | |
| 452 | Het$^{105}$ | H | CO | 4-C$_6$H$_4$OC(O)Ph | Br | |
| 453 | Het$^{106}$ | H | O | C(O)tBu | I | |
| 454 | Het$^{106}$ | H | O | C(O)Ph | I | |
| 455 | Het$^{106}$ | H | CO | Ph | Br | |
| 456 | Het$^{106}$ | H | CO | 4-C$_6$H$_4$OC(O)Ph | Br | |
| 457 | Het$^{107}$ | H | O | C(O)tBu | I | |
| 458 | Het$^{107}$ | H | O | C(O)Ph | I | |
| 459 | Het$^{107}$ | H | CO | Ph | Br | |
| 460 | Het$^{107}$ | H | CO | 4-C$_6$H$_4$OC(O)Ph | Br | |
| 461 | Het$^{108}$ | H | O | C(O)tBu | I | |
| 462 | Het$^{108}$ | H | O | C(O)Ph | I | |
| 463 | Het$^{108}$ | H | CO | Ph | Br | |
| 484 | Het$^{108}$ | H | CO | 4-C$_6$H$_4$OC(O)Ph | Br | |
| 465 | Het$^{109}$ | H | O | C(O)tBu | I | |
| 466 | Het$^{109}$ | H | O | C(O)Ph | I | |
| 467 | Het$^{109}$ | H | CO | Ph | Br | |
| 468 | Het$^{109}$ | H | CO | 4-C$_6$H$_4$OC(O)Ph | Br | |
| 469 | Het$^{110}$ | H | O | C(O)tBu | I | |
| 470 | Het$^{110}$ | H | O | C(O)Ph | I | |
| 471 | Het$^{110}$ | H | CO | Ph | Br | |
| 472 | Het$^{110}$ | H | CO | 4-C$_6$H$_4$OC(O)Ph | Br | |
| 473 | Het$^{111}$ | H | O | C(O)tBu | I | |
| 474 | Het$^{111}$ | H | O | C(O)Ph | I | |
| 475 | Het$^{111}$ | H | CO | Ph | Br | |
| 476 | Het$^{111}$ | H | CO | 4-C$_6$H$_4$OC(O)Ph | Br | |
| 477 | Het$^{112}$ | H | O | C(O)tBu | I | |
| 478 | Het$^{112}$ | H | O | C(O)Ph | I | |
| 479 | Het$^{112}$ | H | CO | Ph | Br | |
| 480 | Het$^{112}$ | H | CO | 4-C$_6$H$_4$OC(O)Ph | Br | |
| 481 | Het$^{113}$ | H | O | C(O)tBu | I | |
| 482 | Het$^{113}$ | H | O | C(O)Ph | I | |
| 483 | Het$^{113}$ | H | CO | Ph | Br | |
| 484 | Het$^{113}$ | H | CO | 4-C$_6$H$_4$OC(O)Ph | Br | |
| 485 | Het$^{114}$ | H | O | C(O)tBu | I | |
| 486 | Het$^{114}$ | H | O | C(O)Ph | I | mp.: 178° C. |
| 487 | Het$^{114}$ | H | CO | Ph | Br | |
| 488 | Het$^{114}$ | H | CO | 4-C$_6$H$_4$OC(O)Ph | Br | |
| 489 | Het$^{115}$ | H | O | C(O)tBu | I | |
| 490 | Het$^{115}$ | H | O | C(O)Ph | I | |
| 491 | Het$^{115}$ | H | CO | Ph | Br | |
| 492 | Het$^{115}$ | H | CO | 4-C$_6$H$_4$OC(O)Ph | Br | |
| 493 | Het$^{116}$ | H | O | C(O)tBu | I | |
| 494 | Het$^{116}$ | H | O | C(O)Ph | I | |
| 495 | Het$^{116}$ | H | CO | Ph | Br | |
| 496 | Het$^{116}$ | H | CO | 4-C$_6$H$_4$OC(O)Ph | Br | |
| 497 | Het$^{117}$ | H | O | C(O)tBu | I | |
| 498 | Het$^{117}$ | H | O | C(O)Ph | I | |
| 499 | Het$^{117}$ | H | CO | Ph | Br | |
| 500 | Het$^{117}$ | H | CO | 4-C$_6$H$_4$OC(O)Ph | Br | |
| 501 | Het$^{118}$ | H | O | C(O)tBu | I | |
| 502 | Het$^{118}$ | H | O | C(O)Ph | I | |
| 503 | Het$^{118}$ | H | CO | Ph | Br | |
| 504 | Het$^{118}$ | H | CO | 4-C$_6$H$_4$OC(O)Ph | Br | |
| 505 | Het$^{119}$ | H | O | C(O)tBu | I | |
| 506 | Het$^{119}$ | H | O | C(O)Ph | I | |
| 507 | Het$^{119}$ | H | CO | Ph | Br | |
| 508 | Het$^{119}$ | H | CO | 4-C$_6$H$_4$OC(O)Ph | Br | |
| 509 | Het$^{120}$ | H | O | C(O)tBu | I | |
| 510 | Het$^{120}$ | H | O | C(O)Ph | I | |
| 511 | Het$^{120}$ | H | CO | Ph | Br | |
| 512 | Het$^{120}$ | H | CO | 4-C$_6$H$_4$OC(O)Ph | Br | |
| 513 | Het$^{121}$ | H | O | C(O)tBu | I | |
| 514 | Het$^{121}$ | H | O | C(O)Ph | I | |
| 515 | Het$^{121}$ | H | CO | Ph | Br | |
| 516 | Het$^{121}$ | H | CO | 4-C$_6$H$_4$OC(O)Ph | Br | |
| 517 | Het$^{122}$ | H | O | C(O)tBu | I | |
| 518 | Het$^{122}$ | H | O | C(O)Ph | I | |
| 519 | Het$^{122}$ | H | CO | Ph | Br | |
| 520 | Het$^{122}$ | H | CO | 4-C$_6$H$_4$OC(O)Ph | Br | |
| 521 | Het$^{123}$ | H | O | C(O)tBu | I | |
| 522 | Het$^{123}$ | H | O | C(O)Ph | I | |
| 523 | Het$^{123}$ | H | CO | Ph | Br | |
| 524 | Het$^{123}$ | H | CO | 4-C$_6$H$_4$OC(O)Ph | Br | |
| 525 | Het$^{124}$ | H | O | C(O)tBu | I | |
| 526 | Het$^{124}$ | H | O | C(O)Ph | I | amorphous |
| 527 | Het$^{124}$ | H | CO | Ph | Br | |
| 528 | Het$^{124}$ | H | CO | 4-C$_6$H$_4$OC(O)Ph | Br | mp.: 199–202° C. |
| 529 | Het$^{125}$ | H | O | C(O)tBu | I | |
| 530 | Het$^{125}$ | H | O | C(O)Ph | I | |
| 531 | Het$^{125}$ | H | CO | Ph | Br | |
| 532 | Het$^{125}$ | H | CO | 4-C$_6$H$_4$OC(O)Ph | Br | |
| 533 | Het$^{126}$ | H | O | C(O)tBu | I | |
| 534 | Het$^{126}$ | H | O | C(O)Ph | I | |
| 535 | Het$^{126}$ | H | CO | Ph | Br | |
| 536 | Het$^{126}$ | H | CO | 4-C$_6$H$_4$OC(O)Ph | Br | |
| 537 | Het$^{127}$ | H | O | C(O)tBu | I | |
| 538 | Het$^{127}$ | H | O | C(O)Ph | I | |
| 539 | Het$^{127}$ | H | CO | Ph | Br | |
| 540 | Het$^{127}$ | H | CO | 4-C$_6$H$_4$OC(O)Ph | Br | |
| 541 | Het$^{128}$ | H | O | C(O)tBu | I | |
| 542 | Het$^{128}$ | H | O | C(O)Ph | I | |
| 543 | Het$^{128}$ | H | CO | Ph | Br | |
| 544 | Het$^{128}$ | H | CO | 4-C$_6$H$_4$OC(O)Ph | Br | |
| 545 | Het$^{129}$ | H | O | C(O)tBu | I | |
| 546 | Het$^{129}$ | H | O | C(O)Ph | I | |
| 547 | Het$^{129}$ | H | CO | Ph | Br | |
| 548 | Het$^{129}$ | H | CO | 4-C$_6$H$_4$OC(O)Ph | Br | |
| 549 | Het$^{130}$ | H | O | C(O)tBu | I | |
| 550 | Het$^{130}$ | H | O | C(O)Ph | I | |
| 551 | Het$^{130}$ | H | CO | Ph | Br | |
| 552 | Het$^{130}$ | H | CO | 4-C$_6$H$_4$OC(O)Ph | Br | |
| 553 | Het$^{131}$ | H | O | C(O)tBu | I | |
| 554 | Het$^{131}$ | H | O | C(O)Ph | I | |
| 555 | Het$^{131}$ | H | CO | Ph | Br | |
| 556 | Het$^{131}$ | H | CO | 4-C$_6$H$_4$OC(O)Ph | Br | |
| 557 | Het$^{132}$ | H | O | C(O)tBu | I | |
| 558 | Het$^{132}$ | H | O | C(O)Ph | I | |
| 559 | Het$^{132}$ | H | CO | Ph | Br | |

TABLE 1-continued $$[Het^n-CH-E-R^6]^+ \quad Q^-$$
$$\phantom{xxxxxx}|$$
$$\phantom{xxxxxx}R^5$$

| Ex. No. | $Het^n$ | $R^5$ | E | $R^6$ | Q | Phys. properties |
|---|---|---|---|---|---|---|
| 560 | $Het^{132}$ | H | CO | $4\text{-}C_6H_4OC(O)Ph$ | Br | |
| 561 | $Het^{133}$ | H | O | $C(O)tBu$ | I | |
| 562 | $Het^{133}$ | H | O | $C(O)Ph$ | I | |
| 563 | $Het^{133}$ | H | CO | Ph | Br | |
| 564 | $Het^{133}$ | H | CO | $4\text{-}C_6H_4OC(O)Ph$ | Br | |
| 565 | $Het^{134}$ | H | O | $C(O)tBu$ | I | |
| 566 | $Het^{134}$ | H | O | $C(O)Ph$ | I | |
| 567 | $Het^{134}$ | H | CO | Ph | Br | |
| 568 | $Het^{134}$ | H | CO | $4\text{-}C_6H_4OC(O)Ph$ | Br | |
| 569 | $Het^{135}$ | H | O | $C(O)tBu$ | I | |
| 570 | $Het^{135}$ | H | O | $C(O)Ph$ | I | |
| 571 | $Het^{135}$ | H | CO | Ph | Br | |
| 572 | $Het^{135}$ | H | CO | $4\text{-}C_6H_4OC(O)Ph$ | Br | |
| 573 | $Het^{136}$ | H | O | $C(O)tBu$ | I | |
| 574 | $Het^{136}$ | H | O | $C(O)Ph$ | I | |
| 575 | $Het^{136}$ | H | CO | Ph | Br | |
| 576 | $Het^{136}$ | H | CO | $4\text{-}C_6H_4OC(O)Ph$ | Br | |
| 577 | $Het^{137}$ | H | O | $C(O)tBu$ | I | |
| 578 | $Het^{137}$ | H | O | $C(O)Ph$ | I | |
| 579 | $Het^{137}$ | H | CO | Ph | Br | |
| 580 | $Het^{137}$ | H | CO | $4\text{-}C_6H_4OC(O)Ph$ | Br | |
| 581 | $Het^{138}$ | H | O | $C(O)tBu$ | I | |
| 562 | $Het^{138}$ | H | O | $C(O)Ph$ | I | |
| 583 | $Het^{138}$ | H | CO | Ph | Br | |
| 584 | $Het^{138}$ | H | CO | $4\text{-}C_6H_4OC(O)Ph$ | Br | |
| 585 | $Het^{139}$ | H | O | $C(O)tBu$ | I | |
| 586 | $Het^{139}$ | H | O | $C(O)Ph$ | I | |
| 587 | $Het^{139}$ | H | CO | Ph | Br | |
| 588 | $Het^{139}$ | H | CO | $4\text{-}C_6H_4OC(O)Ph$ | Br | |
| 589 | $Het^{140}$ | H | O | $C(O)tBu$ | I | |
| 590 | $Het^{140}$ | H | O | $C(O)Ph$ | I | |
| 591 | $Het^{140}$ | H | CO | Ph | Br | |
| 592 | $Het^{140}$ | H | CO | $4\text{-}C_6H_4OC(O)Ph$ | Br | |
| 593 | $Het^{141}$ | H | O | $C(O)tBu$ | I | |
| 594 | $Het^{141}$ | H | O | $C(O)Ph$ | I | |
| 595 | $Het^{141}$ | H | CO | Ph | Br | |
| 596 | $Het^{141}$ | H | CO | $4\text{-}C_6H_4OC(O)Ph$ | Br | |
| 597 | $Het^{142}$ | H | O | $C(O)tBu$ | I | |
| 598 | $Het^{142}$ | H | O | $C(O)Ph$ | I | |
| 599 | $Het^{142}$ | H | CO | Ph | Br | |
| 600 | $Het^{142}$ | H | CO | $4\text{-}C_6H_4OC(O)Ph$ | Br | |
| 601 | $Het^{143}$ | H | O | $C(O)tBu$ | I | |
| 602 | $Het^{143}$ | H | O | $C(O)Ph$ | I | |
| 603 | $Het^{143}$ | H | CO | Ph | Br | |
| 604 | $Het^{143}$ | H | CO | $4\text{-}C_6H_4OC(O)Ph$ | Br | |
| 605 | $Het^{144}$ | H | O | $C(O)tBu$ | I | |
| 606 | $Het^{144}$ | H | O | $C(O)Ph$ | I | |
| 607 | $Het^{144}$ | H | CO | Ph | Br | |
| 608 | $Het^{144}$ | H | CO | $4\text{-}C_6H_4OC(O)Ph$ | Br | |
| 609 | $Het^{145}$ | H | O | $C(O)tBu$ | I | |
| 610 | $Het^{145}$ | H | O | $C(O)Ph$ | I | |
| 611 | $Het^{145}$ | H | CO | Ph | Br | |
| 612 | $Het^{145}$ | H | CO | $4\text{-}C_6H_4OC(O)Ph$ | Br | |
| 613 | $Het^{146}$ | H | O | $C(O)tBu$ | I | |
| 614 | $Het^{146}$ | H | O | $C(O)Ph$ | I | |
| 615 | $Het^{146}$ | H | CO | Ph | Br | |
| 616 | $Het^{146}$ | H | CO | $4\text{-}C_6H_4OC(O)Ph$ | Br | |
| 617 | $Het^{147}$ | H | O | $C(O)tBu$ | I | |
| 618 | $Het^{147}$ | H | O | $C(O)Ph$ | I | |
| 619 | $Het^{147}$ | H | CO | Ph | Br | |
| 620 | $Het^{147}$ | H | CO | $4\text{-}C_6H_4OC(O)Ph$ | Br | |
| 621 | $Het^{148}$ | H | O | $C(O)tBu$ | I | |
| 622 | $Het^{148}$ | H | O | $C(O)Ph$ | I | |
| 623 | $Het^{148}$ | H | CO | Ph | Br | |
| 624 | $Het^{148}$ | H | CO | $4\text{-}C_6H_4OC(O)Ph$ | Br | |
| 625 | $Het^{149}$ | H | O | $C(O)tBu$ | I | |
| 626 | $Het^{149}$ | H | O | $C(O)Ph$ | I | |
| 627 | $Het^{149}$ | H | CO | Ph | Br | |
| 628 | $Het^{149}$ | H | CO | $4\text{-}C_6H_4OC(O)Ph$ | Br | |
| 629 | $Het^{150}$ | H | O | $C(O)tBu$ | I | |
| 630 | $Het^{150}$ | H | O | $C(O)Ph$ | I | |
| 631 | $Het^{150}$ | H | CO | Ph | Br | |
| 632 | $Het^{150}$ | H | CO | $4\text{-}C_6H_4OC(O)Ph$ | Br | |
| 633 | $Het^{151}$ | H | O | $C(O)tBu$ | I | |
| 634 | $Het^{151}$ | H | O | $C(O)Ph$ | I | |
| 635 | $Het^{151}$ | H | CO | Ph | Br | |
| 636 | $Het^{151}$ | H | CO | $4\text{-}C_6H_4OC(O)Ph$ | Br | |
| 637 | $Het^{152}$ | H | O | $C(O)tBu$ | I | |
| 638 | $Het^{152}$ | H | O | $C(O)Ph$ | I | |
| 639 | $Het^{152}$ | H | CO | Ph | Br | |
| 640 | $Het^{152}$ | H | CO | $4\text{-}C_6H_4OC(O)Ph$ | Br | |
| 641 | $Het^{153}$ | H | O | $C(O)tBu$ | I | |
| 642 | $Het^{153}$ | H | O | $C(O)Ph$ | I | |
| 643 | $Het^{153}$ | H | CO | Ph | Br | |
| 644 | $Het^{153}$ | H | CO | $4\text{-}C_6H_4OC(O)Ph$ | Br | |
| 645 | $Het^{154}$ | H | O | $C(O)tBu$ | I | |
| 646 | $Het^{154}$ | H | O | $C(O)Ph$ | I | |
| 647 | $Het^{154}$ | H | CO | Ph | Br | |
| 648 | $Het^{154}$ | H | CO | $4\text{-}C_6H_4OC(O)Ph$ | Br | |
| 649 | $Het^{155}$ | H | O | $C(O)tBu$ | I | |
| 650 | $Het^{155}$ | H | O | $C(O)Ph$ | I | |
| 651 | $Het^{155}$ | H | CO | Ph | Br | |
| 652 | $Het^{155}$ | H | CO | $4\text{-}C_6H_4OC(O)Ph$ | Br | |
| 653 | $Het^{156}$ | H | O | $C(O)tBu$ | I | |
| 654 | $Het^{156}$ | H | O | $C(O)Ph$ | I | |
| 655 | $Het^{156}$ | H | CO | Ph | Br | |
| 656 | $Het^{156}$ | H | CO | $4\text{-}C_6H_4OC(O)Ph$ | Br | |
| 657 | $Het^{157}$ | H | O | $C(O)tBu$ | I | |
| 658 | $Het^{157}$ | H | O | $C(O)Ph$ | I | |
| 659 | $Het^{157}$ | H | CO | Ph | Br | |
| 660 | $Het^{157}$ | H | CO | $4\text{-}C_6H_4OC(O)Ph$ | Br | |
| 661 | $Het^{158}$ | H | O | $C(O)tBu$ | I | |
| 662 | $Het^{158}$ | H | O | $C(O)Ph$ | I | |
| 663 | $Het^{158}$ | H | CO | Ph | Br | |
| 664 | $Het^{158}$ | H | CO | $4\text{-}C_6H_4OC(O)Ph$ | Br | |
| 665 | $Het^{159}$ | H | O | $C(O)tBu$ | I | |
| 666 | $Het^{159}$ | H | O | $C(O)Ph$ | I | |
| 667 | $Het^{159}$ | H | CO | Ph | Br | |
| 668 | $Het^{159}$ | H | CO | $4\text{-}C_6H_4OC(C)Ph$ | Br | |
| 669 | $Het^{160}$ | H | O | $C(O)tBu$ | I | |
| 670 | $Het^{160}$ | H | O | $C(O)Ph$ | I | |
| 671 | $Het^{160}$ | H | CO | Ph | Br | |
| 672 | $Het^{160}$ | H | CO | $4\text{-}C_6H_4OC(O)Ph$ | Br | |
| 673 | $Het^{161}$ | H | O | $C(O)tBu$ | I | |
| 674 | $Het^{161}$ | H | O | $C(O)Ph$ | I | |
| 675 | $Het^{161}$ | H | CO | Ph | Br | |
| 676 | $Het^{161}$ | H | CO | $4\text{-}C_6H_4OC(O)Ph$ | Br | |
| 677 | $Het^{162}$ | H | O | $C(O)tBu$ | I | |
| 678 | $Het^{162}$ | H | O | $C(O)Ph$ | I | |
| 679 | $Het^{162}$ | H | CO | Ph | Br | |
| 680 | $Het^{162}$ | H | CO | $4\text{-}C_6H_4OC(O)Ph$ | Br | |
| 681 | $Het^{163}$ | H | O | $C(O)tBu$ | I | |
| 682 | $Het^{163}$ | H | O | $C(O)Ph$ | I | |
| 683 | $Het^{163}$ | H | CO | Ph | Br | |
| 684 | $Het^{163}$ | H | CO | $4\text{-}C_6H_4OC(O)Ph$ | Br | |
| 685 | $Het^{164}$ | H | O | $C(O)tBu$ | I | |
| 686 | $Het^{164}$ | H | O | $C(O)Ph$ | I | |
| 687 | $Het^{164}$ | H | CO | Ph | Br | |
| 688 | $Het^{164}$ | H | CO | $4\text{-}C_6H_4OC(O)Ph$ | Br | |
| 689 | $Het^{165}$ | H | O | $C(O)tBu$ | I | |
| 690 | $Het^{165}$ | H | O | $C(O)Ph$ | I | |
| 691 | $Het^{165}$ | H | CO | Ph | Br | |
| 692 | $Het^{165}$ | H | CO | $4\text{-}C_6H_4OC(O)Ph$ | Br | |
| 693 | $Het^{166}$ | H | O | $C(O)tBu$ | I | |
| 694 | $Het^{166}$ | H | O | $C(O)Ph$ | I | |
| 695 | $Het^{166}$ | H | CO | Ph | Br | |
| 696 | $Het^{166}$ | H | CO | $4\text{-}C_6H_4OC(O)Ph$ | Br | |
| 697 | $Het^{167}$ | H | O | $C(O)tBu$ | I | |
| 698 | $Het^{167}$ | H | O | $C(O)Ph$ | I | |
| 699 | $Het^{167}$ | H | CO | Ph | Br | |
| 700 | $Het^{167}$ | H | CO | $4\text{-}C_6H_4OC(O)Ph$ | Br | |
| 701 | $Het^{168}$ | H | O | $C(O)tBu$ | I | |

TABLE 1-continued

[Het$^n$—CH(R$^5$)—E—R$^6$]$^+$ Q$^-$

| Ex. No. | Het$^n$ | R$^5$ | E | R$^6$ | Q | Phys. properties |
|---|---|---|---|---|---|---|
| 702 | Het$^{168}$ | H | O | C(O)Ph | I | |
| 703 | Het$^{168}$ | H | CO | Ph | Br | |
| 704 | Het$^{168}$ | H | CO | 4-C$_6$H$_4$OC(O)Ph | Br | |
| 705 | Het$^{169}$ | H | O | C(O)tBu | I | |
| 706 | Het$^{169}$ | H | O | C(O)Ph | I | |
| 707 | Het$^{169}$ | H | CO | Ph | Br | |
| 708 | Het$^{169}$ | H | CO | 4-C$_6$H$_4$OC(O)Ph | Br | |
| 709 | Het$^{170}$ | H | O | C(O)tBu | I | |
| 710 | Het$^{170}$ | H | O | C(O)Ph | I | |
| 711 | Het$^{170}$ | H | CO | Ph | Br | |
| 712 | Het$^{170}$ | H | CO | 4-C$_6$H$_4$OC(O)Ph | Br | |
| 713 | Het$^{171}$ | H | O | C(O)tBu | I | |
| 714 | Het$^{171}$ | H | O | C(O)Ph | I | |
| 715 | Het$^{171}$ | H | CO | Ph | Br | |
| 716 | Het$^{171}$ | H | CO | 4-C$_6$H$_4$OC(O)Ph | Br | |
| 717 | Het$^{172}$ | H | O | C(O)tBu | I | |
| 718 | Het$^{172}$ | H | O | C(O)Ph | I | |
| 719 | Het$^{172}$ | H | CO | Ph | Br | |
| 720 | Het$^{172}$ | H | CO | 4-C$_6$H$_4$OC(O)Ph | Br | |
| 721 | Het$^{173}$ | H | O | C(O)tBu | I | |
| 722 | Het$^{173}$ | H | O | C(O)Ph | I | |
| 723 | Het$^{173}$ | H | CO | Ph | Br | |
| 724 | Het$^{173}$ | H | CO | 4-C$_6$H$_4$OC(O)Ph | Br | |
| 725 | Het$^{174}$ | H | O | C(O)tBu | I | |
| 726 | Het$^{174}$ | H | O | C(O)Ph | I | |
| 727 | Het$^{174}$ | H | CO | Ph | Br | |
| 728 | Het$^{174}$ | H | CO | 4-C$_6$H$_4$OC(O)Ph | Br | |
| 729 | Het$^{175}$ | H | O | C(O)tBu | I | |
| 730 | Het$^{175}$ | H | O | C(O)Ph | I | |
| 731 | Het$^{175}$ | H | CO | Ph | Br | |
| 732 | Het$^{175}$ | H | CO | 4-C$_6$H$_4$OC(O)Ph | Br | |
| 733 | Het$^{176}$ | H | O | C(O)tBu | I | |
| 734 | Het$^{176}$ | H | O | C(O)Ph | I | |
| 735 | Het$^{176}$ | H | CO | Ph | Br | |
| 736 | Het$^{176}$ | H | CO | 4-C$_6$H$_4$OC(O)Ph | Br | |
| 737 | Het$^{177}$ | H | O | C(O)tBu | I | |
| 738 | Het$^{177}$ | H | O | C(O)Ph | I | |
| 739 | Het$^{177}$ | H | CO | Ph | Br | |
| 740 | Het$^{177}$ | H | CO | 4-C$_6$H$_4$OC(O)Ph | Br | |
| 741 | Het$^{178}$ | H | O | C(O)tBu | I | |
| 742 | Het$^{178}$ | H | O | C(O)Ph | I | |
| 743 | Het$^{178}$ | H | CO | Ph | Br | |
| 744 | Het$^{178}$ | H | CO | 4-C$_6$H$_4$OC(O)Ph | Br | |
| 745 | Het$^{179}$ | H | O | C(O)tBu | I | |
| 746 | Het$^{179}$ | H | O | C(O)Ph | I | |
| 747 | Het$^{179}$ | H | CO | Ph | Br | |
| 748 | Het$^{179}$ | H | CO | 4-C$_6$H$_4$OC(O)Ph | Br | |
| 749 | Het$^{180}$ | H | O | C(O)tBu | I | |
| 750 | Het$^{180}$ | H | O | C(O)Ph | I | |
| 751 | Het$^{180}$ | H | CO | Ph | Br | |
| 752 | Het$^{180}$ | H | CO | 4-C$_6$H$_4$OC(O)Ph | Br | |
| 753 | Het$^{181}$ | H | O | C(O)tBu | I | |
| 754 | Het$^{181}$ | H | O | C(O)Ph | I | |
| 755 | Het$^{181}$ | H | CO | Ph | Br | |
| 756 | Het$^{181}$ | H | CO | 4-C$_6$H$_4$OC(O)Ph | Br | |
| 757 | Het$^{182}$ | H | O | C(O)tBu | I | |
| 758 | Het$^{182}$ | H | O | C(O)Ph | I | |
| 759 | Het$^{182}$ | H | CO | Ph | Br | |
| 760 | Het$^{182}$ | H | CO | 4-C$_6$H$_4$OC(O)Ph | Br | |
| 761 | Het$^{183}$ | H | O | C(O)tBu | I | |
| 762 | Het$^{183}$ | H | O | C(O)Ph | I | |
| 763 | Het$^{183}$ | H | CO | Ph | Br | |
| 764 | Het$^{183}$ | H | CO | 4-C$_6$H$_4$OC(O)Ph | Br | |
| 765 | Het$^{184}$ | H | O | C(O)tBu | I | |
| 766 | Het$^{184}$ | H | O | C(O)Ph | I | |
| 767 | Het$^{184}$ | H | CO | Ph | Br | |
| 768 | Het$^{184}$ | H | CO | 4-C$_6$H$_4$OC(O)Ph | Br | |
| 769 | Het$^{185}$ | H | O | C(O)tBu | I | |
| 770 | Het$^{185}$ | H | O | C(O)Ph | I | |
| 771 | Het$^{185}$ | H | CO | Ph | Br | |
| 772 | Het$^{185}$ | H | CO | 4-C$_6$H$_4$OC(O)Ph | Br | |
| 773 | Het$^{186}$ | H | O | COC$_6$H$_5$ | I | mp.: 138° C. |
| 774 | Het$^{187}$ | H | CO | 4-C$_6$H$_4$O(CO)Ph | I | mp.: 184–185° C. |
| 775 | Het$^{188}$ | H | CO | 4-C$_6$H$_4$O(CO)Ph | I | mp.: 103–109° C. |
| 776 | Het$^{189}$ | H | CO | 4-C$_6$H$_4$O(CO)Ph | I | mp.: 193–194° C. |
| 777 | Het$^{190}$ | H | CO | 4-C$_6$H$_4$O(CO)Ph | I | mp.: 210° C. decomp. |
| 778 | Het$^{191}$ | H | CO | 4-C$_6$H$_4$O(CO)Ph | I | mp.: 235–237° C. |
| 779 | Het$^{192}$ | H | O | 4-C$_6$H$_4$O(CO)Ph | I | mp.: 207° C. |
| 780 | Het$^{192}$ | H | CO | 4-C$_6$H$_5$O(CO)Ph | Br | mp.: 148° C. |
| 781 | Het$^{193}$ | H | CO | 4-C$_6$H$_5$O(CO)Ph | Br | |
| 782 | Het$^{194}$ | H | CO | 4-C$_6$H$_5$O(CO)Ph | Br | |
| 783 | Het$^{195}$ | H | CO | 4-C$_6$H$_5$O(CO)Ph | Br | |
| 784 | Het$^{196}$ | H | CO | 4-C$_6$H$_5$O(CO)Ph | Br | |
| 785 | Het$^{197}$ | H | CO | 4-C$_6$H$_5$O(CO)Ph | Br | |
| 786 | Het$^{198}$ | H | CO | 4-C$_6$H$_5$O(CO)Ph | Br | |
| 787 | Het$^{199}$ | H | CO | 4-C$_6$H$_5$O(CO)Ph | Br | |
| 788 | Het$^{200}$ | H | CO | 4-C$_6$H$_5$O(CO)Ph | Br | |
| 789 | Het$^{201}$ | H | CO | 4-C$_6$H$_5$O(CO)Ph | Br | |
| 790 | Het$^{202}$ | H | CO | 4-C$_6$H$_5$O(CO)Ph | Br | |

Definition of the heterocycles Het$^n$

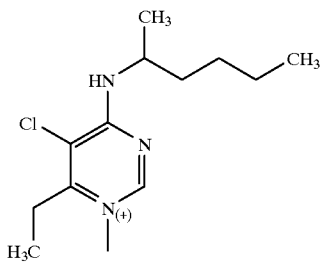

Het$^1$

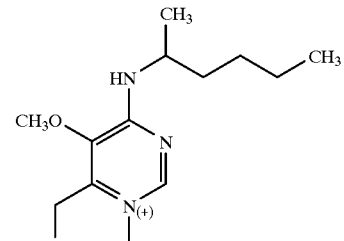

Het$^2$

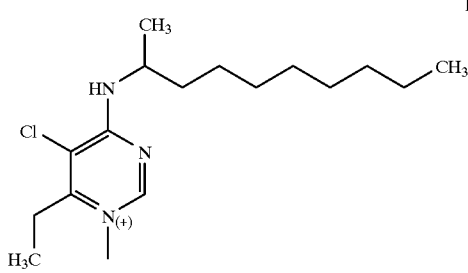

Het$^3$

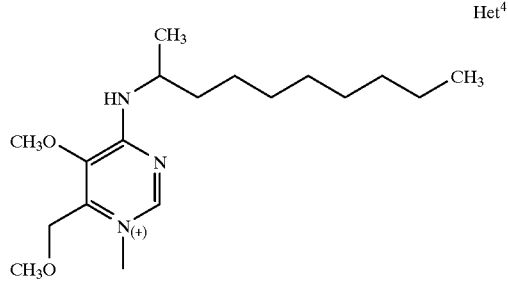
Het⁴
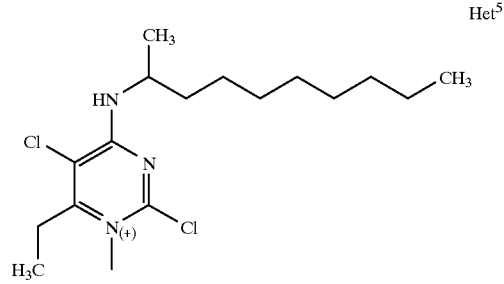
Het⁵
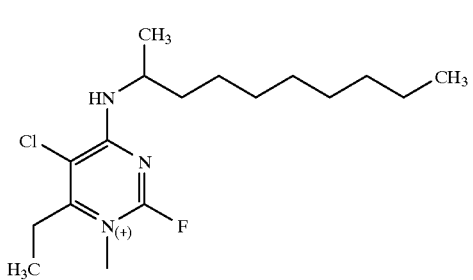
Het⁶
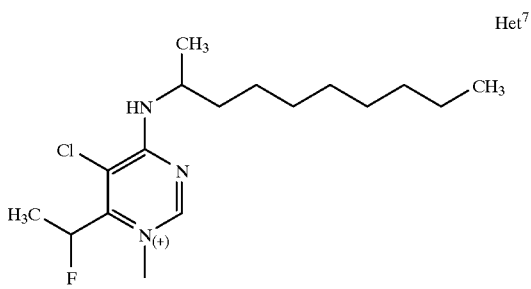
Het⁷
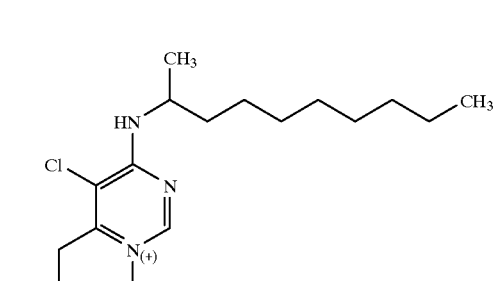
Het⁸
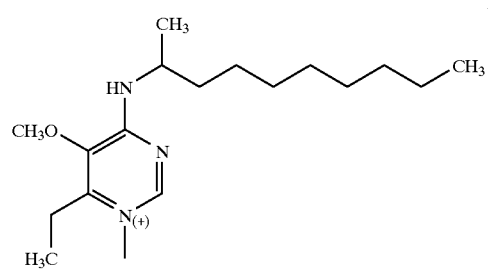
Het⁹
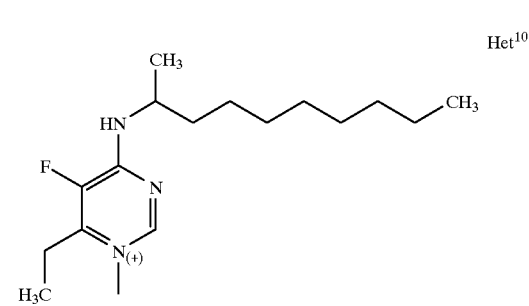
Het¹⁰
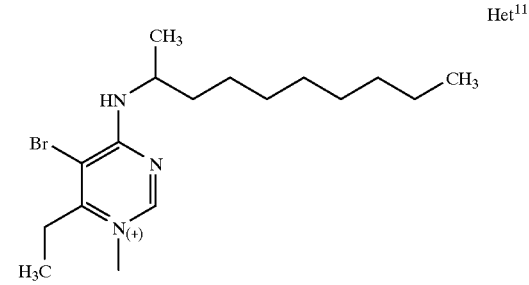
Het¹¹
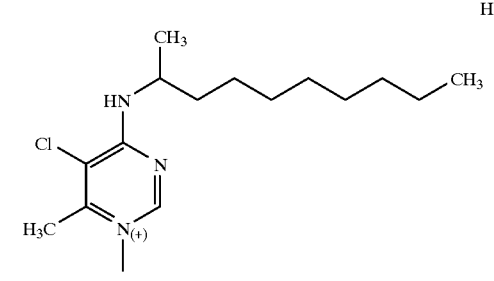
Het¹²
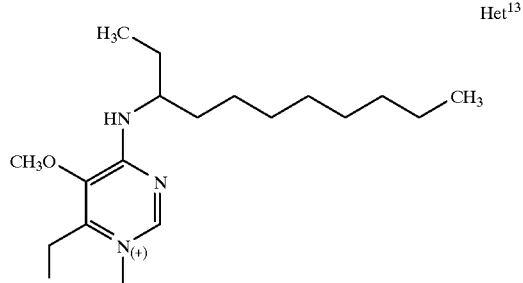
Het¹³

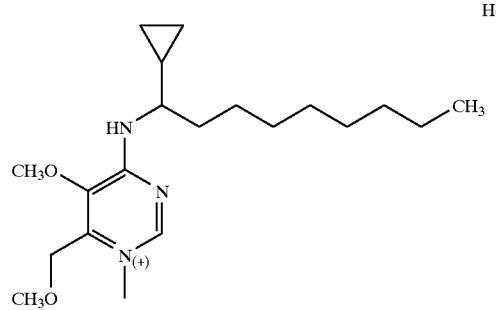
Het¹⁴
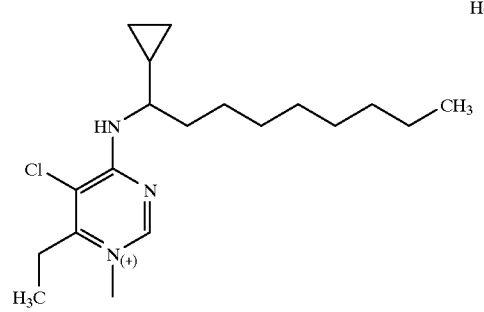
Het¹⁵
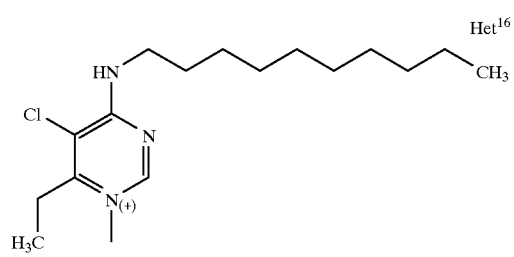
Het¹⁶
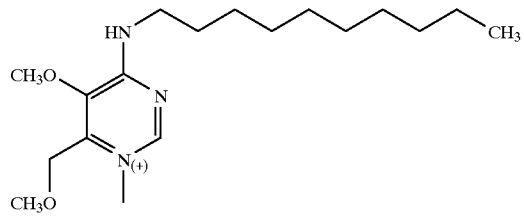
Het¹⁷
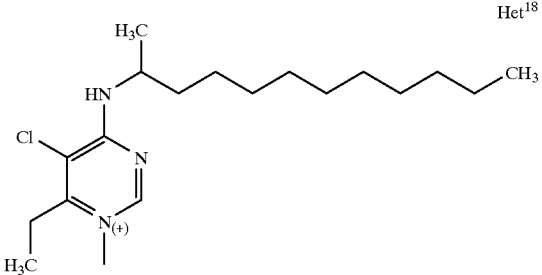
Het¹⁸
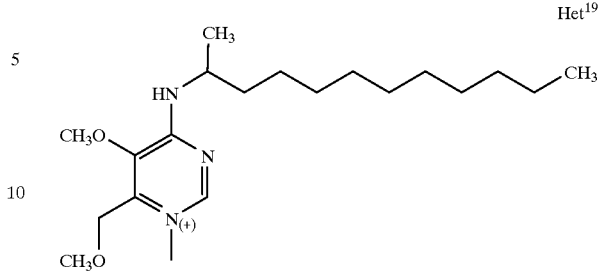
Het¹⁹
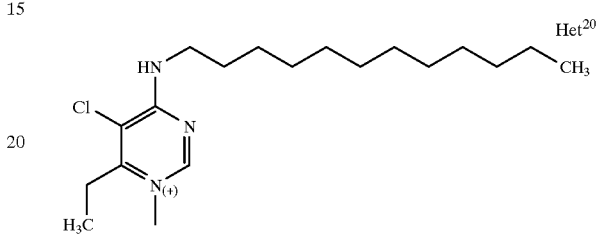
Het²⁰
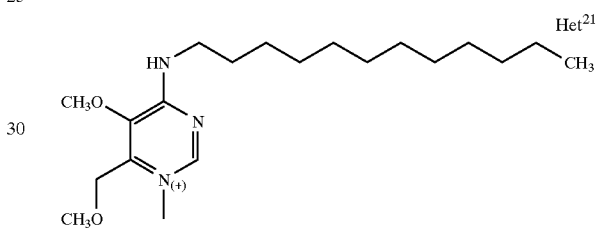
Het²¹
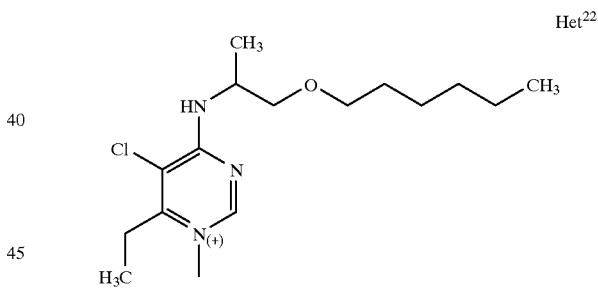
Het²²
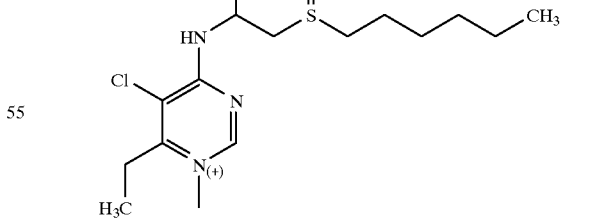
Het²³

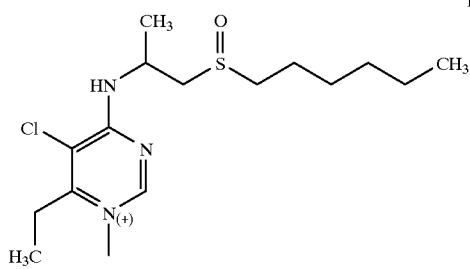
Het24
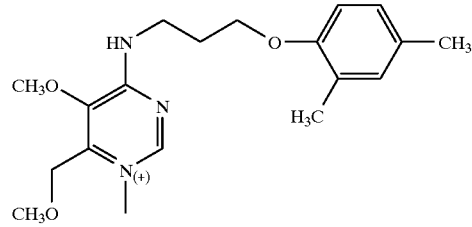
Het25
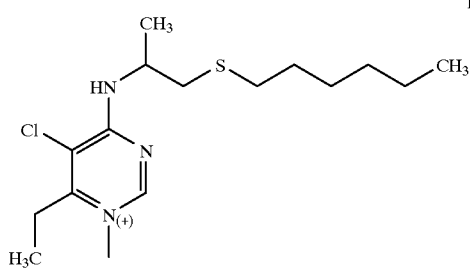
Het26
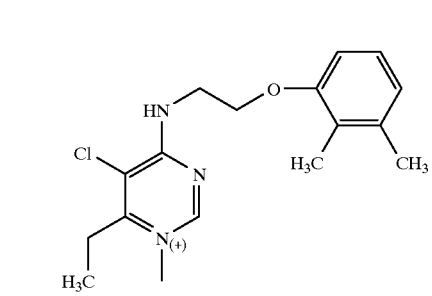
Het27
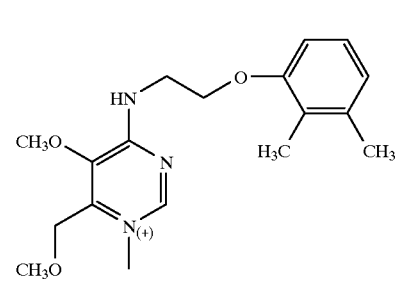
Het28
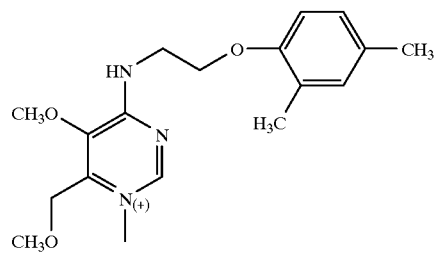
Het29
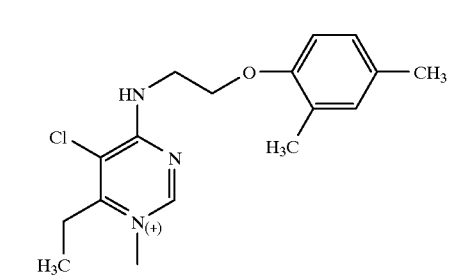
Het30
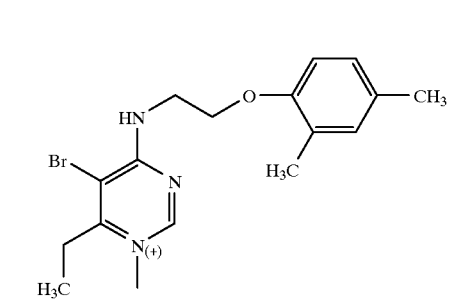
Het31
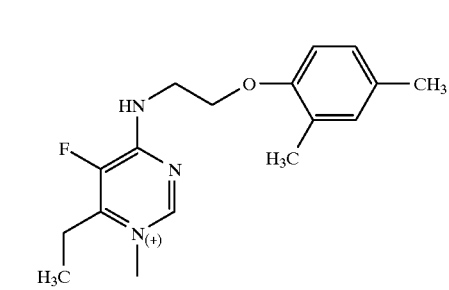
Het32
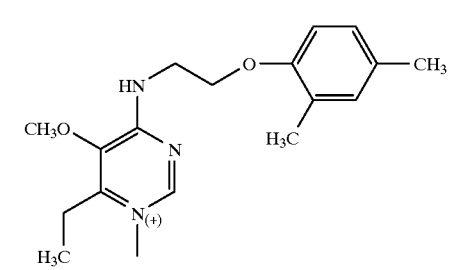
Het33

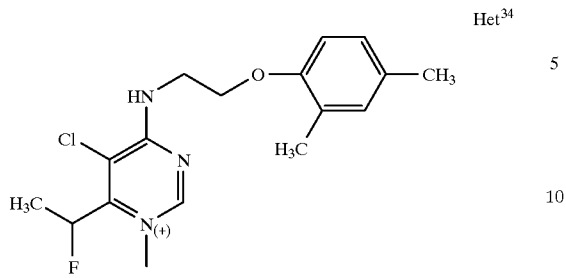
Het³⁴
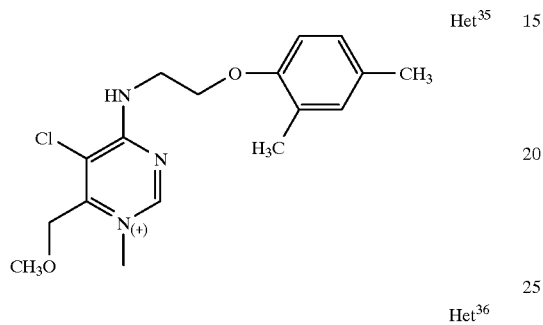
Het³⁵
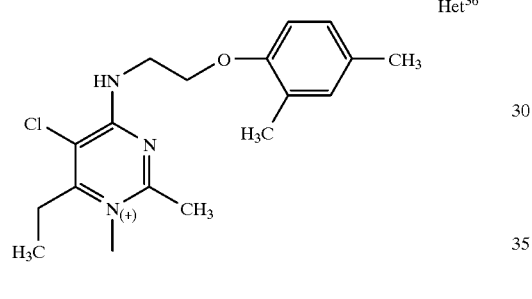
Het³⁶
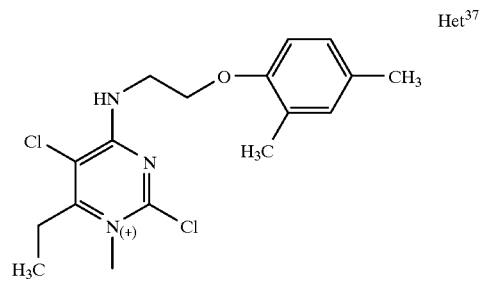
Het³⁷
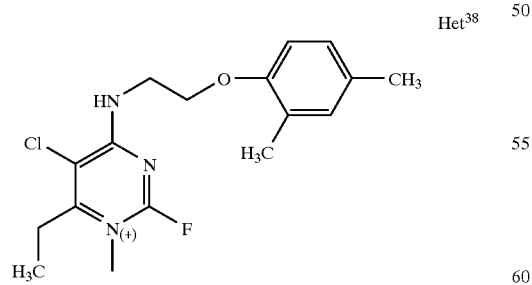
Het³⁸
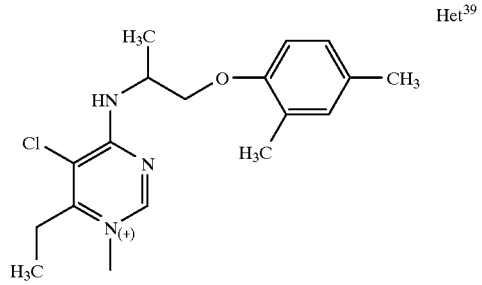
Het³⁹
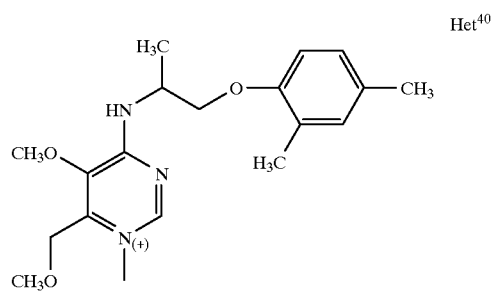
Het⁴⁰
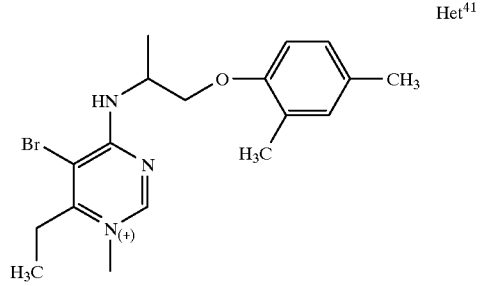
Het⁴¹
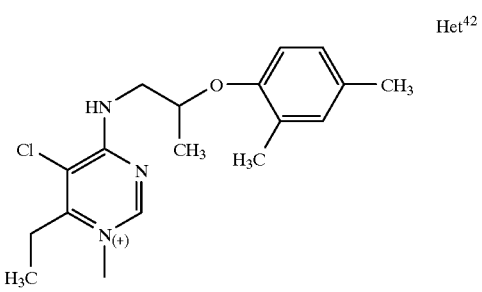
Het⁴²
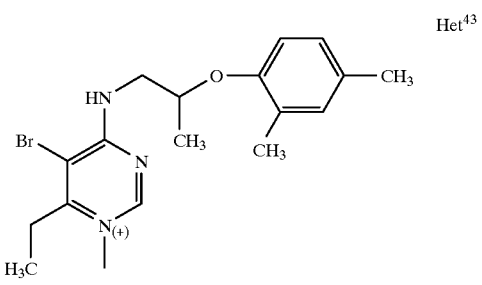
Het⁴³

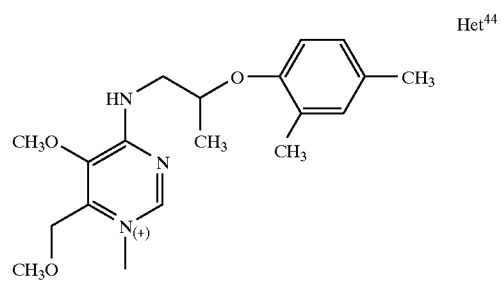
Het[44]
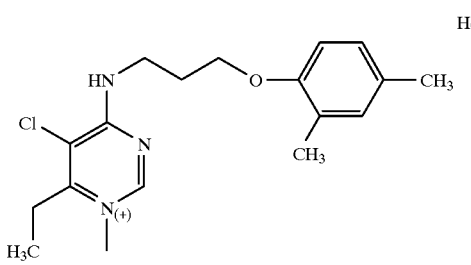
Het[45]
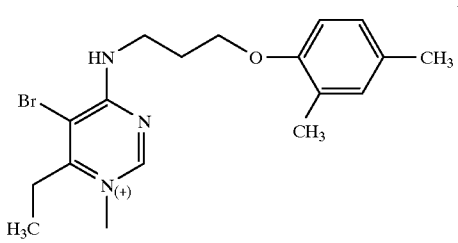
Het[46]
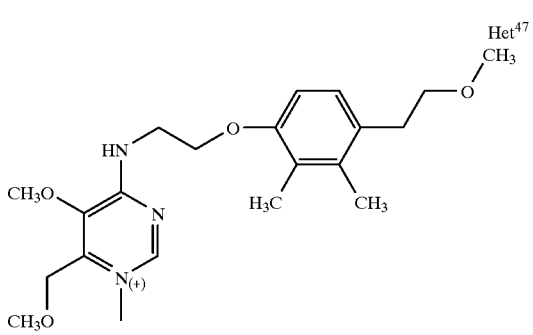
Het[47]
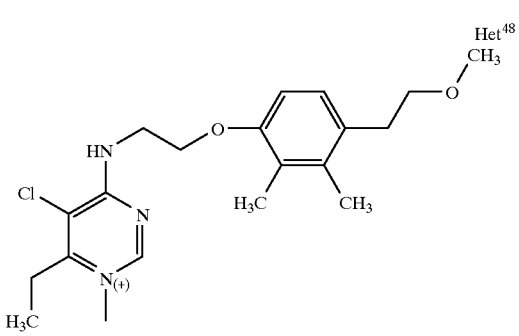
Het[48]
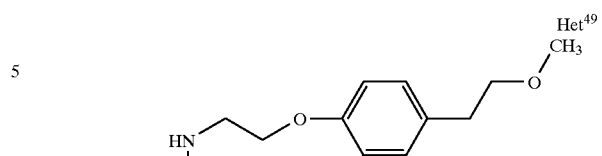
Het[49]
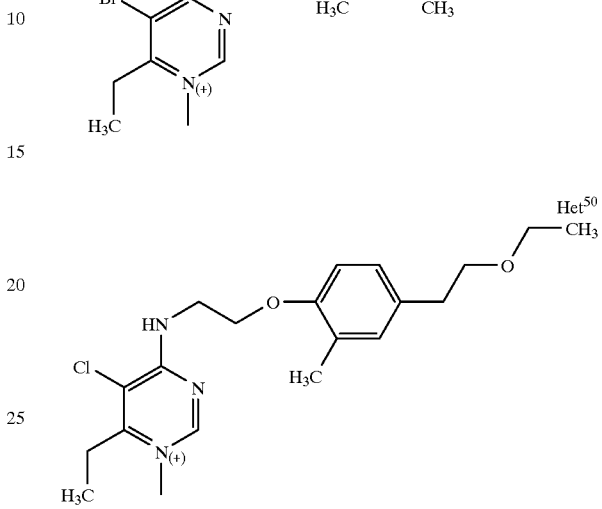
Het[50]
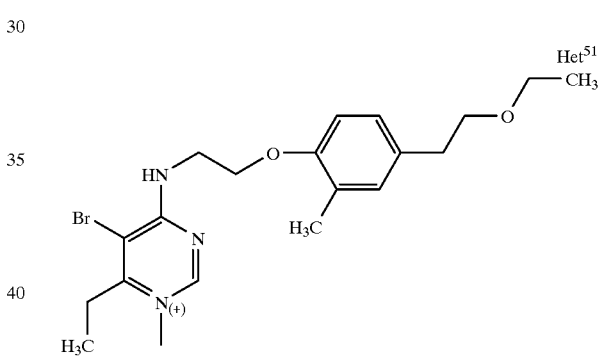
Het[51]
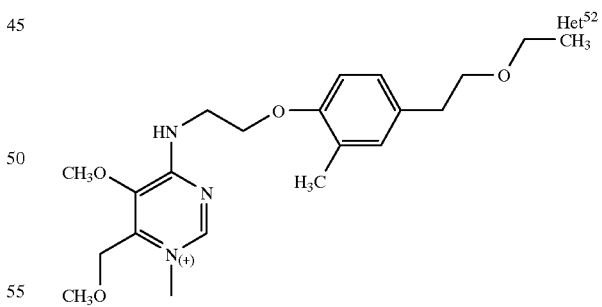
Het[52]

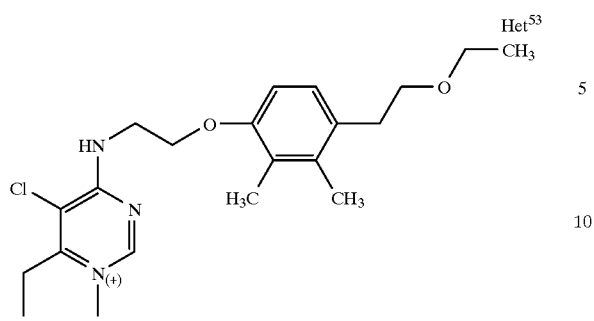
Het⁵³
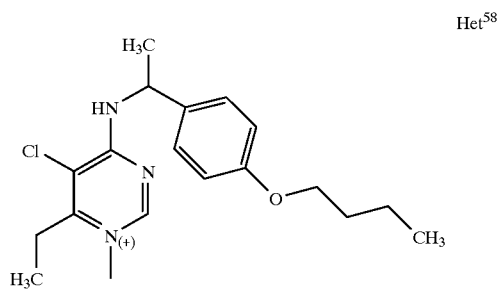
Het⁵⁸
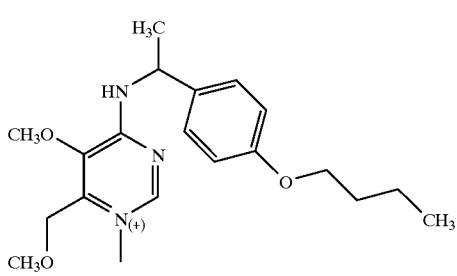
Het⁵⁹
Het⁵⁴
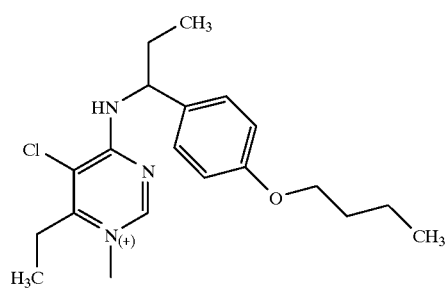
Het⁶⁰
Het⁵⁵
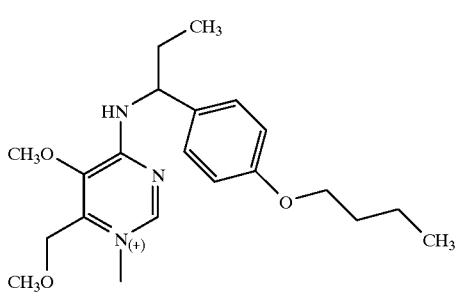
Het⁶¹
Het⁵⁶
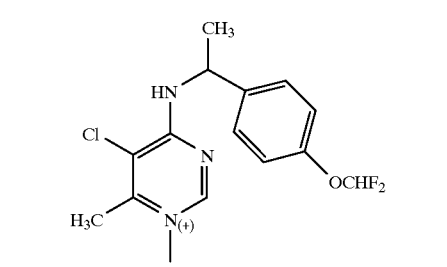
Het⁶²
Het⁵⁷

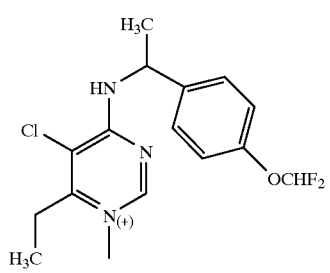 Het<sup>63</sup>
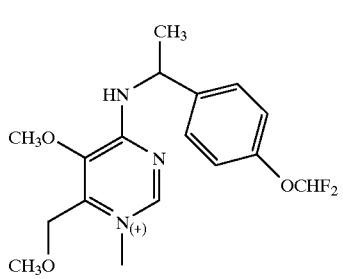 Het<sup>64</sup>
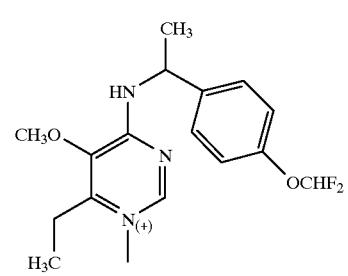 Het<sup>65</sup>
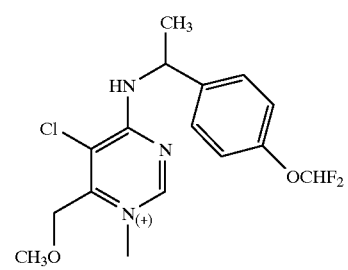 Het<sup>66</sup>
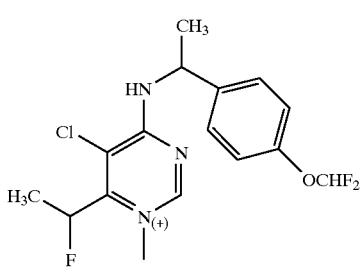 Het<sup>67</sup>
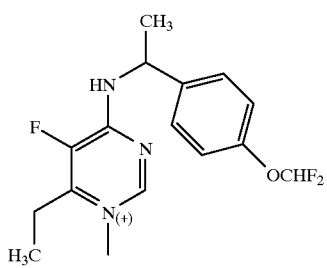 Het<sup>68</sup>
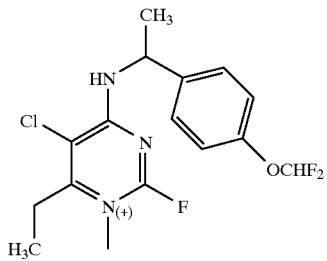 Het<sup>69</sup>
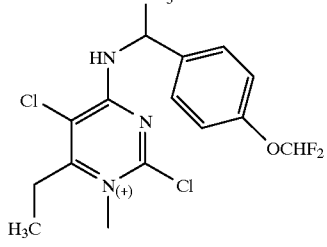 Het<sup>70</sup>
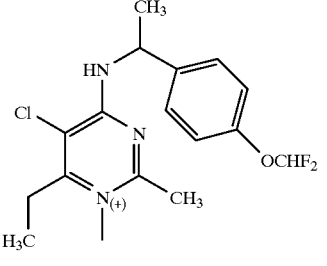 Het<sup>71</sup>
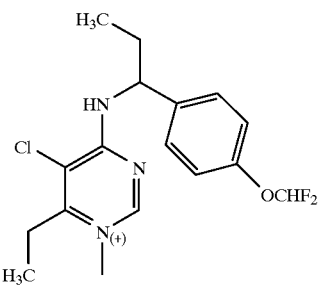 Het<sup>72</sup>

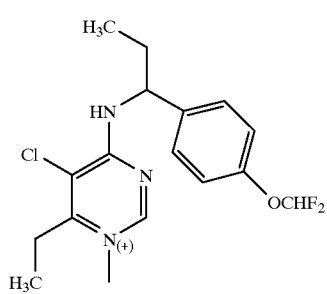 Het[73]
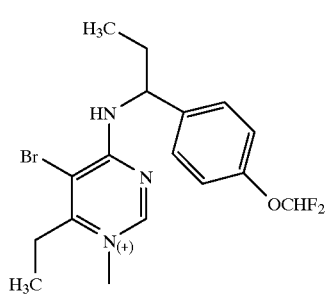 Het[74]
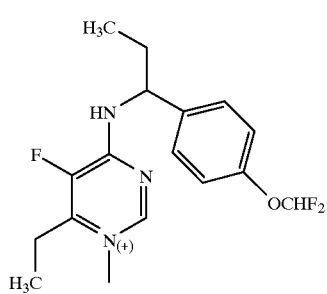 Het[75]
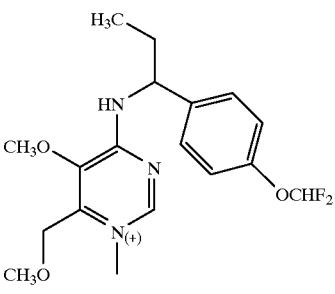 Het[76]
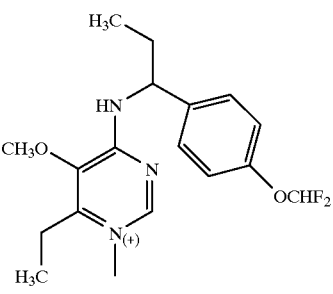 Het[77]
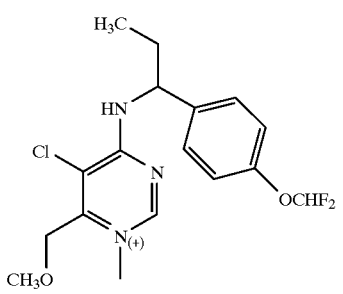 Het[78]
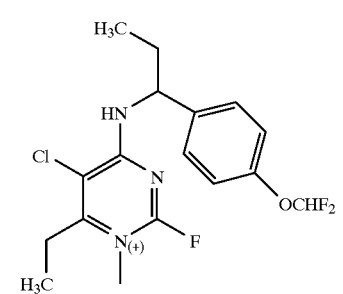 Het[79]
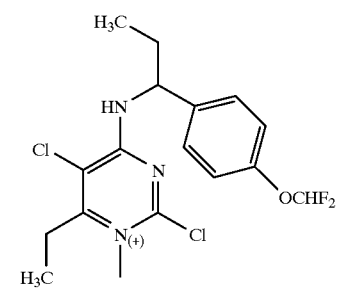 Het[80]
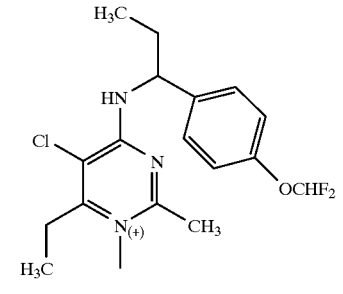 Het[81]
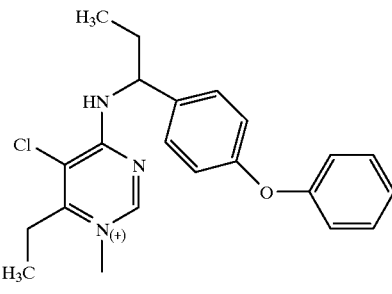 Het[82]

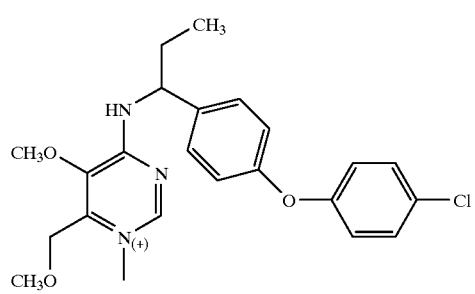 Het⁸³
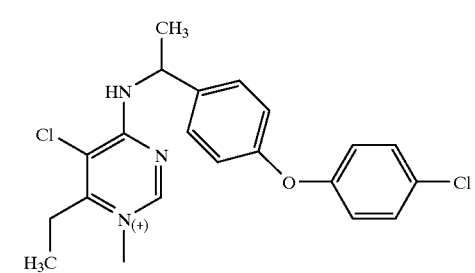 Het⁸⁴
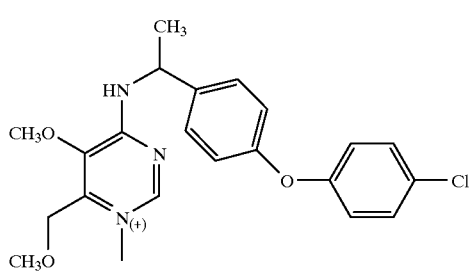 Het⁸⁵
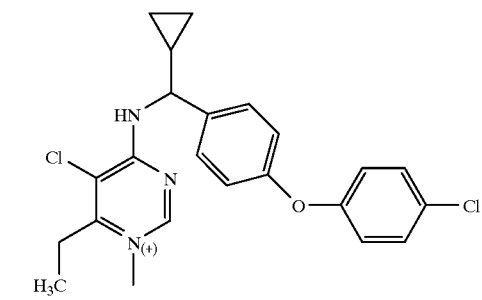 Het⁸⁶
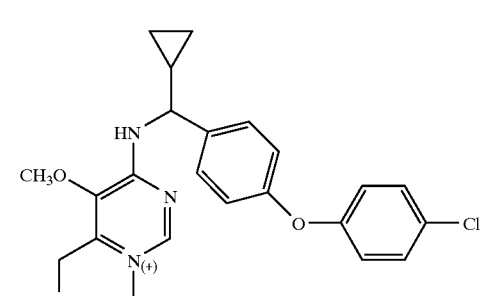 Het⁸⁷
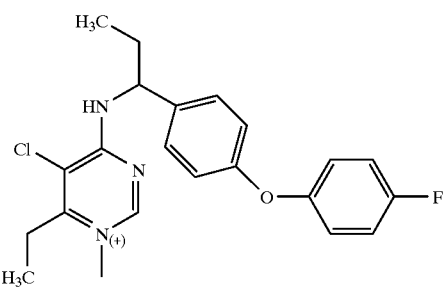 Het⁸⁸
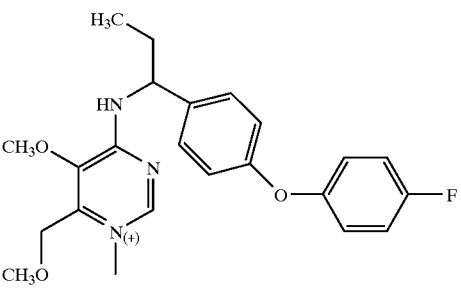 Het⁸⁹
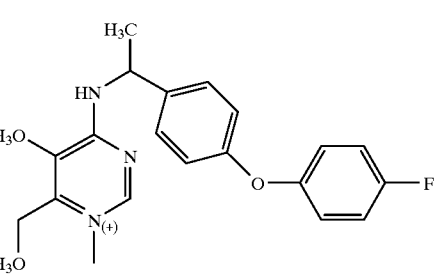 Het⁹⁰
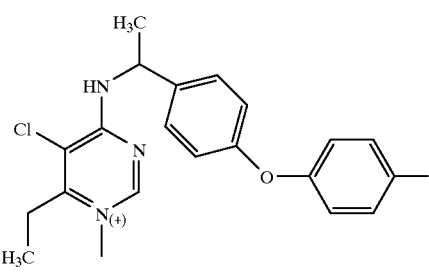 Het⁹¹
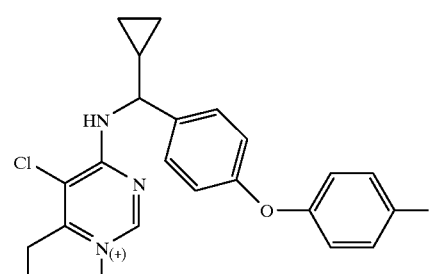 Het⁹²

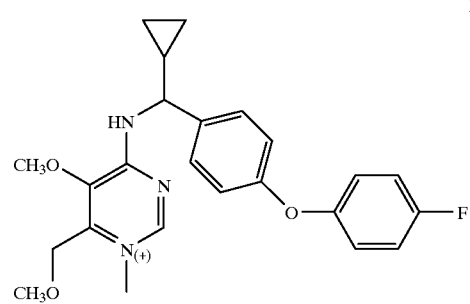
Het⁹³
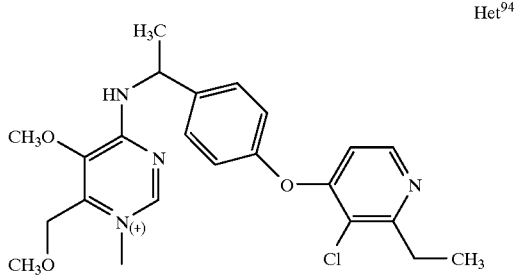
Het⁹⁴
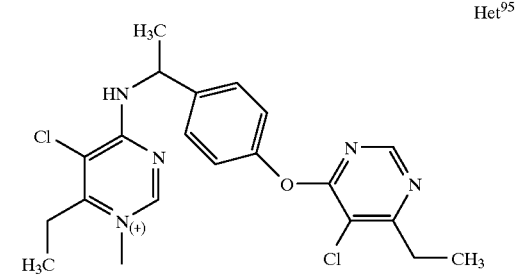
Het⁹⁵
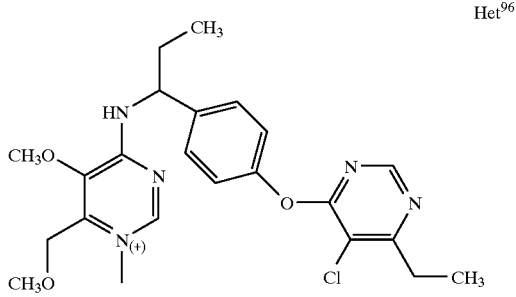
Het⁹⁶
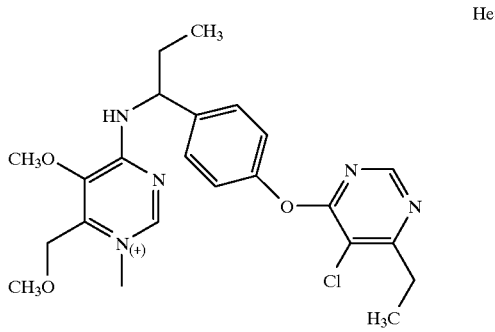
Het⁹⁷
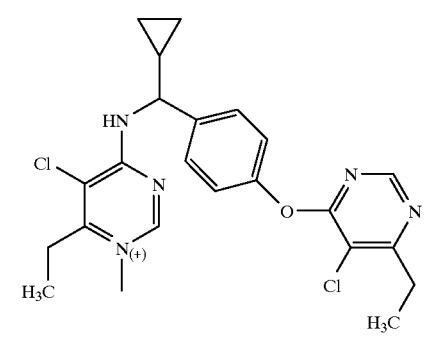
Het⁹⁸
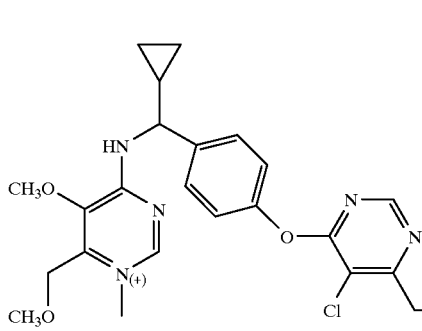
Het⁹⁹
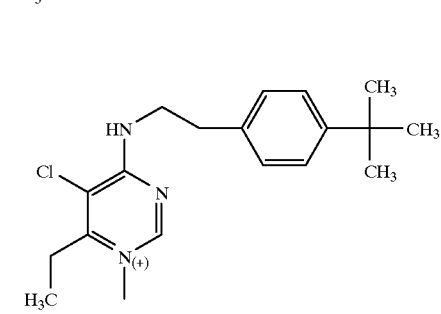
Het¹⁰⁰
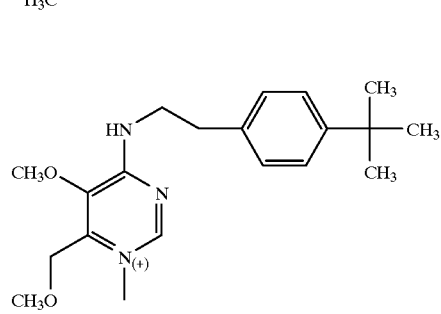
Het¹⁰¹
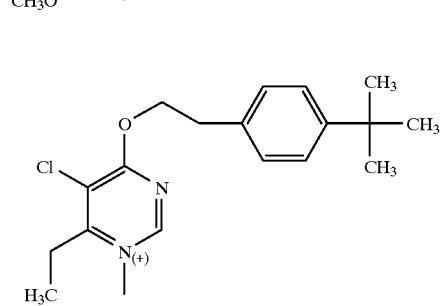
Het¹⁰²

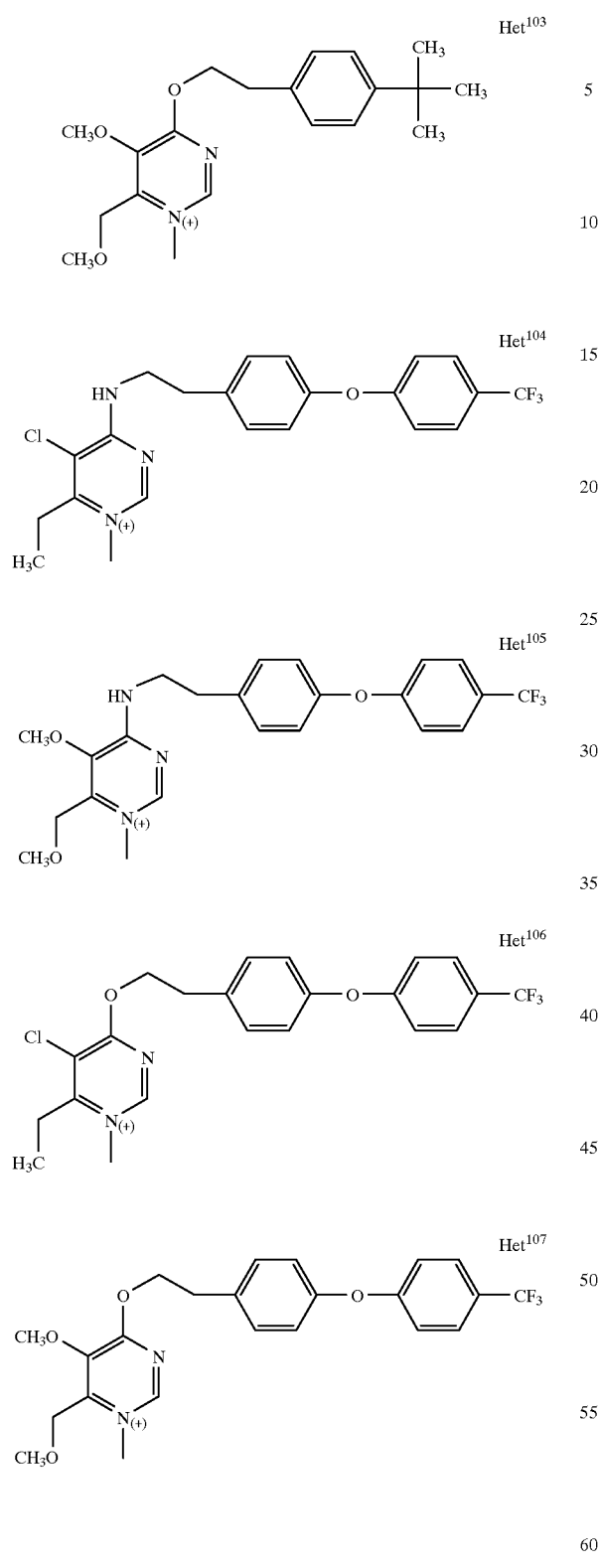
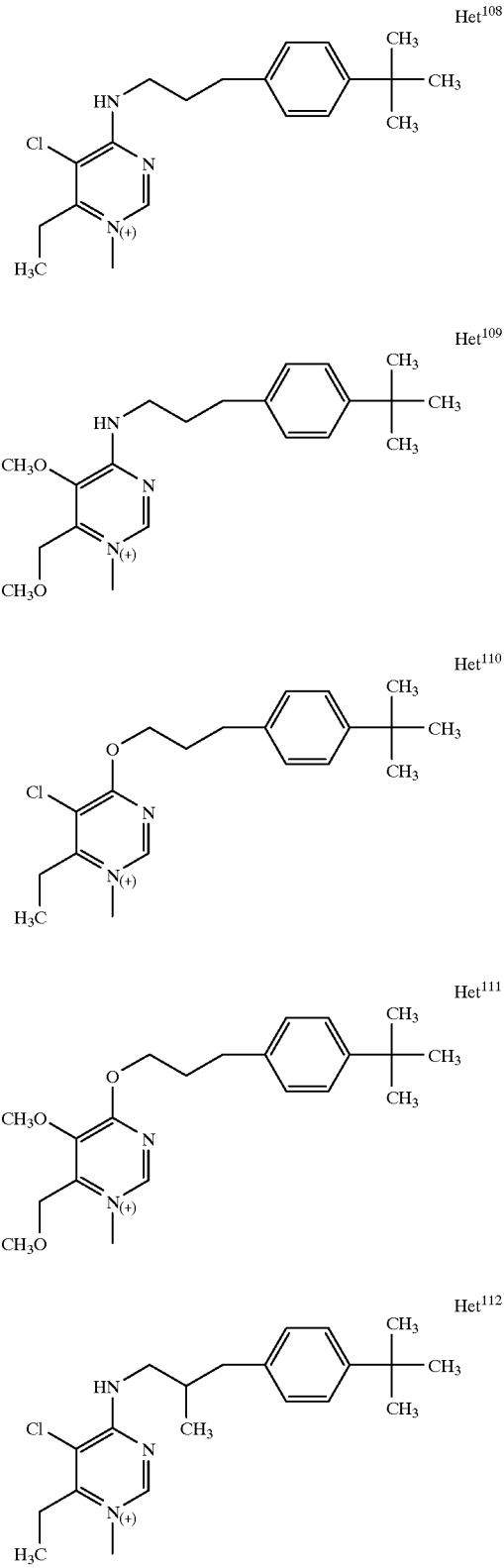

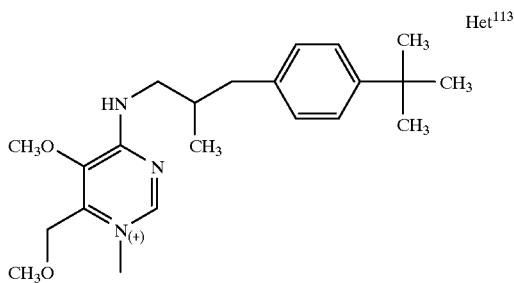 Het^113
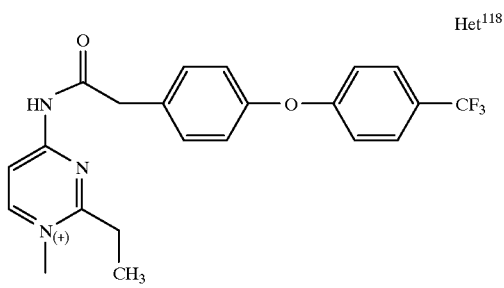 Het^118
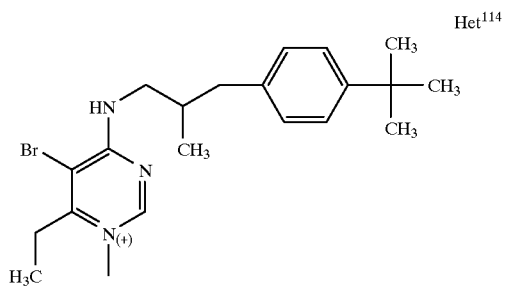 Het^114
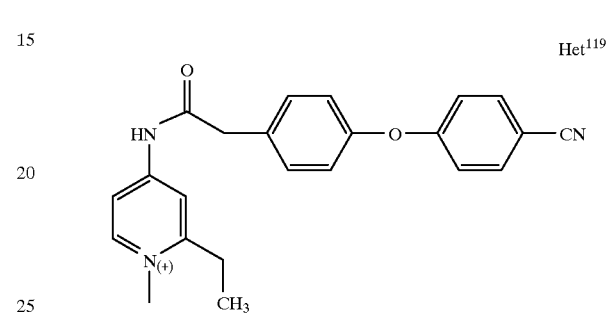 Het^119
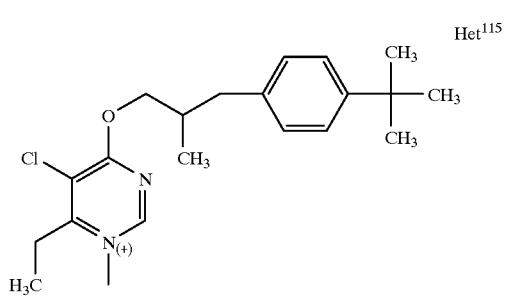 Het^115
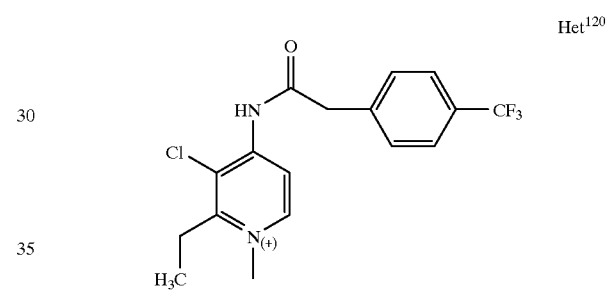 Het^120
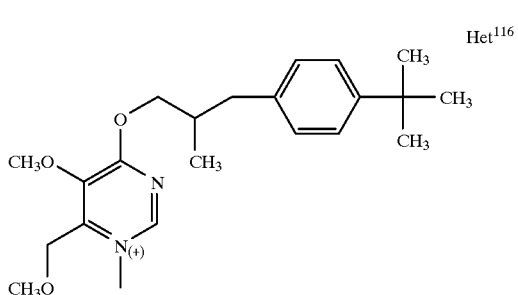 Het^116
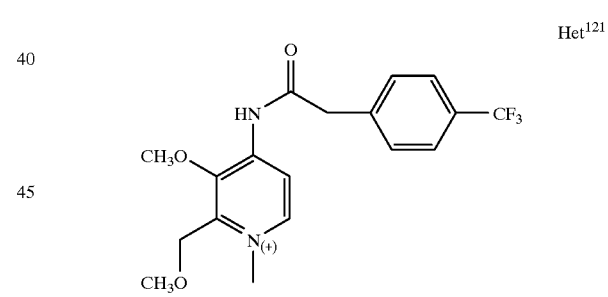 Het^121
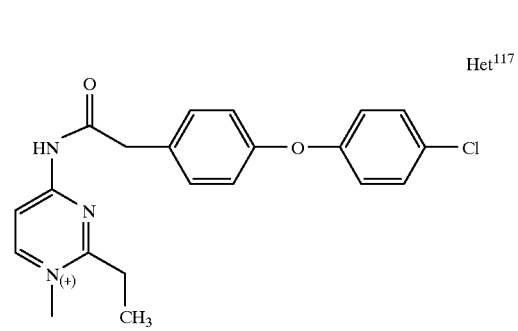 Het^117
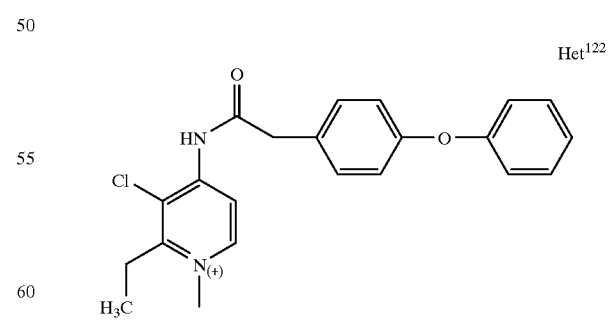 Het^122

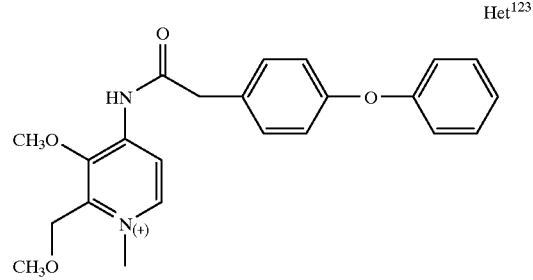
Het¹²³
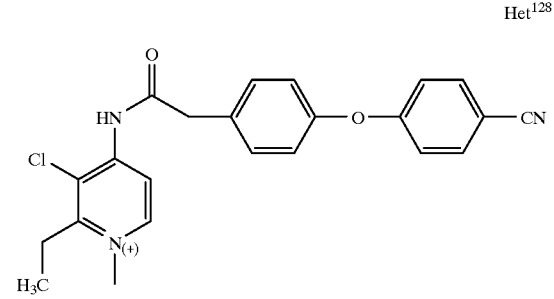
Het¹²⁸
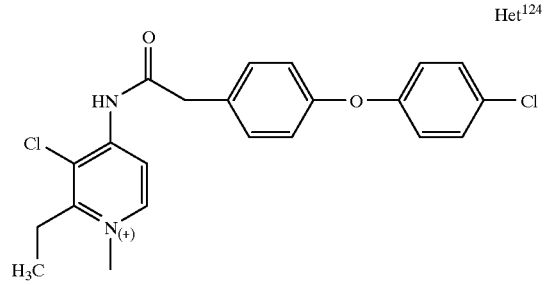
Het¹²⁴
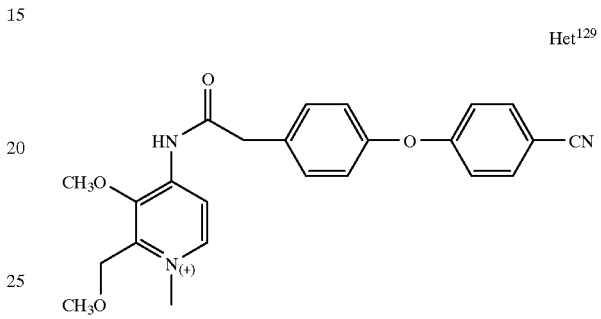
Het¹²⁹
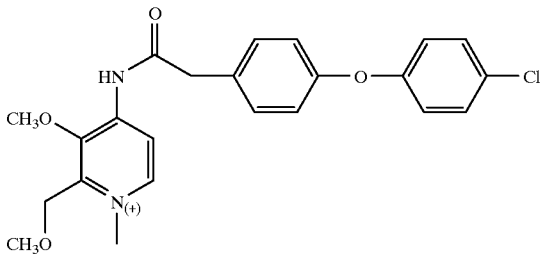
Het¹²⁵
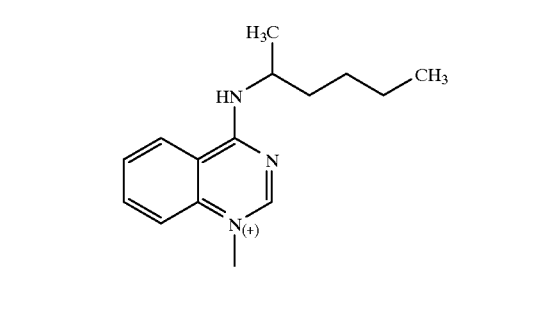
Het¹³⁰
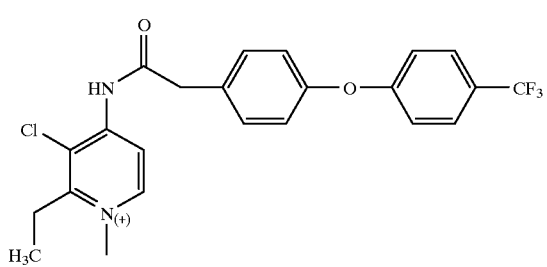
Het¹²⁶
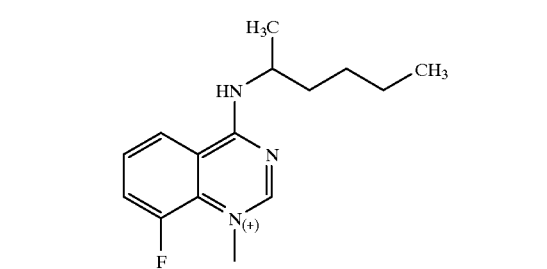
Het¹³¹
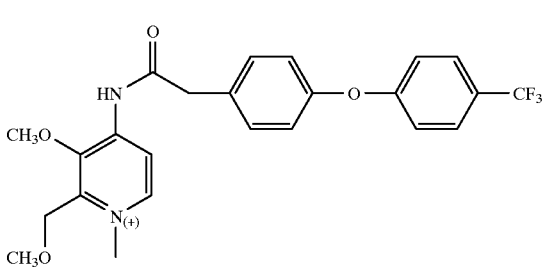
Het¹²⁷
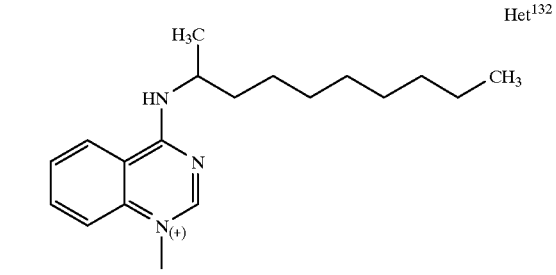
Het¹³²

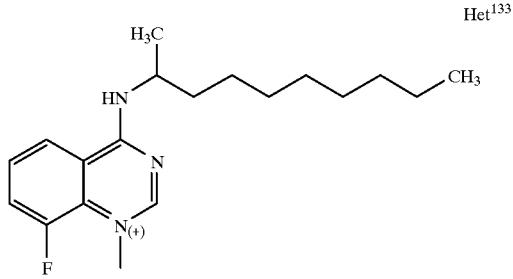
Het¹³³
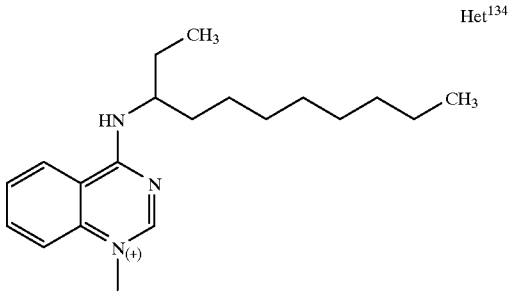
Het¹³⁴
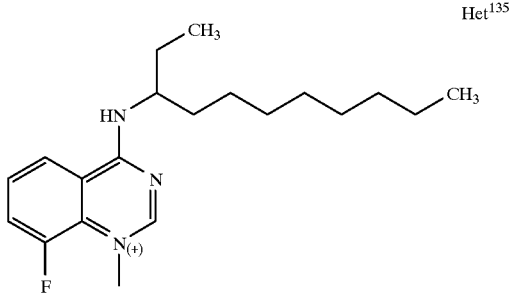
Het¹³⁵
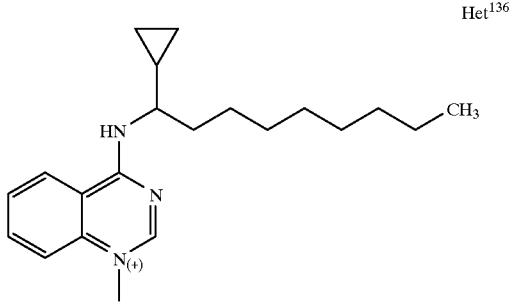
Het¹³⁶
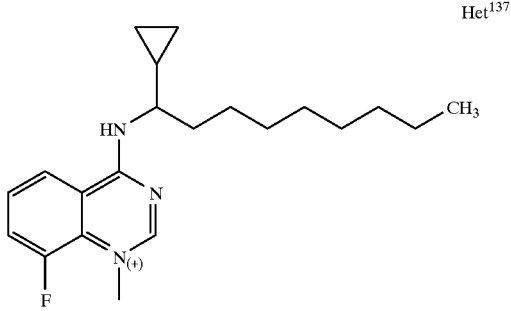
Het¹³⁷
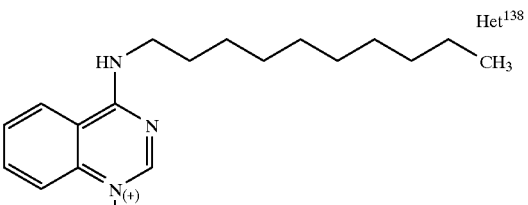
Het¹³⁸
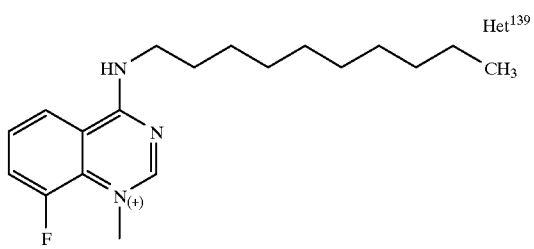
Het¹³⁹
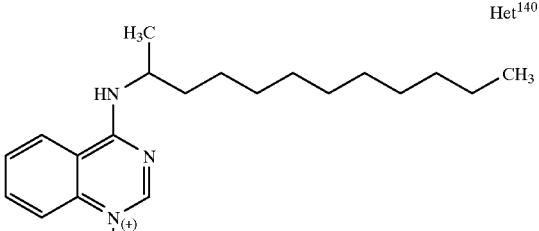
Het¹⁴⁰
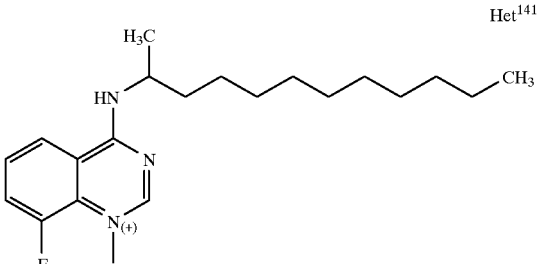
Het¹⁴¹
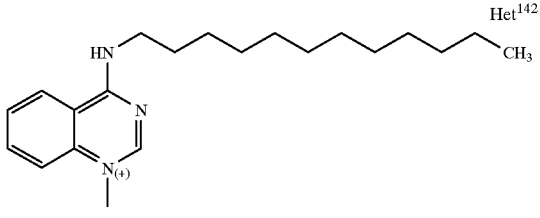
Het¹⁴²
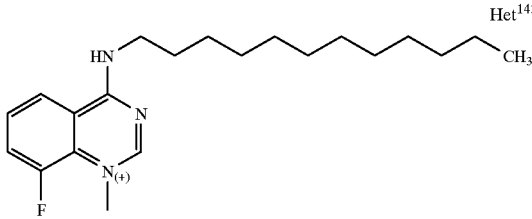
Het¹⁴³

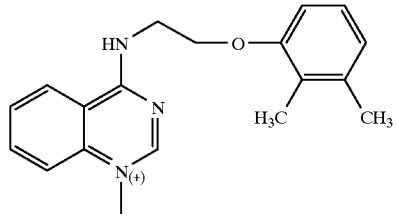
Het144
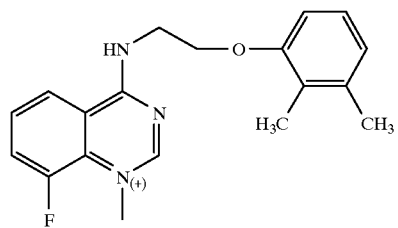
Het145
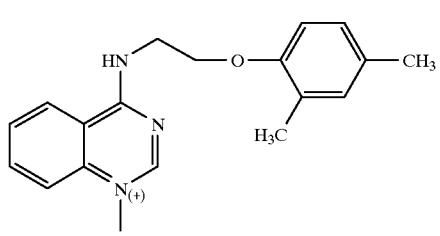
Het146
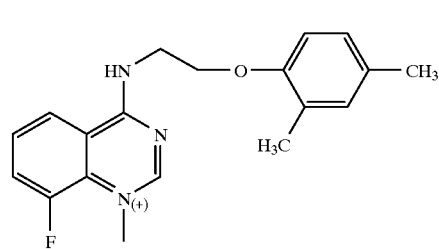
Het147
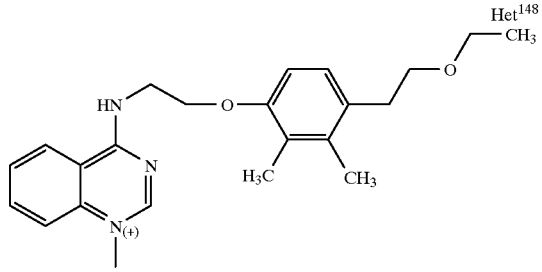
Het148
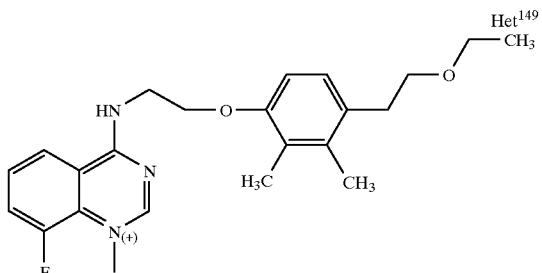
Het149
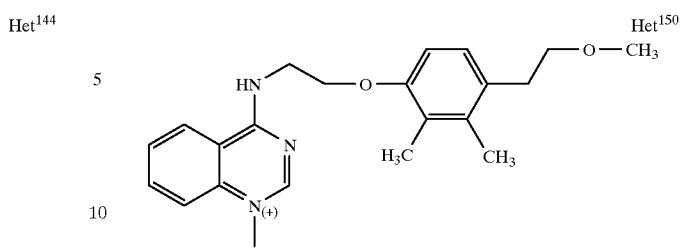
Het150
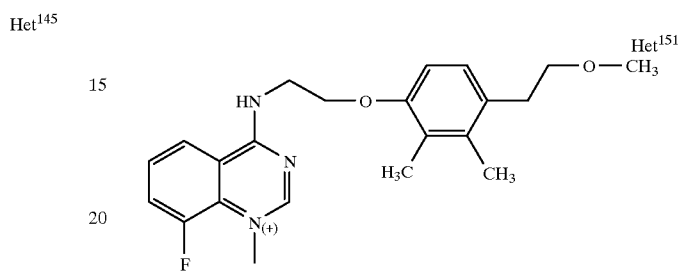
Het151
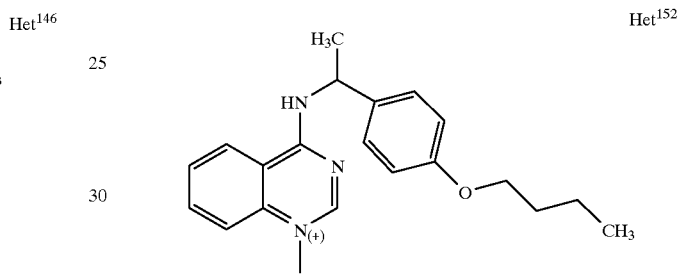
Het152
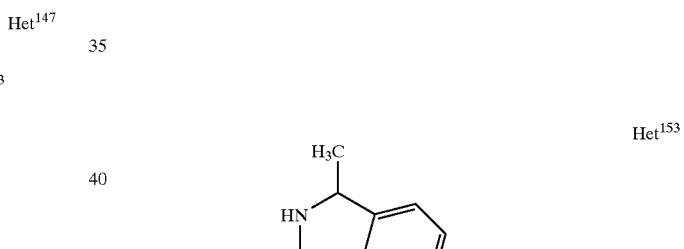
Het153
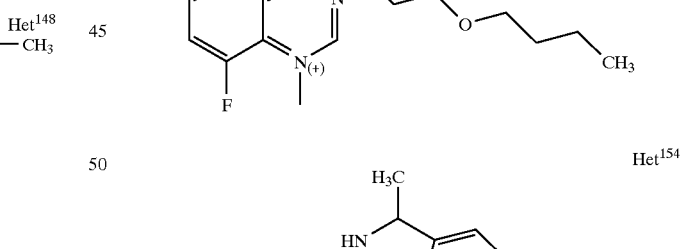
Het154

-continued
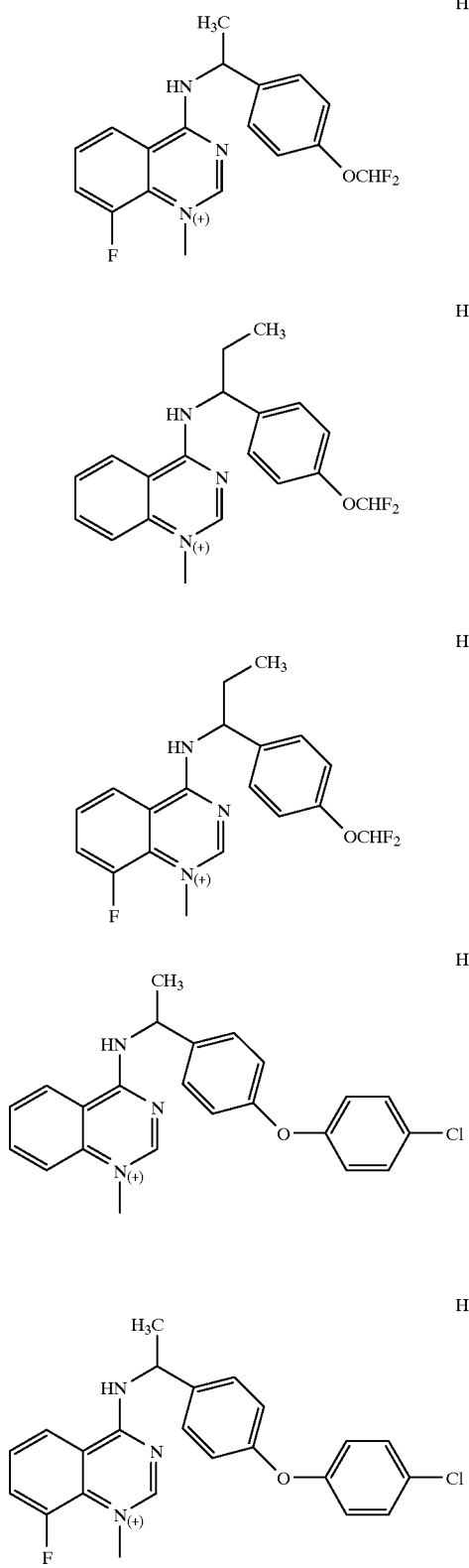
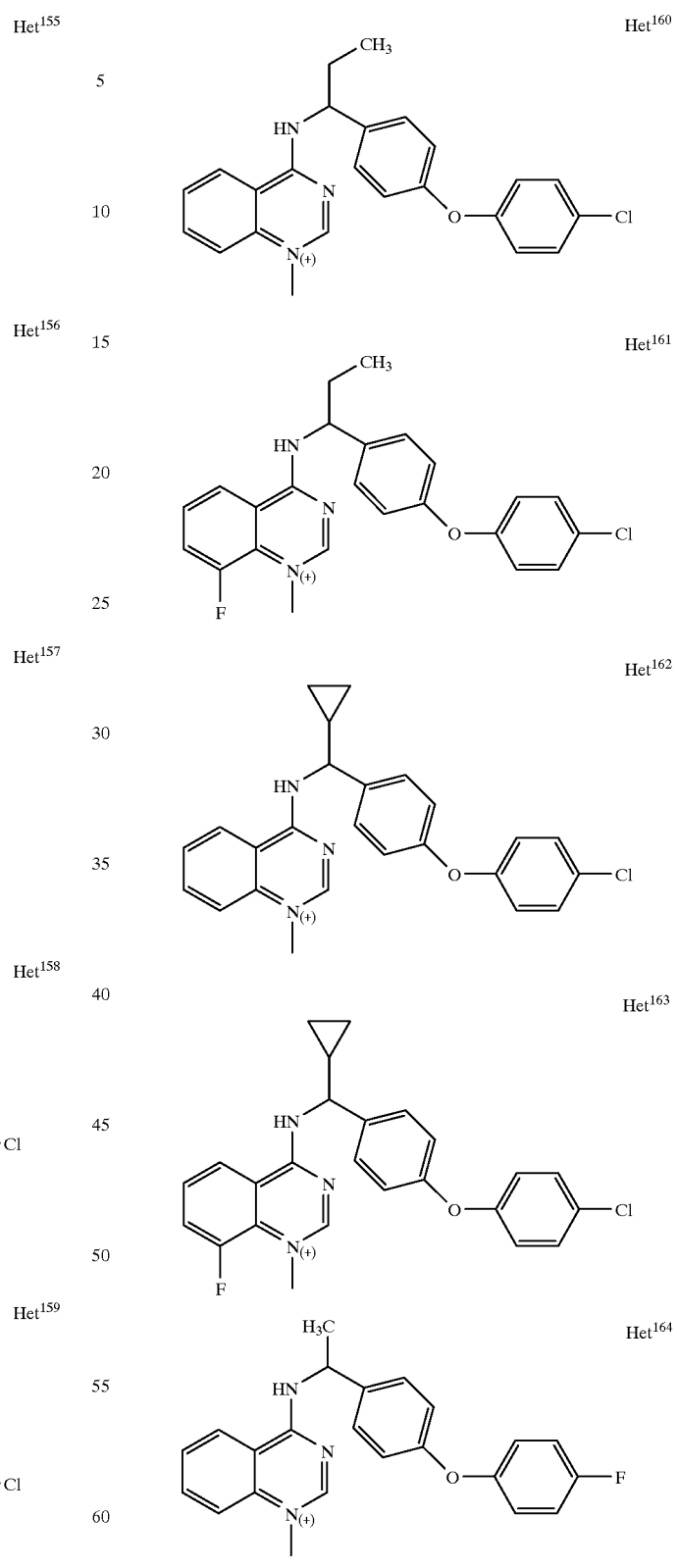

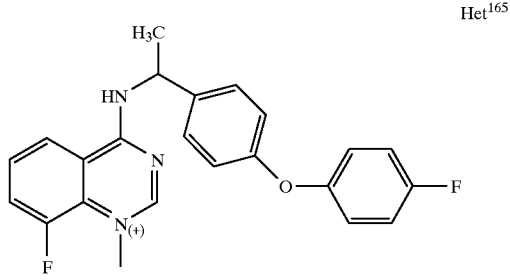
Het¹⁶⁵
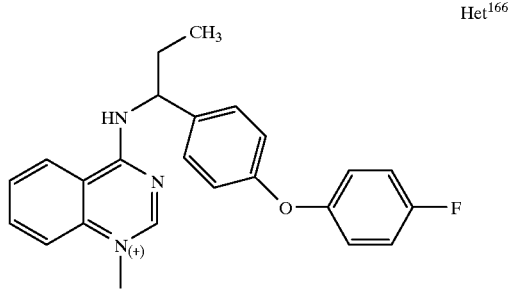
Het¹⁶⁶
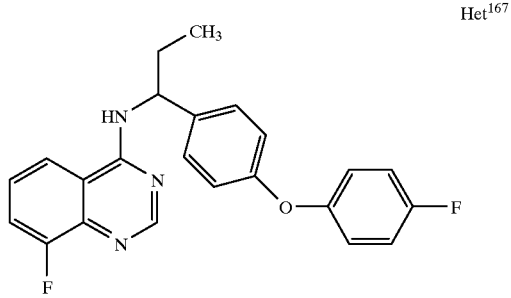
Het¹⁶⁷
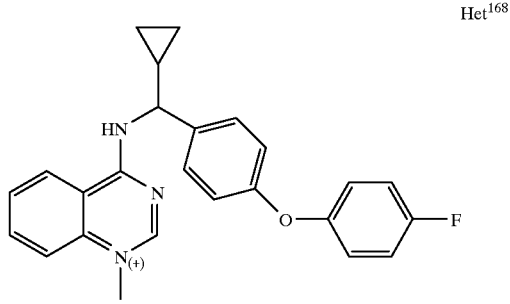
Het¹⁶⁸
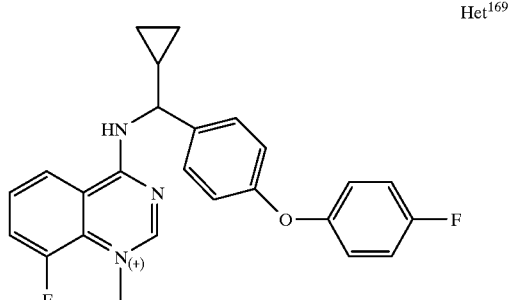
Het¹⁶⁹
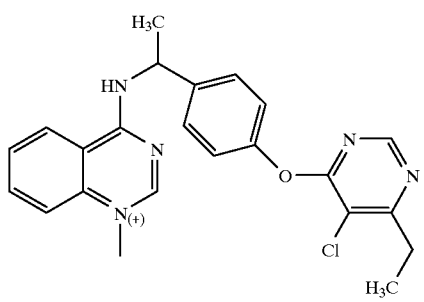
Het¹⁷⁰
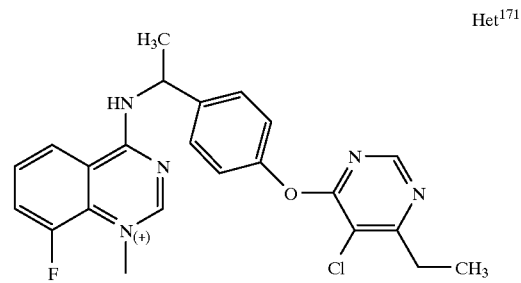
Het¹⁷¹
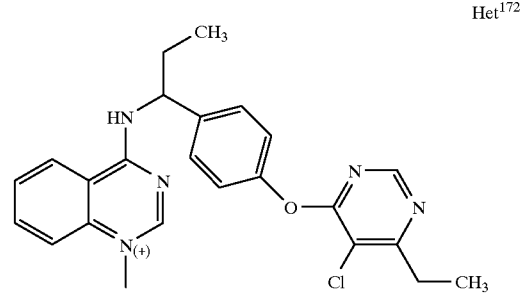
Het¹⁷²
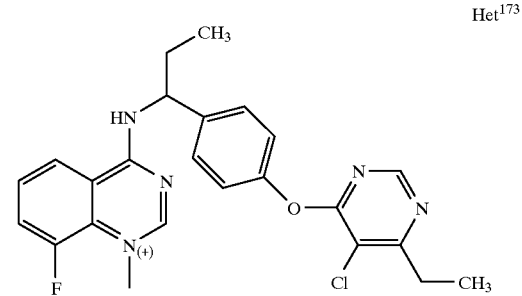
Het¹⁷³
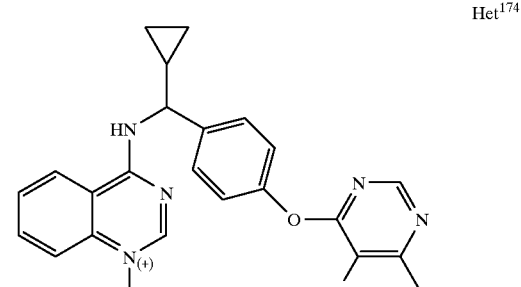
Het¹⁷⁴

Het175
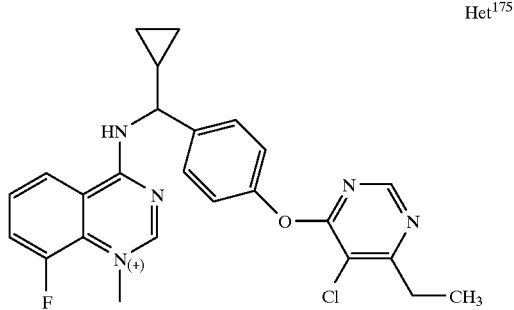
Het176
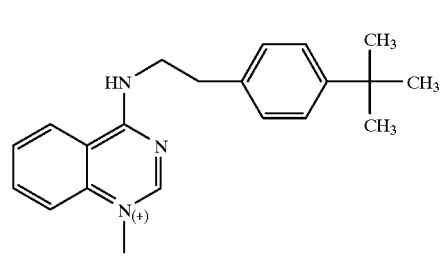
Het177
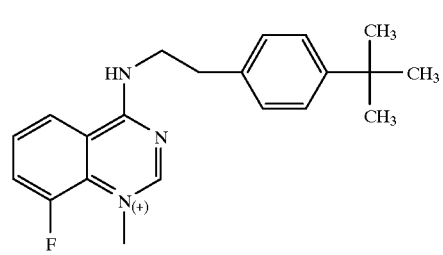
Het178
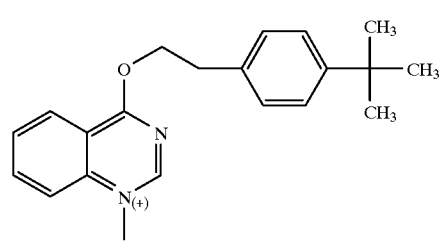
Het179
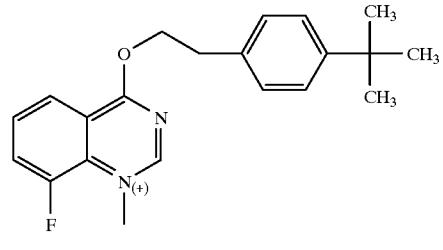
Het180
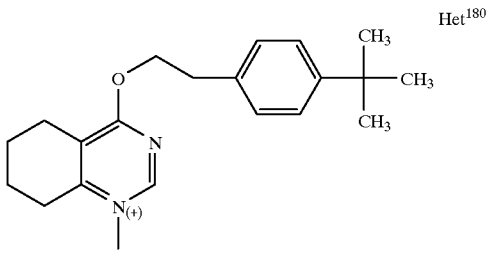
Het181
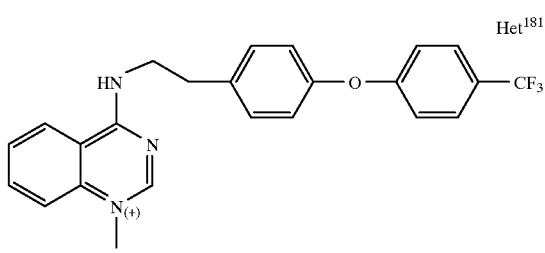
Het182
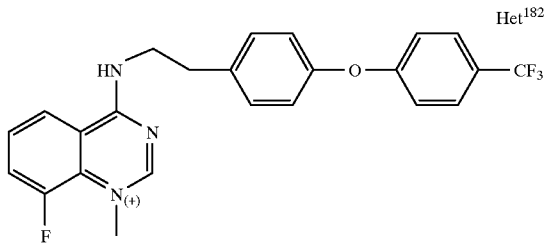
Het183
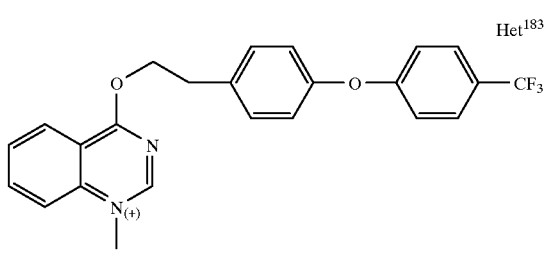
Het184
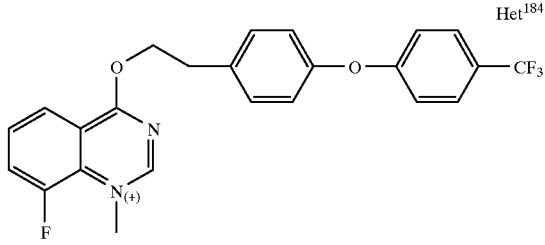
Het185
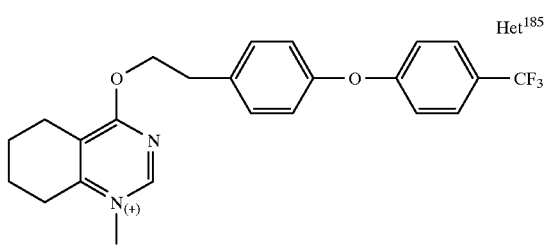

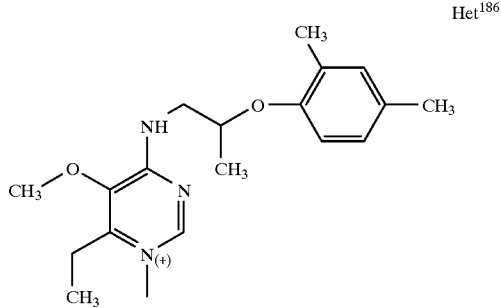 Het¹⁸⁶

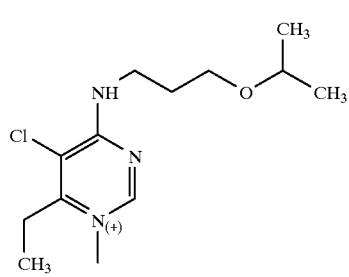 Het¹⁸⁷

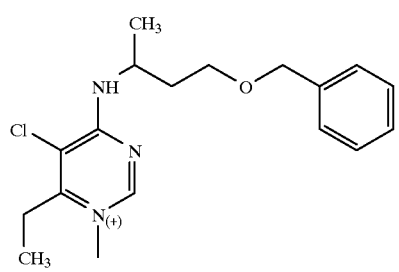 Het¹⁸⁸

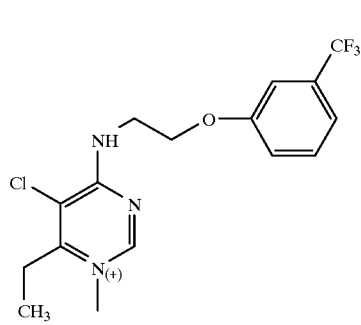 Het¹⁸⁹

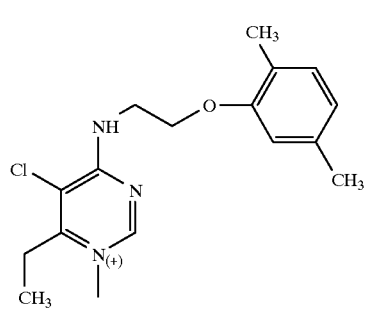 Het¹⁹⁰

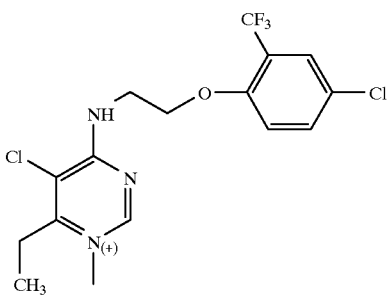 Het¹⁹¹

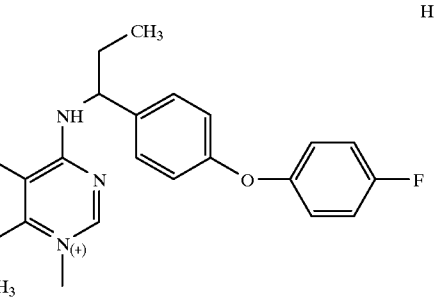 Het¹⁹²

With high probability, the pyrimidine derived heterocycle radicals are of the constitution stated. However, it can not be excluded with absolute certainty that the radical —CHR⁵—E—R⁶ is linked to an N⁺ in position 3 of the pyrimidine system instead of an N⁺ in position 1 of this ring system.

C. BIOLOGICAL EXAMPLES

Use as Insecticide/acaracide/nematicide

Example 1

In each case 1 ml of the preparation to be examined, emulsified in acetone, is applied evenly to the inside of the lid and the bottom of a Petri dish. After the coating has dried, in each case 10 larvae of the German cockroach (*Blattella germanica*) are placed into the Petri dish. The dishes are sealed and kept at room temperature, and after 3 days, the mortality of the test animals is determined. At a concentration of 300 ppm (based on the content of active compound), the preparations of Example No. 24 and 25 effect a mortality of 90–100% among the test animals used.

Example 2

1 ml of an aqueous solution of the formulated preparation to be examined is pipetted onto a filter disk. After the solution had dried, this filter is placed in a Petri dish and populated with 10 L2 larvae of the southern corn rootworm (*Diabrotica undecimpunctata*). After having been kept for 2 days in a climatized chamber at 26° C., the mortality is determined. At a concentration of 300 ppm (based on the content of active compound), the preparations of Example No. 25 effect a mortality of 90–100% among the test animals used.

Example 3

Cut stems of bean plants (Phaseolus vulgaris) carrying one leaf are transferred into brown glass bottles filled with tap water and subsequently populated with approximately 100 spider mites (Tetranychus urticae). The plant leaf and the spider mites are sprayed to run-off point with an aqueous solution of the formulated preparation to be examined. After the formulation has run off, plants and animals are stored in a climatized chamber (16 hours of light/day, 25° C., 40–60% relative atmospheric humidity). After 6 days' storage, the effect of the preparation on all stages of the spider mite is determined. At a concentration of 300 ppm (based on the content of active compound), the preparations of Example No. 24 and 25 cause a mortality of 90–100%.

Example 4

Culture medium (freeze-dried cube) is dipped into an aqueous solution of the formulated preparation to be examined and then placed in a Petri dish. 10 L2 larvae of the Egyptian cotton leaf worm (*Spodoptera litoralis*) are then placed in the Petri dish, which is subsequently sealed with a lid. After 4 days storage at about 23° C., the effect of the preparation on the larvae is determined. At a concentration of 300 ppm (based on the content of active compound), the preparations of Example No. 24 cause a 90–100% mortality or the larvae.

Example 5

(Contact activity): Approximately 5000 recently hatched, active (mobile) larvae (2nd development stage) of root gall nematodes (*Meloidogyne incognita*) are placed into a glass vessel containing an aqueous solution of the formulated preparation to be examined. After the nematode larvae have been continuously exposed for 2 days, the percentage of the specimens which have ceased to move (been immobilized) owing to the effect of the preparation is determined by comparison with the untreated controls (percent nematicidal contact activity).

At a concentration of 3 ppm (based in each case on the content of active compound), the preparations of Example No. 24 and 25 have a 90–100% activity against the root gall nematode *Meloidogyne incognita*.

Example 6

A Petri dish whose bottom is covered with filter paper and which contains about 5 ml of culture medium is prepared. 10 L2 larvae of the Egyptian cotton leaf worm (*Spodoptera litoralis*) are counted into a small beaker. 200 µl of an aqueous solution of the formulated preparation to be examined are pipetted into the beaker. The treated larvae are then poured into the Petri dish and a further 200 µl of the aqueous solution are spread over the culture medium. The Petri dish is sealed and then stored at about 25° C. in a climatized chamber. After 6 days' storage, the effect of the preparation on the larvae is determined. At a concentration of 300 ppm (based on the content of active compound), the preparation of Example No. 526 effects a mortality of 90–100% among the larvae.

Example 7

A Petri dish whose bottom is covered with filter paper and which contains about 5 ml of culture medium is prepared. Pieces of filter paper with about 30, 24-hour-old eggs of the tobacco budworm (*Heliothis virescens*) are dipped into an aqueous solution of the formulated preparation to be examined for 5 seconds and subsequently placed in the Petri dish. A further 200 µl of the aqueous solution are spread over the culture medium. The Petri dish is sealed and then kept at about 25° C. in a climatized chamber. After 6 days' storage, the effect of the preparation on the eggs and the larvae which may have hatched from these is determined. At a concentration of 300 ppm (based on the content of active compound), the preparations of Example No. 219, 526 and 528 cause a mortality of 90–100%.

Example 8

The leaves of 12 rice plants having a stem length of 8 cm are dipped for 5 seconds into an aqueous solution of the formulated preparation to be examined. After the solution has run off, the rice plants treated in this manner are placed in a Petri dish and populated with about 20 larvae (L3 stage) of the rice leafhopper species *Nilaparvata lugens*. The Petri dish is sealed and stored in a climatized chamber (16 hours of light/day, 25° C., 40–60% relative atmospheric humidity). After 6 days' storage, the mortality among the leafhopper larvae is determined. At a concentration of 300 ppm (based on the content of active compound), the preparations of Example No. 526, 528 and 780 effect a mortality of 90–100%.

Example 9

A Petri dish, half of whose bottom is covered with filter paper and which contains a germinated maize corn on a moist cotton pad, is prepared. About 50, 4–5-day-old eggs of the southern corn rootworm (*Diabrotica undecimpunctata*) are transferred onto the filter paper. Three drops of 200 µl of an aqueous solution of the formulated preparation to be examined are pipetted onto the eggs, and the rest is pipetted onto the maize corn. The Petri dish is sealed and stored at about 25° C. in a climatized chamber. After 6 days' storage, the effect of the preparation on the eggs and the larvae which may have hatched from these is determined. At a concentration of 300 ppm (based on the content of active compound), the preparations of Example No. 179, 219 and 526 effect a mortality of 90–100%.

Example 10

Cut stems of bean plants (*Phaseolus vulgaris*) carrying one leaf are transferred into brown glass bottles filled with tap water and subsequently populated with approximately 100 spider mites (*Tetranychus urticae*). Plant leaf and spider mites are then dipped for 5 seconds into an aqueous solution of the formulated preparation to be examined. After the solution has run off, plants and animals are stored in a climatized chamber (16 hours of light/day, 25° C., 40–60% relative atmospheric humidity). After 6 days' storage, the effect on the preparation on all stages of the spider mites is determined. At a concentration of 300 ppm (based on the content of active compound), the preparations of Example No. 179, 219, 486, 528 and 780 effect a mortality of 90–100%.

Example 11

(Contact activity): Approximately 5000 recently hatched, active (mobile) larvae (2nd development stage) of the root gall nematode (*Meloidogyne incognita*) are placed into a glass vessel containing an aqueous solution of the formulated preparation to be examined (final volume 20 ml). After the nematode larvae have been continuously exposed for 6 days, the percentage of the specimens which have ceased to move (been immobilized) owing to the effect of the preparation is determined by comparison with the untreated controls (percent nematicidal contact activity).

At a concentration of 3 ppm, the preparations of Example No. 219, 526, 528 and 780 have a 90–100% activity against the root gall nematode *Meloidogyne incognita*.

Use as Fungicide

The compounds were examined for activity against one or more of the following organisms:

*Plasmopara viticola*
*Phytophthora infestans*
*Pyricularia oryzae*
*Leptosphaeria nodorum*

Aqueous solutions or dispersions of the compounds in the desired concentration were applied to leaves or stems of the test plant after a wetting agent had been added. The plants or the parts of plants were inoculated with the respective test pathogen and kept under controlled environmental conditions suitable for plant growth and the development of the disease. After a suitable period of time, the degree of infection of the diseased plant was scored visually. The compounds are assessed in accordance with a scale from 1 to 3 in which 1 means no control to modest control 2 means average control and 3 means good to complete control. At a concentration of 500 ppm or less, the following compounds were given a rating of 2 or more against the fungi listed.

Example 12

Activity Against *Plasmopara Viticola* (downy mildew)

The following compounds were given a rating of 2 or more: Examples No. 25, 179, 187

Example 13

Activity Against *Phytophthora Infestans*

The following compounds were given a rating of 2 or more: Example No. 24, 25.

Example 14

Activity Against *Pyricularia oryzae*

The following compounds were given a rating of 2 or more: Examples No. 25, 179

Example 15

Activity Against *Leptosphaeria nodorum*

The following compound was given a rating of 2 or more: Example No. 179

TOXICOLOGICAL EXAMPLE

Example 16

The test substances are dissolved in dimethylformamide to give a 20% strength solution, and soya oil is added to give a 1% strength solution, for example, for testing a substance in a dosage of 50 mg/kg, 20 mg of test substance are dissolved in 0.1 ml of DMF and soya oil is added to give 2 ml of solution.

Fasting male Wistar rats having a bodyweight of 80–100 g serve as test animals. The test substances are administered per os (orally) by stomach tube. The volume of the above solution that is applied is 0.5 ml per rat.

The follow-up period is 7 days after administration, and toxic effects or death of test animals are recorded.

We claim:
1. A compound of the formula I,

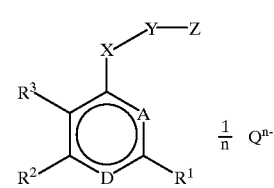

(I)

in which
(1) A is nitrogen and D is $N^+R$ or
A is $N^+R$ and D is nitrogen;
R is

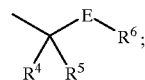

(2) $Q^{n-}$ is any inorganic or organic anion, n being 1, 2, 3 or 4;
(3) $R^1$ is hydrogen, halogen, $(C_1-C_4)$-alkyl, $(C_1-C_4)$-haloalkyl or $(C_3-C_5)$-cycloalkyl;
(4) $R^2$ and $R^3$ are identical or different and are each hydrogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_1-C_8)$-trialkylsilylalkynyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_1-C_4)$-alkoxy-$(C_1-C_4)$-haloalkyl, $(C_1-C_4)$-haloalkoxy-$(C_1-C_4)$-haloalkyl, halogen, hydroxyl, $(C_1-C_4)$-hydroxyalkyl, $(C_1-C_4)$-alkanoyl, $(C_1-C_4)$-alkanoyl-$(C_1-C_4)$alkyl, $(C_1-C_4)$-haloalkanoyl, $(C_3-C_5)$-cycloalkyl, $(C_3-C_5)$-halocycloalkyl, cyano, $(C_1-C_4)$-cyanoalkyl, nitro, $(C_1-C_4)$-nitroalkyl, thiocyano, $(C_1-C_4)$-thiocyanoalkyl, $(C_1-C_4)$-alkoxycarbonyl, $(C_1-C_4)$-alkoxycarbonyl-$(C_1-C_4)$-alkyl, $(C_1-C_4)$-haloalkoxycarbonyl, $(C_1-C_4)$-alkylthio, $(C_1-C_4)$-alkylthio-$(C_1-C_4)$-alkyl, $(C_1-C_4)$-haloalkylthio, $(C_1-C_4)$-alkylsulfinyl, $(C_1-C_4)$-haloalkylsulfinyl, $(C_1-C_4)$-alkylsulfonyl or $(C_1-C_4)$-haloalkylsulfonyl; or
$R^2$ and $R^3$, together with the carbon atoms to which they are attached, form an unsaturated 5- or 6-membered isocyclic ring which may, if it is a 5-membered ring, contain an oxygen or sulfur atom instead of $CH_2$, or which may, if it is a 6-membered ring, contain one or two nitrogen atoms instead of one or two CH units, and which may be substituted by 1, 2 or 3 identical or different radicals, these radicals being $(C_1-C_4)$-alkyl, $(C_1-C_4)$-haloalkyl, halogen, $(C_1-C_4)$-alkoxy or $(C_1-C_4)$-haloalkoxy; or
$R^2$ and $R^3$, together with the carbon atoms to which they are attached, form a saturated 5-, 6- or 7-membered isocyclic ring which may contain oxygen and/or sulfur instead of one or two $CH_2$ groups and which may be substituted by 1, 2 or 3 $(C_1-C_4)$-alkyl groups;
(5) X is O or NH
and the group Y-Z may have the following meanings:
a) Y is $CHR^7$ and $R^7$ is hydrogen, $(C_1-C_4)$-alkyl or $(C_3-C_6)$-cycloalkyl and
Z is a branched or straight-chain, saturated or unsaturated $(C_1-C_{20})$-hydrocarbon radical in which one or more, nonadjacent carbon units may be replaced by a carbonyl group or by the hetero atom units oxygen or $S(O)_x$, where $x=0$, 1 or 2, and where these hydrocarbon radicals with or without the variations mentioned may be substituted by one or more, (in the case of fluorine up to the maximum number), identical or different radicals selected from the group consisting of halogen, hydroxyl, $(C_3-C_6)$-cycloalkyl, $(C_3-C_6)$-cycloalkenyl, deca-, tetra- or dihydronaphthyl, substituted or unsubstituted benzyloxy, substituted or unsubstituted phenylthio, substituted or unsubstituted benzylthio, imidazol-1-yl, triazol-1-yl, pyrazol-1-yl, $(C_1-C_4)$-alkoxycarbonyl or by a group M—G—$R^8$ in which M is oxygen or NH, G is carbonyl, thiocarbonyl or sulfonyl and $R^8$ is $(C_1-C_8)$-alkyl, $(C_3-C_6)$-cycloalkyl, $(C_1-C_8)$-haloalkyl, $(C_1-C_8)$-alkoxy, a substituted or unsubstituted phenyl group, a substituted or unsubstituted phenoxy group, a substituted or unsubstituted anilino group, imidazol-1-yl, triazol-1-yl, pyrazol-1-yl or mono- or di-$(C_1-C_4)$-alkylamino, or, if not included in the above definition, b) Y is a $(C_1-C_6)$-alkylene unit, branched or straight-chain, which may substituted by up to 3 halogen atoms, or by a hydroxyl, $(C_1-C_4)$-alkoxy, $(C_3-C_6)$-cycloalkyl or cyano group and Z is an unsubstituted or substituted aryl, aryloxy, heterocyclyl or pyridinyloxy group with or without substitution, where the aryloxy or pyridinyloxy group is separated from X by at least 2 carbon atoms, or c) in the case that X is NH,
Y is a carbonyl or thiocarbonyl group and
Z is a substituted or unsubstituted aryl-$(C_1-C_4)$-alkyl radical, a $(C_1-C_4)$-alkyl radical which is in each case substituted by a substituted or unsubstituted heterocyclic or benzo-fused carbocyclic or heterocyclic ring system or a $(C_3-C_8)$-cycloalkyl or cycloalkenyl radical with or without substitution;

(6) a) $R^4$ and $R^5$ are identical or different and are each hydrogen, a branched or straight-chain, saturated or unsaturated $(C_1-C_{20})$-hydrocarbon radical, halogen, aryl, substituted aryl or $(C_3-C_6)$-cycloalkyl;

E is oxygen, $S(O)q$ where $q=0$, 1 or 2, or $NR^{19}$, where $R^{19}$ is hydrogen, $(C_1-C_4)$-alkyl, $(C_2-C_4)$-alkenyl or $(C_1-C_4)$-acyl, $R^6$ is a saturated or unsaturated, branched or straight-chain $(C_1-C_{20})$-hydrocarbon radical, $(C_3-C_6)$-cycloalkyl, aryl, substituted aryl or

where V is oxygen or sulfur, and $R^{20}$ is a branched or straight-chain, saturated or unsaturated $(C_1-C_{20})$-hydrocarbon radical, aryl, substituted aryl, heterocyclyl, substituted heterocyclyl, $(C_3-C_6)$-cycloalkyl, $(C_3-C_6)$-cycloalkenyl
and where in the $(C_1-C_{20})$-hydrocarbon radicals mentioned under $R^6$ one or more nonadjacent $CH_2$ groups may be replaced by a carbonyl group or by hetero atom radicals selected from the group consisting of O, $S(O)y$, where $y=0$, 1 or 2, $NR^{10"}$ or $SiR^{13"}R^{14"}$, where $R^{10"}$, $R^{13"}$ and $R^{14"}$ have the meaning of $R^{10}$, $R^{13}$ and $R^{14}$, and where additionally 3 to 6 carbon atoms of these hydrocarbon radicals may form a cycle and where these hydrocarbon radicals with or without the abovementioned variations may be substituted by one or more, identical or different radicals selected from the group consisting of hydroxyl, $(C_1-C_4)$-alkyl, halogen, $(C_1-C_4)$-haloalkyl, $(C_3-C_6)$-cycloalkyl, $(C_1-C_4)$-acyl, phenoxy, substituted phenoxy, phenyl, substituted phenyl, phenylthio, substituted phenylthio and $NR^{21}R^{22}$, where $R^{21}$ and $R^{22}$ independently of each other are each hydrogen, $(C_1-C_4)$-alkyl, $(C_2-C_4)$-alkenyl, $(C_1-C_4)$-acyl, aryl, substituted aryl, heteroaryl or benzoyl; or if, E is $NR^{19}$ and $R^6$ is

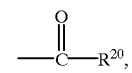

$R^{19}$ and $R^{20}$ together may also be $(C_3-C_6)$-alkylene where a $CH_2$ group adjacent to the nitrogen may be replaced by CO and/or where a $CH_2CH_2$ group may be replaced by a group CH=CH or o-phenylene, or furthermore b) $R^4$ is hydrogen, halogen or $(C_1-C_4)$-alkyl,
$R^5$ is hydrogen, halogen, a branched or straight-chain, saturated or unsaturated $(C_1-C_{20})$-hydrocarbon radical, $(C_3-C_6)$-cycloalkyl, aryl or substituted aryl,
E is

where V' is oxygen, sufur or $NR^{23}$ and
$R^{23}$ is aryl, substituted aryl, heteroaryl, substituted heteroaryl, hydroxyl, $(C_1-C_4)$-alkoxy, aryloxy, substituted aryloxy, heteroaryloxy, substituted heteroaryloxy or mono- or disubstituted amino and
$R^6$ is a branched or straight-chain, saturated or unsaturated $(C_1-C_{20})$-hydrocarbon, respectively substituted or unsubstituted aryl or heteroaryl or $(C_3-C_8)$-cycloalkyl;
and the abovementioned aryl and heteroaryl radicals may be substituted by one or more, identical or different radicals $QR^q$, where
Q is a direct bond, $NR^{24}$, O, $S(O)_s$, where $s=0$, 1 or 2, $OSO_2$, $SO_2O$, $NR^{25}SO_2$, $SO_2NR^{26}$, $SiR^{27}R^{28}$ or

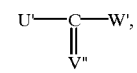

where
$R^{27}$ and $R^{28}$ are $(C_1-C_4)$-are alkyl or phenyl;
U' is a direct bond, $NR^{29}$ or O;
V" is oxygen or sulfur;
W' is a direct bond, $NR^{30}$ or oxygen, where $R^{24}$, $R^{25}$, $R^{26}$, $R^{29}$ and $R^{30}$ are identical or different and are each hydrogen, $(C_1-C_4)$-alkyl, $(C_1-C_4)$-alkoxy, $(C_1-C_4)$-alkanoyl or $(C_3-C_6)$-cycloalkyl;

$R^q$ are substituents which are independent of one another and are each halogen, hydroxy, cyano, nitro, a branched or straight-chain, saturated or unsaturated $(C_1-C_{20})$-hydrocarbon radical, $(C_3-C_8)$-cycloalkyl or $(C_4-C_8)$-cycloalkenyl, where in the 3 last radicals one or more, nonadjacent saturated carbon units may be replaced by a carbonyl group or by hetero atom units selected from the group consisting of oxygen, $S(O)_x$,
where
X=0, 1 or 2, $NR^{31}$ or $SiR^{32}R^{33}$ and where these last 5 radicals with or without the variations mentioned may be substituted by one or more, identical or different radicals $T^1R^{34}$, or $R^q$ is aryl or heterocyclyl, where these two radicals may be unsubstituted or substituted by up to three (in the case of fluorine up to the maximum number) identical or different radicals $T^2R^{35}$, or two adjacent radicals $QR^q$ together with the carbon atoms that they are attached to may form a fused cycle having 4 to 6 ring atoms which is carbocyclic or contains hetero ring atoms selected from the group consisting of O, S and N and which is unsubstituted or substituted by one or more radicals selected from the group consisting of halogen $(C_1-C_4)$-alkyl and oxo, or $R^{24}$, $R^{26}$ and $R^{28}$ independently of one another may form with the $R^q$ located at Q a 4- to 8-membered ring system in which one or two $CH_2$ groups, may be replaced by hetero atom units selected from oxygen, $S(O)_t$, where t=0, 1 or 2, or $NR^{36}$,
where $R^{31}$ is hydrogen, $(C_1-C_4)$-alkyl, $(C_1-C_4)$-alkoxy or $(C_1-C_4)$-alkanoyl;

$R^{32}$ and $R^{33}$ independently of one another are each $(C_1-C_4)$-alkyl, $T^1$ and $T^2$ are in each case independent of the other and are each a direct bond, oxygen, $S(O)_k$, $SO_2O$, CO, OCO, COO, $NR^{37}$, $SO_2NR^{37}$, $NR^{37}SO_2$, $ONR^{37}$, $NR^{37}O$, $NR^{37}CO$, $CONR^{37}$ or $SiR^{38}R^{39}$ and k=0, 1 or 2, where $R^{37}$ independently of the others is hydrogen, $(C_1-C_4)$-alkyl, $(C_1-C_4)$-alkanoyl or $(C_3-C_5)$-cycloalkyl;

$R^{38}$ and $R^{39}$ independently of one another are each $(C_1-C_4)$-alkyl;

$R^{34}$ and $R^{35}$ independently of one another are each hydrogen, cyano, nitro, halogen, $(C_1-C_8)$-alkyl, $(C_1-C_8)$-haloalkyl, $(C_2-C_8)$-alkenyl, $(C_2-C_8)$-haloalkenyl, $(C_2-C_8)$-alkynyl, $(C_2-C_8)$-haloalkynyl, $(C_1-C_8)$-alkoxy-$(C_1-C_4)$-alkyl, $(C_1-C_8)$-haloalkoxy-$(C_1-C_4)$-alkyl, $(C_1-C_8)$-alkylthio-$(C_1-C_4)$-alkyl, $(C_1-C_8)$-haloalkylthio-$(C_1-C_4)$-alkyl, $(C_3-C_8)$-cycloalkyl, $(C_4-C_8)$-cycloalkenyl, $(C_3-C_8)$-cycloalkyl-$(C_1-C_4)$-alkyl, $(C_4-C_8)$-cycloalkenyl-$(C_1-C_4)$-alkyl, aryl, heterocyclyl, aryl-$(C_1-C_4)$-alkyl or heterocyclyl-$(C_1-C_4)$-alkyl, where in these last 8 radicals the cycloaliphatic, aromatic or heterocyclic ring systems may be unsubstituted or substituted by up to three (in the case of fluorine up to the maximum number) identical or different substituents $R^{40}$, or $R^{34}$ and $R^{35}$, located at the same carbon atom, together are an oxo group,
where $R^{40}$ is $(C_1-C_4)$-alkyl, $(C_1-C_4)$-haloalkyl, $(C_1-C_4)$-alkoxy, $(C_1-C_4)$-haloalkoxy, cyano, nitro or halogen;

$R^{36}$ is hydrogen, $(C_1-C_8)$-alkyl, $(C_1-C_4)$-haloalkyl, $(C_1-C_4)$-alkoxy, $(C_1-C_4)$-alkylthio, $(C_3-C_5)$-cycloalkyl, $(C_2-C_4)$-alkenyl, $(C_2-C_4)$-alkynyl, $(C_1-C_4)$-alkanoyl, $(C_2-C_4)$-haloalkanoyl, $(C_2-C_4)$-alkoxy-alkyl, phenyl-$(C_1-C_4)$-alkyl or phenyl and the phenyl groups are unsubstituted or substituted by up to three (in the case of fluorine up to the maximum number) identical or different substituents $R^{41}$,
where $R^{41}$ is $(C_1-C_4)$-alkyl, $(C_1-C_4)$-haloalkyl, $(C_1-C_4)$-alkoxy, $(C_1-C_4)$-alkylthio, halogen or cyano;

and in the $(C_1-C_{20})$-hydrocarbon radicals mentioned under a) and b) under $R^4$, $R^5$ and $R^6$, unless defined otherwise, one or more, nonadjacent $CH_2$ groups may be replaced by a carbonyl group or by hetero atom radicals selected from $S(O)y$, where y=0, 1 or 2, $NR^{10'''}$ or $SiR^{13'''}R^{14'''}$, where additional 3 to 6 carbon atoms of these hydrocarbon radicals may form a cycle, and where these hydrocarbon radicals with or without the abovementioned variations may be substituted by one or more, identical or different radicals selected from the group consisting of halogen, $(C_3-C_8)$-cycloalkyl, phenoxy, substituted phenoxy, phenyl, substituted phenyl, and where furthermore the radicals of the meanings "aryl", "substituted aryl", "aryloxy", "substituted aryloxy", "heterocyclyl", "substituted heterocyclyl", "phenyl", "substituted phenyl", "phenoxy", "substituted phenoxy", "phenylthio", "substituted phenylthio", "branched or straightchain, saturated or unsaturated $(C_1-C_{20})$-hydrocarbon" listed for $R^4$, $R^5$, $R^6$ and E under a) and b), unless defined otherwise, have the meanings given above under YZ and where furthermore in the radicals listed above for the radicals $R^4$, $R^5$, $R^6$ and E as radicals, substituents or components of ring systems, unless defined otherwise, the hydrogen atoms may be replaced partly, in the case of fluorine even wholly, by halogen.

2. A compound of the formula I as claimed in claim 1, in which $R^1$ is hydrogen, methyl, chlorine or fluorine;

$R^2$ and $R^3$ are each hydrogen, $(C_1-C_4)$-alkyl, $(C_2-C_4)$-alkenyl, $(C_2-C_4)$-alkynyl, trimethylsilylethynyl, methoxycarbonyl, $(C_1-C_4)$-haloalkyl, halogen, $(C_1-C_4)$-alkoxy, methoxymethyl or cyano; or $R^2$ and $R^3$, together with the carbon atoms to which they are attached form an unsaturated 5- or 6-membered ring with or without substitution which may, if it is a 5-membered ring, contain a sulfur atom instead of a $CH_2$ unit; or $R^2$ and $R^3$, together with the carbon atoms to which they are attached form a saturated 5- or 6-membered ring which may contain a sulfur or an oxygen atom instead of a $CH_2$ unit;

X is NH.

3. A compound of the formula I as claimed in claim 1, in which $R^1$ is hydrogen;

$R^2$ and $R^3$ are each hydrogen, methyl, ethyl, propyl, ($C_2$–$C_3$)-alkenyl, ($C_2$–$C_3$)-chloro- or -fluoroalkenyl, ($C_2$–$C_3$)-alkynyl, trimethylsilylethynyl, ($C_1$–$C_3$)-chloro- or -fluoroalkyl, methoxy, methoxymethyl, halogen or cyano;

$R^2$ and $R^3$, together with the ring system to which they are attached form the quinazoline or quinoline system which may be substituted in the carbocyclic moiety by fluorine; or $R^2$ and $R^3$, together with the carbon atoms to which they are attached form a saturated 6-membered ring which may contain an oxygen or sulfur atom instead of a $CH_2$ group.

4. A compound of the formula I as claimed in claim 1, in which $R^1$ is hydrogen;

$R^2$ is methyl, ethyl, propyl, isopropyl, ($C_1$–$C_2$)-fluoroalkyl or methoxymethyl;

$R^3$ is fluorine, chlorine, bromine, cyano, vinyl, ethynyl or methoxy; or $R^2$ and $R^3$, together with the ring system to which they are attached form the quinazoline system which may be substituted by a fluorine atom; A and D, in the case that Y Z have the meanings given under a) and b), describe the pyrimidine system and, in the case that Y Z has the meanings given under c), describe the pyridine system;

X is NH.

5. A compound of the formula I as claimed in claim 1, in which $R^1$ is hydrogen;

$R^2$ is ethyl or methoxymethyl;

$R^3$ is chlorine, bromine or methoxy;

X is NH.

6. A process for preparing compounds of the formula I as claimed in claim 1, which comprises reacting a compound of the formula (V)

$$\underset{R^2}{\overset{R^3}{\diagup}}\underset{N}{\overset{X-Y-Z}{\bigvee_{G}}}R^1 \quad (V)$$

where G is CH or N and $R^1$, $R^2$, $R^3$, X, Y and Z are each as defined under formula I, with an electrophile of the formula (VI)

$$\underset{R^4}{\overset{L}{\diagup}}\underset{R^5}{\overset{E}{\diagdown}}R^6 \quad (VI)$$

where $R^4$, $R^5$, $R^6$ and E are each as defined under formula I and L is a leaving group, if appropriate with the addition of salts, and replacing, if appropriate, the anion of the compounds obtained in this manner by other anions.

7. A fungicidal composition, comprising a fungicidally effective amount of at least one compound as claimed in claim 1 together with an inert additive or auxiliary.

8. An insecticidal, acaricidal, nematicidal, or an endo- or ectoparasitical composition comprising an effective amount of at least one compound as claimed in claim 1 together with an inert additive or auxiliary.

9. A composition for use in protecting wood or as a preservative in sealing compounds, in paints, in cooling lubricants for metalwork or in drilling and cutting oils, which comprises an effective amount of at least one compound as claimed in claim 1 together with an inert auxiliary and additive.

10. A method for controlling phytopathogenic fungi, which comprises applying a fungicidally effective amount of a compound as claimed in claim 1 to these fungi or to the plants, areas or substrates infested with them or to seeds.

11. A method for controlling harmful insects, acarids and nematodes, which comprises applying an effective amount of a compound as claimed in claim 1 to these harmful insects, acarids and nematodes or to the plants, areas or substrates infested with them.

12. Seed, treated or coated with an effective amount of a compound as claimed in claim 1.

13. Seed, treated or coated with an effective amount of a composition as claimed in claim 7.

14. A compound according to claim 1, in which $R^1$ is hydrogen, and $R^2$ is ethyl, and $R^3$ is bromine or chlorine; or $R^2$ is methoxymethyl and $R^3$ is methoxy.

15. A compound according to claim 1, which has the formula $$\left[ \begin{array}{c} CH_3O \\ CH_3O \end{array} \underset{H_2C-CO}{\overset{HN}{\bigvee_{N}^{N}}} \underset{}{\overset{CH_3}{\diagup}} \underset{}{\overset{}{\diagdown}} CH_3 \right]^+ Br^-$$

16. The process according to claim 6, wherein L is halogen, alkylthio, alkanesulfonyloxy or arylsulfonyloxy.

17. A fungicidal composition according to claim 7, which further comprises an active substance selected from the group consisting of fungicides, insecticides, attractants, sterilants, ascaricides, nematicides, and herbicides.

18. An insecticidal, acaricidal, or nematicidal composition according to claim 8, which comprises an active substance selected from the group consisting of fungicides, insecticides, attractants, sterilants, ascaricides, nematicides, and herbicides.

19. A method for protecting crops from fungi which comprises applying to said crops or to an environment in which they reside an effective amount of the fungicidal composition according to claim 17.

20. A method for protecting crops from insects, acarids and nematodes, which comprises applying to said crops or to an environment in which they reside an effective amount of insecticidal, acaricidal or nematicidal composition according to claim 18.

* * * * *